US011881294B2

(12) United States Patent
Gross et al.

(10) Patent No.: US 11,881,294 B2
(45) **Date of Patent: *Jan. 23, 2024**

(54) SYSTEMS AND METHODS FOR A WEB PLATFORM HOSTING ONE OR MORE ASSESSMENTS OF HUMAN VISUAL PERFORMANCE

(71) Applicant: RightEye, LLC, Bethesda, MD (US)

(72) Inventors: Adam Todd Gross, Potomac, MD (US); Melissa Hunfalvay, Silver Spring, MD (US)

(73) Assignee: RightEye, LLC, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/837,117

(22) Filed: Jun. 10, 2022

(65) Prior Publication Data

US 2022/0301669 A1 Sep. 22, 2022

Related U.S. Application Data

(63) Continuation of application No. 16/838,696, filed on Apr. 2, 2020, now Pat. No. 11,393,564, which is a (Continued)

(51) Int. Cl.
*G16H 10/60* (2018.01)
*A61B 3/113* (2006.01)
(Continued)

(52) U.S. Cl.
CPC ............. *G16H 10/60* (2018.01); *A61B 3/028* (2013.01); *A61B 3/113* (2013.01); *A61B 3/18* (2013.01);
(Continued)

(58) Field of Classification Search
CPC ........ G16H 10/60; G16H 20/30; G16H 40/67; G16H 50/30
See application file for complete search history.

(56) References Cited

U.S. PATENT DOCUMENTS 4,896,959 A 1/1990 O'Brien
5,360,971 A 11/1994 Kaufman et al.
(Continued)

FOREIGN PATENT DOCUMENTS

WO WO-2016110804 A1 * 7/2016 ............... A61B 3/16

OTHER PUBLICATIONS

Plochl et al., "Combining EEG and eye tracking: identification, characterization, and correction of eye movement artifacts in electroencephalographic data", Frontiers in Human Neuroscience (Year: 2012).*

(Continued)

*Primary Examiner* — Joshua B Blanchette
(74) *Attorney, Agent, or Firm* — Bookoff McAndrews, PLLC

(57) ABSTRACT

Systems and methods are disclosed hosting multiple visual assessments, evaluating user performance on the assessments, and providing recommendations to assess and improve user visual performance. One method includes hosting a plurality of visual assessments; presenting, via a web portal, a user interface for selecting one or more visual assessments of the hosted plurality of visual assessments; receiving, via a web portal, a request for a user to access a visual assessment, wherein the visual assessment is an assessment out of the hosted plurality of assessments; administering the visual assessment to the user; receiving user performance data associated with a user, in response to the administered visual assessment; comparing the user performance data with performance data associated with one or more other users; and generating a report of user visual performance based on the user performance data, wherein the report is accessible to the user via the web portal.

19 Claims, 26 Drawing Sheets

Related U.S. Application Data continuation of application No. 15/342,230, filed on Nov. 3, 2016, now Pat. No. 10,643,741.

(51) Int. Cl.

| | |
|---|---|
| ***G16H 50/30*** | (2018.01) |
| ***G06F 3/01*** | (2006.01) |
| ***A61B 3/028*** | (2006.01) |
| ***G16H 20/30*** | (2018.01) |
| ***G16H 40/67*** | (2018.01) |
| ***A61B 3/18*** | (2006.01) |

(52) U.S. Cl.

CPC ............. *G06F 3/013* (2013.01); *G16H 20/30* (2018.01); *G16H 40/67* (2018.01); *G16H 50/30* (2018.01)

(56) References Cited

U.S. PATENT DOCUMENTS

| | | | | |
|---|---|---|---|---|
| 5,422,690 | A | 6/1995 | Rothberg et al. | |
| 5,942,954 | A | 8/1999 | Galiana et al. | |
| 6,943,754 | B2 | 9/2005 | Aughey et al. | |
| 7,357,507 | B2 | 4/2008 | Waldorf et al. | |
| 7,540,615 | B2 | 6/2009 | Merzenich et al. | |
| 7,682,021 | B2 | 3/2010 | Sabel | |
| 7,699,466 | B2 | 4/2010 | Hayakawa et al. | |
| 7,708,700 | B2 | 5/2010 | Ghajar | |
| 7,736,000 | B2 | 6/2010 | Enriquez et al. | |
| 7,740,352 | B2 | 6/2010 | Kopren | |
| 7,819,818 | B2 | 10/2010 | Ghajar | |
| 7,881,493 | B1 | 2/2011 | Edwards et al. | |
| 7,963,652 | B2 | 6/2011 | Vertegaal et al. | |
| 8,016,770 | B2 | 9/2011 | Chiba et al. | |
| 8,020,991 | B2 | 9/2011 | Zhang et al. | |
| 8,020,992 | B2 | 9/2011 | Zhang et al. | |
| 8,100,532 | B2 | 1/2012 | Yoo et al. | |
| 8,136,943 | B2 | 3/2012 | Yoo et al. | |
| 2003/0211449 | A1 | 11/2003 | Seiller et al. | |
| 2003/0232319 | A1 | 12/2003 | Grisham et al. | |
| 2004/0015098 | A1 | 1/2004 | Souvestre | |
| 2008/0212032 | A1* | 9/2008 | Seiller | G09B 19/0038 351/222 |
| 2008/0278682 | A1* | 11/2008 | Huxlin | A61H 5/00 351/203 |
| 2009/0096983 | A1 | 4/2009 | Provitola | |
| 2010/0070453 | A1 | 3/2010 | Yoo et al. | |
| 2010/0204608 | A1 | 8/2010 | Sugio et al. | |
| 2010/0220291 | A1* | 9/2010 | Horning | G06V 40/19 351/210 |
| 2010/0249532 | A1 | 9/2010 | Maddess et al. | |
| 2011/0009777 | A1 | 1/2011 | Reichow et al. | |
| 2011/0085139 | A1 | 4/2011 | Blixt et al. | |
| 2011/0172556 | A1 | 7/2011 | Jones et al. | |
| 2012/0051597 | A1 | 3/2012 | Fogt | |
| 2012/0092618 | A1 | 4/2012 | Yoo et al. | |
| 2012/0281181 | A1* | 11/2012 | Chen | G06F 3/013 351/159.76 |
| 2013/0293844 | A1* | 11/2013 | Gross | A61B 3/0025 351/209 |
| 2014/0055591 | A1 | 2/2014 | Katz | |
| 2014/0320397 | A1 | 10/2014 | Hennessey et al. | |
| 2015/0279226 | A1 | 10/2015 | Harrison et al. | |
| 2015/0280970 | A1 | 10/2015 | Heda et al. | |
| 2016/0005320 | A1 | 1/2016 | deCharms et al. | |

OTHER PUBLICATIONS

Andersson, Richard, et al. "Sampling frequency and eye-tracking measures: how speed affects durations, latencies, and more." Journal of Eye Movement Research 3.3 (2010).

* cited by examiner

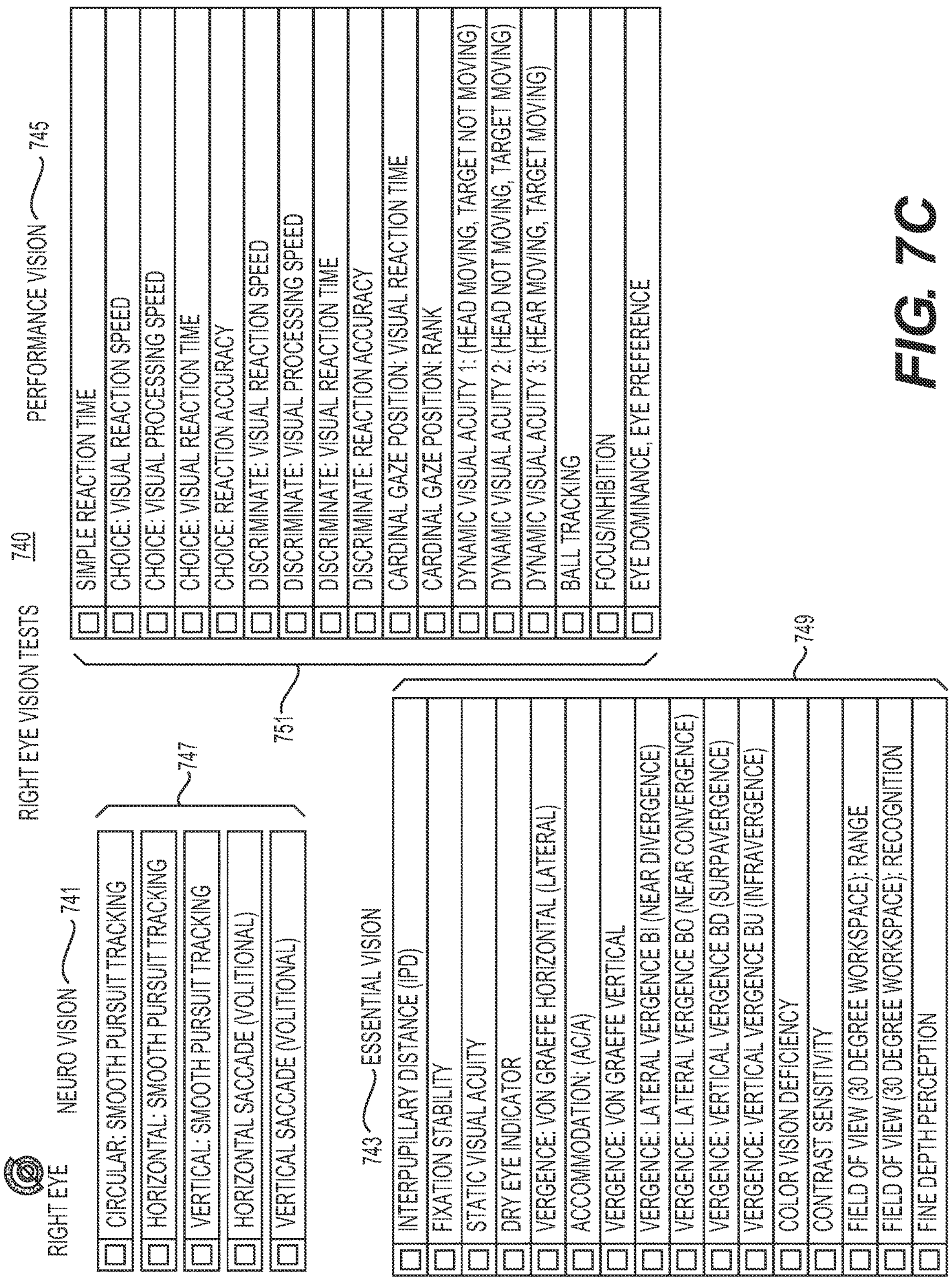

FIG. 7C

RIGHT EYE VISION TESTS

RIGHT EYE

NEURO VISION — 741
- ☐ CIRCULAR: SMOOTH PURSUIT TRACKING
- ☐ HORIZONTAL: SMOOTH PURSUIT TRACKING
- ☐ VERTICAL: SMOOTH PURSUIT TRACKING
- ☐ HORIZONTAL SACCADE (VOLITIONAL)
- ☐ VERTICAL SACCADE (VOLITIONAL)

— 747

PERFORMANCE VISION — 745

740
- ☐ SIMPLE REACTION TIME
- ☐ CHOICE: VISUAL REACTION SPEED
- ☐ CHOICE: VISUAL PROCESSING SPEED
- ☐ CHOICE: VISUAL REACTION TIME
- ☐ CHOICE: REACTION ACCURACY
- ☐ DISCRIMINATE: VISUAL REACTION SPEED
- ☐ DISCRIMINATE: VISUAL PROCESSING SPEED
- ☐ DISCRIMINATE: VISUAL REACTION TIME
- ☐ DISCRIMINATE: REACTION ACCURACY
- ☐ CARDINAL GAZE POSITION: VISUAL REACTION TIME
- ☐ CARDINAL GAZE POSITION: RANK
- ☐ DYNAMIC VISUAL ACUITY 1: (HEAD MOVING, TARGET NOT MOVING)
- ☐ DYNAMIC VISUAL ACUITY 2: (HEAD NOT MOVING, TARGET MOVING)
- ☐ DYNAMIC VISUAL ACUITY 3: (HEAR MOVING, TARGET MOVING)
- ☐ BALL TRACKING
- ☐ FOCUS/INHIBITION
- ☐ EYE DOMINANCE, EYE PREFERENCE

— 751

ESSENTIAL VISION — 743
- ☐ INTERPUPILLARY DISTANCE (IPD)
- ☐ FIXATION STABILITY
- ☐ STATIC VISUAL ACUITY
- ☐ DRY EYE INDICATOR
- ☐ VERGENCE: VON GRAEFE HORIZONTAL (LATERAL)
- ☐ ACCOMMODATION: (AC/A)
- ☐ VERGENCE: VON GRAEFE VERTICAL
- ☐ VERGENCE: LATERAL VERGENCE BI (NEAR DIVERGENCE)
- ☐ VERGENCE: LATERAL VERGENCE BO (NEAR CONVERGENCE)
- ☐ VERGENCE: VERTICAL VERGENCE BD (SURPAVERGENCE)
- ☐ VERGENCE: VERTICAL VERGENCE BU (INFRAVERGENCE)
- ☐ COLOR VISION DEFICIENCY
- ☐ CONTRAST SENSITIVITY
- ☐ FIELD OF VIEW (30 DEGREE WORKSPACE): RANGE
- ☐ FIELD OF VIEW (30 DEGREE WORKSPACE): RECOGNITION
- ☐ FINE DEPTH PERCEPTION

— 749

760a

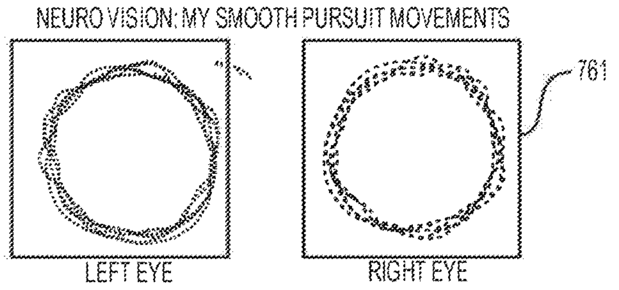

763 IMAGE EXPLANATION

765 REPORT EXPLANATION

767

CIRCULAR SMOOTH PURSUIT

| METRICS | LEFT EYE | | RIGHT EYE | | BOTH | |
|---|---|---|---|---|---|---|
| | ACTUAL | PERCENTILE | ACTUAL | PERCENTILE | ACTUAL | PERCENTILE |
| EYE/TARGET VELOCITY ERROR (DEGREES) | 15.35° | | 15.00° | | 15.20° | |
| HORIZONTAL SYNCHRONIZATION SPEM (0-1) | 0.89 | | 0.90 | | 0.91 | |
| VERTICAL SYNCHRONIZATION SPEM (0-1) | 0.89 | | 0.87 | | 0.89 | |
| SMOOTH PURSUIT (PERCENTAGE) | 92.86% | | 94.92% | | 95.56% | |
| SMOOTH PURSUIT ON TARGET (PERCENTAGE) | 38.79% | | 44.40% | | 61.07% | |
| PREDICTIVE SMOOTH PURSUIT (PERCENTAGE | 16.88% | | 39.19% | | 17.58% | |
| LATENT SMOOTH PURSUIT (PERCENTAGE) | 44.34% | | 16.41% | | 21.36% | |

769 TABLE EXPLANATION

HORIZONTAL SMOOTH PURSUIT

| METRIC | LEFT EYE ACTUAL/PERCENTILE | RIGHT EYE ACTUAL/PERCENTILE | BOTH ACTUAL/PERCENTILE | REMEDY |
|---|---|---|---|---|
| BLINK RATE | 0.7% | 0.7% | 0.7% | SEE VISION SPECIALIST |
| BLINK NUMBER | 2 | 2 | 2 | SEE VISION SPECIALIST |
| EYE/TARGET VELOCITY ERROR | 14 DEGREES | 14 DEGREES | 14 DEGREES | SEE VISION SPECIALIST |
| HORIZONTAL SYNCHRONIZATION | 0.90 | 0.89 | 0.90 | SEE VISION SPECIALIST |
| SMOOTH PURSUIT PERCENTAGE | 90 | 90 | 90 | SEE VISION SPECIALIST |
| SMOOTH PURSUIT ON TARGET (%) | 40 | 42 | 45 | SEE VISION SPECIALIST |
| LATENT SMOOTH PURSUIT (%) | 40 | 30 | 35 | SEE VISION SPECIALIST |
| PREDICTIVE SMOOTH PURSUIT (%) | 16 | 17 | 16 | SEE VISION SPECIALIST |
| SACCADE PERCENTAGE | 10 | 10 | 10 | SEE VISION SPECIALIST |
| NUMBER OF SACCADES | 20 | 21 | 20 | SEE VISION SPECIALIST |

VERTICAL SMOOTH PURSUIT

| METRIC | LEFT EYE ACTUAL/PERCENTILE | RIGHT EYE ACTUAL/PERCENTILE | BOTH ACTUAL/PERCENTILE | REMEDY |
|---|---|---|---|---|
| BLINK RATE | 0.7% | 0.7% | 0.7% | SEE VISION SPECIALIST |
| BLINK NUMBER | 2 | 2 | 2 | SEE VISION SPECIALIST |
| EYE/TARGET VELOCITY ERROR | 15 DEGREES | 15 DEGREES | 15 DEGREES | SEE VISION SPECIALIST |
| HORIZONTAL SYNCHRONIZATION | 0.90 | 0.90 | 0.90 | SEE VISION SPECIALIST |
| SMOOTH PURSUIT PERCENTAGE | 89 | 89 | 89 | SEE VISION SPECIALIST |
| SMOOTH PURSUIT ON TARGET (%) | 50 | 50 | 50 | SEE VISION SPECIALIST |
| LATENT SMOOTH PURSUIT (%) | 25 | 25 | 25 | SEE VISION SPECIALIST |
| PREDICTIVE SMOOTH PURSUIT (%) | 25 | 25 | 25 | SEE VISION SPECIALIST |
| SACCADE PERCENTAGE | 15 | 11 | 11 | SEE VISION SPECIALIST |
| NUMBER OF SACCADES | 20 | 21 | 20 | SEE VISION SPECIALIST |

HORIZONTAL SACCADE

| METRIC | MY EYES (LEFT, RIGHT, BOTH) | POPULATION AVERAGE | RANGE | REMEDY |
|---|---|---|---|---|
| SACCADE (NUMBER) | 62 | 60 | 50-80 | SEE VISION SPECIALIST |
| SACCADE (%) | 40 | 50 | 30-60 | SEE VISION SPECIALIST |
| FIXATION (NUMBER) | 33 | 35 | 15-40 | SEE VISION SPECIALIST |
| FIXATION (%) | 60 | 50 | 20-80 | SEE VISION SPECIALIST |
| TARGET HITS (NUMBER) | 10 | 8 | 6-15 | SEE VISION SPECIALIST |
| TARGET OVERSHOT (NUMBER) | 3 | 2 | 1-5 | SEE VISION SPECIALIST |
| TARGET UNDERSHOT (NUMBER) | 6 | 5 | 1-8 | SEE VISION SPECIALIST |
| TARGET MISSES (NUMBER) | 4 | 5 | 1-10 | SEE VISION SPECIALIST |

VERTICAL SACCADE

| METRIC | MY EYES (LEFT, RIGHT, BOTH) | POPULATION AVERAGE | RANGE | REMEDY |
|---|---|---|---|---|
| SACCADE (NUMBER) | 60 | 60 | 50-80 | SEE VISION SPECIALIST |
| SACCADE (%) | 38 | 50 | 30-60 | SEE VISION SPECIALIST |
| FIXATION (NUMBER) | 30 | 35 | 15-40 | SEE VISION SPECIALIST |
| FIXATION (%) | 62 | 50 | 20-80 | SEE VISION SPECIALIST |
| TARGET HITS (NUMBER) | 11 | 8 | 6-15 | SEE VISION SPECIALIST |
| TARGET OVERSHOT (NUMBER) | 3 | 2 | 1-5 | SEE VISION SPECIALIST |
| TARGET UNDERSHOT (NUMBER) | 3 | 5 | 1-8 | SEE VISION SPECIALIST |
| TARGET MISSES (NUMBER) | 7 | 5 | 1-10 | SEE VISION SPECIALIST |

ESSENTIAL VISION

DISTANCE BETWEEN YOUR EYES

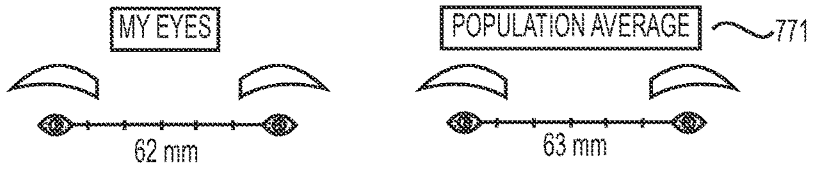

| METRICS | MY EYES | POPULATION AVERAGE | RANGE | REMEDY |
|---|---|---|---|---|
| DISTANCE BETWEEN YOUR EYES (mm) | 62 mm | 63 mm | 48-73 mm | NOT APPLICABLE |

DISTANCE BETWEEN YOUR EYES (INTERPUPILLARY DISTANCE) MAY BE MEASURED FROM THE CENTER OF YOUR LEFT AND RIGHT PUPILS

STATIC VISUAL ACUITY

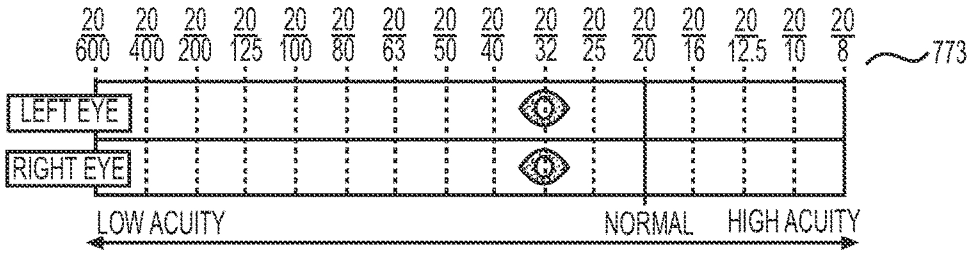

| METRICS | MY EYES LEFT/RIGHT | POPULATION AVERAGE | RANGE | REMEDY |
|---|---|---|---|---|
| STATIC VISUAL ACUITY | 20/32L<br>20/32R | 20/20 | 20/8 TO 20/600<br>LEGALLY BLIND = 20/200<br>ELITE = 20/8 | SEE VISION SPECIALIST |

STATIC VISUAL ACCUITY (SVA) MAY REFER TO HOW CLEARLY YOU CAN SEE AN OBJECT THAT CHANGES SIZE BUT DOES NOT MOVE.

EYE DOMINANCE

| METRICS | MY EYES LEFT/RIGHT | POPULATION AVERAGE | RANGE | REMEDY |
|---|---|---|---|---|
| EYE DOMINANCE | 20/32L<br>20/32R | 80% RIGHT / 20% LEFT | WEAK 61% TO STRONG 39% | TRAINING DRILLS |
| DEGREE OF DOMINANCE | 30 DEGREES | 20 DEGREES | 0-3 IS WEAK DOMINANCE<br>4+ IS STRONG DOMINANCE | TRAINING DRILLS |

EYE DOMINANCE OR EYE PREFERENCE MAY REFER TO THE TENDENCY TO PREFER VISUAL INPUT FROM ONE EYE OVER THE OTHER.

VON GRAEFE NEAR HORIZONTAL HETEROPHORIA

| METRIC | MY MEASUREMENTS (ESO/EXO/ORTHO) | POPULATION AVERAGE (cm) | RANGE | REMEDY |
|---|---|---|---|---|
| VON GRAEFE | 2 ESO | 2-4 EXO | ORTHO TO +/-0.25 | SEE VISION SPECIALIST |

ESO (+) EYES DEVIATE INWARDS. EXO (-) EYES DEVIATE OUTWARDS. ORTHO EYES ARE STRAIGHT.

ACCOMMODATIONS AC/A RATIO

| METRIC | MY EYES | POPULATION AVERAGE (cm) | RANGE SD | REMEDY |
|---|---|---|---|---|
| REPORT FOR AC/A RATIO | 4:1 | 4:1 | 5:1 HIGH, 3:1 TO 4:1 RANGE | SEE VISION SPECIALIST |

ESO ( + ) EYES DEVIATE INWARDS. EXO ( - ) EYES DEVIATE OUTWARDS. ORTHO EYES ARE STRAIGHT.

VON GRAEFE NEAR VERTICAL HETEROPHORIA

| METRIC | MY MEASUREMENTS (ESO/EXO/ORTHO) | POPULATION AVERAGE (cm) | RANGE SD | REMEDY |
|---|---|---|---|---|
| VON GRAEFE | 2 EXO | 2-4 EXO | ORTHO TO +/-0.25 | SEE VISION SPECIALIST |

ESO (+) EYES DEVIATE INWARDS. EXO (-) EYES DEVIATE OUTWARDS. ORTHO EYES ARE STRAIGHT.

NEAR DIVERGENCE

| METRIC | MY MEASUREMENT | POPULATION AVERAGE (cm) | RANGE SD | REMEDY |
|---|---|---|---|---|
| FAR BI BLUR | 5 | 5.2 | 1.6 | TRAINING DRILLS |
| FAR BI BREAK | 9 | 8.4 | 1.6 | TRAINING DRILLS |
| FAR BI RECOVERY | 5.5 | 5.2 | 2 | TRAINING DRILLS |

BI MAY REFER TO BASE IN DIVERGENCE OF THE EYES.

NEAR CONVERGENCE

| METRIC | MY MEASUREMENT | POPULATION AVERAGE (cm) | RANGE SD | REMEDY |
|---|---|---|---|---|
| FAR BI BLUR | 7 | 6.8 | 2 | TRAINING DRILLS |
| FAR BI BREAK | 8 | 8.4 | 2.4 | TRAINING DRILLS |
| FAR BI RECOVERY | 6 | 4.4 | 6.8 | TRAINING DRILLS |

BO MAY REFER TO BASE OUT CONVERGENCE OF THE EYES.

VERTICAL VERGENCE (SUPRAVERGENCE) NEAR BD/OD/DU OS BREAK & RECOVERY

| METRIC | MY MEASUREMENT | POPULATION AVERAGE (cm) | RANGE SD | REMEDY |
|---|---|---|---|---|
| NEAR BU BREAK | 8 | 8.4 | 2.4 | TRAINING DRILLS |
| NEAR BU RECOVERY | 5 | 4.4 | 6.8 | TRAINING DRILLS |

BU MAY REFER TO BASE-UP

COLOR DEFICIENCY

| METRIC | MY EYES | POPULATION AVERAGE (cm) | RANGE SD | REMEDY |
|---|---|---|---|---|
| COLOR DEFICIENCY | NORMAL | NORMAL | PROTAN: 1% MALE. 0.01% FEMALE. DEUTAN: 5% MALE, 0.4% FEMALE. TRITAN: VERY RARE. | SEE VISION SPECIALIST |

PROTAN MAY REFER TO TROUBLE DISTINGUISHING RED-GREEN, RED-ORANGE, BLUE-GREEN AND GREY. DEUTAN MAY REFER TO TROUBLE DISTINGUISHING BLUE-GREEN FROM GRAY AND RED-PURPLE. TRITAN MAY CONFUSE VIOLET WITH GRAY AND YELLOW-GREEN.

FIELD OF VIEW

| METRIC | MY MEASUREMENT | POPULATION AVERAGE (cm) | RANGE SD | REMEDY |
|---|---|---|---|---|
| FIELD OF VIEW RANGE | 15,6 | UNKNOWN | UNKNOWN | SEE VISION SPECIALIST |
| FIELD OF VIEW RECOGNITION | 15,6 | UNKNOWN | UNKNOWN | SEE VISION SPECIALIST |
| ILLUMINATION LEVEL (%) | 50% | UNKNOWN | UNKNOWN | SEE VISION SPECIALIST |

THIS REPORT MAY SHOW TARGETS THAT WERE MISSED. FIELD OF VIEW RANGE MAY REFER TO WHICH TARGETS WERE NOT SEEN BY YOUR EYES. FIELD OF VIEW RECOGNITION MAY REFER TO WHICH TARGETS WERE NOT SEEN AND NOT CORRECTLY IDENTIFIED. IF A ZERO IS REPORTED THIS MAY MEAN YOU DID NOT MISS ANY TARGETS AT THE LOWEST LEVEL OF CONTRAST.

FIXATION STABILITY

| METRICS | MY EYES (%) LEFT/RIGHT/BOTH | POPULATION AVERAGE | RANGE | REMEDY |
|---|---|---|---|---|
| VISUAL STABILITY | 84/86/90 | 50/50/50 | 0-100% | SEE VISION SPECIALIST |

FIXATION STABILITY MAY REFER TO THE ABILITY TO KEEP YOUR EYES FROM SHIFTING OVER TIME.

VERTICAL VERGENCE (INFRAVERGENCE) NEAR BD/OD/DU OS BREAK & RECOVERY

| METRIC | MY EYES | POPULATION AVERAGE (cm) | RANGE SD | REMEDY |
|---|---|---|---|---|
| NEAR BU BREAK | 8 | 8.4 | 2.4 | TRAINING DRILLS |
| NEAR BU RECOVERY | 4.5 | 4.4 | 6.8 | TRAINING DRILLS |

BU MAY REFER TO BASE-UP

CONTRAST SENSITIVITY

| CONTRAST SENSITIVITY | MY EYES (%) | POPULATION AVERAGE | RANGE | REMEDY |
|---|---|---|---|---|
| TARGET LUMINANCE CD/M2 | 20 CD/M2 | 59.88 CD/M2 | 1-99 | SEE VISION SPECIALIST |
| SURROUND LUMINANCE CD/M2 | 100 CD/M2 | 100 CD/M2 | 100 CD/M2 | SEE VISION SPECIALIST |

FINE DEPTH PERCEPTION

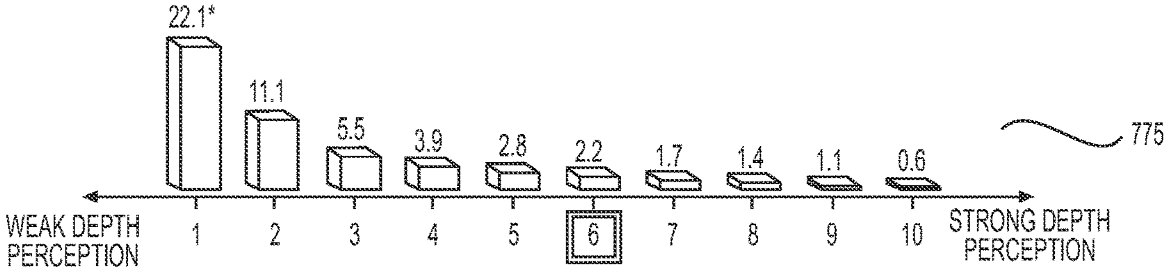

| METRICS | MY EYES | POPULATION AVERAGE | RANGE | REMEDY |
|---|---|---|---|---|
| TEST NUMBER | 6 | 7-9 (ADULTS) | 1-10 | TRAINING DRILLS |
| ANGLE OF STEREOPSIS | 80 ARCSEC | 40 ARCSEC (ADULTS) | 20-800 ARCSEC | TRAINING DRILLS |
| DISTANCE OF DISPARITY | 2.2mm | 1.1 (ADULTS) | 0.55-22.2mm | TRAINING DRILLS |

SENSITIVITY OF YOUR FINE DEPTH PERCEPTION.

DRY EYE INDICATOR

| DRY EYE METRICS | MY SCORE BOTH EYES | NORMS | DRY EYE | REMEDY |
|---|---|---|---|---|
| BLINK RATE (SECONDS) | 1 | 4 | <3 INDICATOR, <2 STRONG INDICATOR | CONSULT OPTOMETRIST |
| BLINK DURATION (% MINUTE) | 1.0 | 0.7% | 0.7-4.5% INDICATOR, >4.5% STRONG INDICATOR | CONSULT OPTOMETRIST |
| EXTENDED BLINKS (#) | 0 | 0 | >0 INDICATOR, >2 STRONG INDICATOR | CONSULT OPTOMETRIST |

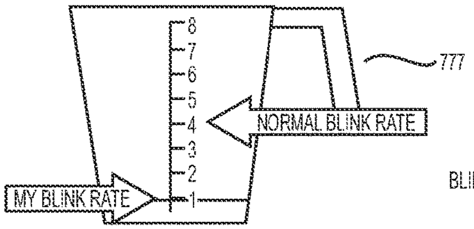

BLINK RATE MAY REFER TO HOW OFTEN YOU BLINK OVER TIME.

PERFORMANCE VISION

SIMPLE REACTION TIME

| METRICS | MY MEASUREMENT (ms) | POPULATION AVERAGE (ms) | RANGE (ms) | REMEDY |
|---|---|---|---|---|
| SIMPLE REACTION TIME | 217 ms | 450 ms | 300-800 ms | TRAINING DRILLS |

SIMPLE REACTION TIME MAY REFER TO HOW LONG IT TOOK YOU TO PRESS THE BUTTON WHEN YOU SAW THE TARGET (ALIEN).

CHOICE REACTION TIME

| METRIC | MY EYES (ms/%) | POPULATION AVERAGE | RANGE | REMEDY |
|---|---|---|---|---|
| VISUAL REACTION SPEED (ms) | 100 ms | 200 ms | 100-250 ms | TRAINING DRILLS |
| PROCESSING SPEED (ms) | 200 ms | 300 ms | 200-400 ms | TRAINING DRILLS |
| REACTION TIME (BUTTON PRESS) | 500 ms | 500 ms | 400-700 ms | TRAINING DRILLS |
| RESPONSE ACCURACY | 100% | 50% | 25-100% | TRAINING DRILLS |

THESE METRICS MAY REFER TO HOW LONG AND HOW ACCURATE IT TOOK YOU TO SEE, PROCESS, AND RESPOND TO THREE DIFFERENT TARGETS (THE STAR, PLANET AND PERSON) EACH WITH A DIFFERENT KEY.

DISCRIMINATE REACTION

| METRIC | MY EYES (ms/%) | POPULATION AVERAGE | RANGE | REMEDY |
|---|---|---|---|---|
| VISUAL REACTION SPEED (ms) | 100 ms | 200 ms | 100-250 ms | TRAINING DRILLS |
| PROCESSING SPEED (ms) | 250 ms | 350 ms | 200-450 ms | TRAINING DRILLS |
| REACTION TIME (BUTTON PRESS) | 550 ms | 500 ms | 450-800 ms | TRAINING DRILLS |
| RESPONSE ACCURACY | 100% | 50% | 25-100% | TRAINING DRILLS |

THESE METRICS MAY REFER TO HOW LONG AND HOW ACCURATE IT TOOK YOU TO SEE, PROCESS, AND RESPOND TO THE STAR WHEN YOU WERE PRESENTED WITH THREE DIFFERENT POSSIBILITIES (STAR, PLANET, AND PERSON).

*FIG. 7K*

780b DYNAMIC VISUAL ACUITY: HEAD AND OBJECT MOVING

| METRICS | MY EYES | POPULATION AVERAGE | RANGE | REMEDY |
|---|---|---|---|---|
| SIZE OF TARGET | 20/100 | 20/100 | 20/100 | TRAINING DRILLS |
| SPEED (mph) | 63 mph | UNKNOWN | 0-53 | TRAINING DRILLS |
| REACTION TIME ms | 200 ms | UNKNOWN | 200-300 ms | TRAINING DRILLS |

DYNAMIC VISUAL ACUITY OF A MOVING OBJECT MAY REFER TO WHAT SPEED YOU CAN ACCURATELY IDENTIFY A MOVING TARGET THE SIZE OF 20/20 WHEN YOUR HEAD IS ALLOWED FREE MOVEMENT.

BALL TRACKING

| BALL TRACKING | MY EYES | POPULATION AVERAGE | RANGE | REMEDY |
|---|---|---|---|---|
| SPEED (mph) | 60 mph | 50 mph | 30-90 mph | TRAINING DRILLS |
| REACTION TIME (ms) | 400 ms | 400 ms | 275-800 ms | TRAINING DRILLS |
| RESPONSE ACCURACY % | 95% | 80% | 20-100% | TRAINING DRILLS |
| TIME-ON-TARGET (%) | 80% | 60% | 20-80% | TRAINING DRILLS |
| SMOOTH PURSUIT (%) | 75% | 63% | 25-100% | TRAINING DRILLS |
| PREDICTIVE SMOOTH PURSUIT (%) | 80% | 50% | 10-95% | TRAINING DRILLS |
| LATENT SMOOTH PURSUIT (%) | 20% | 50% | 10-90% | TRAINING DRILLS |
| SACCADE (%) | 20% | 50% | 10-80% | TRAINING DRILLS |
| FIXATION (%) | 5% | 20% | 10-80% | TRAINING DRILLS |

CARDINAL GAZE POSITION (CGP)

| CARDINAL GAZE POSITION | MY REACTION TIME (ms) LEFT/RIGHT/BOTH | POPULATION AVERAGE (cm) | REMEDY |
|---|---|---|---|
| UPPER LEFT | 360/360/360 | 5/5/4 | TRAINING DRILLS |
| UP 90° | 340/340/340 | 3/3/2 | TRAINING DRILLS |
| UPPER RIGHT | 310/310/310 | 1/1/1 | TRAINING DRILLS |
| LEFT 90° | 630/630/630 | 7/7/6 | TRAINING DRILLS |
| DOWN RIGHT | 360/340/350 | 6/4/3 | TRAINING DRILLS |
| RIGHT 90° | 310/310/310 | 2/2/5 | TRAINING DRILLS |
| DOWN LEFT | 360/360/360 | 4/6/8 | TRAINING DRILLS |
| DOWN 90° | 660/660/660 | 8/8/7 | TRAINING DRILLS |

CARDINAL GAZE POSITION MAY BE A RELATIVE MEASURE OF HOW LONG IT TAKES THE EYE TO TRAVEL IN DIFFERENT DIRECTIONS. 1 MAY BE THE FASTEST DIRECTION, 8 MAY BE THE SLOWEST DIRECTION.

DYNAMIC VISUAL ACUITY: HEAD MOVING, OBJECT STILL

| METRICS | MY EYES | POPULATION AVERAGE | RANGE | REMEDY |
|---|---|---|---|---|
| DYNAMIC VISUAL ACCUITY | 20/50 | 2 LEVELS ABOVE YOUR SVA SCORE | 20/8 - 20/600 | TRAINING DRILLS |

781a

DYNAMIC VISUAL ACUITY STATIONARY OBJECT MAY REFER TO HOW ACCURATELY YOU CAN VIEW A STATIONARY TARGET WHILE YOUR HEAD IS MOVING AT A RATE OF 2 TIMES A SECOND (2Hz).

DYNAMIC VISUAL ACUITY: HEAD STILL, OBJECT MOVING

| METRICS | MY EYES | POPULATION AVERAGE | RANGE | REMEDY |
|---|---|---|---|---|
| SIZE OF TARGET | 20/100 | UNKNOWN | 20/100 | TRAINING DRILLS |
| SPEED (mph) | 52 mph | UNKNOWN | 0-53 mph | TRAINING DRILLS |
| REACTION TIME ms | 220 ms | UNKNOWN | 200-300 ms | TRAINING DRILLS |

781b

DYNAMIC VISUAL ACUITY OF A MOVING OBJECT MAY REFER TO WHAT SPEED YOU CAN ACCURATELY IDENTIFY A MOVING TARGET THE SIZE OF 20/20 WHILE YOUR HEAD REMAINS STILL.

INHIBITION

| INHIBIT | MY EYES NO MOTION/MOTION | POPULATION AVERAGE | RANGE | REMEDY |
|---|---|---|---|---|
| SPEED mph | 60 mph | 50 mph | 30-90% | TRAINING DRILLS |
| REACTION TIME ms | 500 ms | 500 ms | 300-990 ms | TRAINING DRILLS |
| RESPONSE ACCURACY % | 75% | 60% | 10-100% | TRAINING DRILLS |
| TIME-ON-TARGET (%) | 58% | 50% | 10-80% | TRAINING DRILLS |
| TIME-OFF-TARGET (%) | 42% | 50% | 10-90% | TRAINING DRILLS |
| TIME-ON-DISTRACTOR (%) | 80% | 50% | 10-90% | TRAINING DRILLS |

FIG. 7M

SYSTEMS AND METHODS FOR A WEB PLATFORM HOSTING ONE OR MORE ASSESSMENTS OF HUMAN VISUAL PERFORMANCE

RELATED APPLICATIONS

This application is a continuation of and claims the benefit of priority to U.S. patent application Ser. No. 16/838,696, filed on Apr. 2, 2020, which is a continuation of and claims the benefit of priority to U.S. patent application Ser. No. 15/342,230, filed on Nov. 3, 2016, the entire disclosures of which are hereby incorporated herein by reference in their entireties.

TECHNICAL FIELD

Various embodiments of the present disclosure relate generally to evaluating, assessing, and improving human visual performance. More specifically, exemplary embodiments of the present disclosure relate to systems and methods of a web platform hosting multiple visual assessments, evaluating user performance on the assessments, and providing recommendations to improve, maintain, or rehabilitate user visual performance.

BACKGROUND

Visual assessments, including visual assessments for health, leisure, training, or rehabilitation/therapy purposes are increasingly available. For example, mobile phone users can take eye exams via applications. Such applications may provide basic recommendations relative to common eye issues. However, such applications, individually, are limited by eye-tracking capabilities and the ability to interpret received user performance data. In addition, the applications each offer individual exams. Users download each individual application to access tests offered by the individual applications. Since each application interprets granular eye movement data, evaluations are basic, singular interpretations of received user data. In addition each application may house its own eye-tracking capabilities, meaning users may contend with variance in their results from each app and each application or assessment is isolated and unable to leverage user data or performance analytics across applications.

Accordingly, a need exists for systems and methods for managing various visual assessment applications and leveraging the analysis of multiple applications. For example, a need exists for enabling communication between various visual assessment applications, the communication including user access to multiple visual assessment applications, compatibility in receipt of visual assessment data, data exchange between applications, and/or leveraging data analysis capabilities in sharing data. More generally, a need exists for systems and methods for hosting multiple visual assessments, evaluating user performance on the assessments, and providing recommendations to improve, maintain, or rehabilitate user visual performance.

SUMMARY

According to certain embodiments, methods are disclosed for hosting multiple visual assessments, evaluating user performance on the assessments, and providing recommendations to improve, maintain, or rehabilitate user visual performance. One method includes hosting a plurality of visual assessments; presenting, via a web portal, a user interface for selecting one or more visual assessments of the hosted plurality of visual assessments; receiving, via a web portal, a request for a user to access a visual assessment, wherein the visual assessment is an assessment out of the hosted plurality of assessments; administering the visual assessment to the user; receiving user performance data associated with a user, in response to the administered visual assessment; comparing the user performance data with performance data associated with one or more other users; and generating a report of user visual performance based on the user performance data, wherein the report is accessible to the user via the web portal.

According to certain embodiments, systems are disclosed for hosting one or more visual assessments. One system includes a data storage device storing instructions for hosting one or more visual assessments; and a processor configured to execute the instructions to perform a method including: hosting a plurality of visual assessments; presenting, via a web portal, a user interface for selecting one or more visual assessments of the hosted plurality of visual assessments; receiving, via a web portal, a request for a user to access a visual assessment, wherein the visual assessment is an assessment out of the hosted plurality of assessments; administering the visual assessment to the user; receiving user performance data associated with a user, in response to the administered visual assessment; comparing the user performance data with performance data associated with one or more other users; and generating a report of user visual performance based on the user performance data, wherein the report is accessible to the user via the web portal.

According to certain embodiments, a computer readable medium is disclosed storing instructions that, when executed by a computer, cause the computer to perform a method of hosting one or more visual assessments, the method including hosting a plurality of visual assessments; presenting, via a web portal, a user interface for selecting one or more visual assessments of the hosted plurality of visual assessments; receiving, via a web portal, a request for a user to access a visual assessment, wherein the visual assessment is an assessment out of the hosted plurality of assessments; administering the visual assessment to the user; receiving user performance data associated with a user, in response to the administered visual assessment; comparing the user performance data with performance data associated with one or more other users; and generating a report of user visual performance based on the user performance data, wherein the report is accessible to the user via the web portal.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 7C is schematic diagram of an exemplary display of a user interface of visual performance assessments presented to a user via a web portal, according to an exemplary embodiment of the present disclosure;

FIGS. 7D-7M are schematic diagrams of exemplary reports for one or more visual performance assessments available to a user via a web portal, according to an exemplary embodiment of the present disclosure;

DESCRIPTION OF THE EMBODIMENTS

Figure 1:
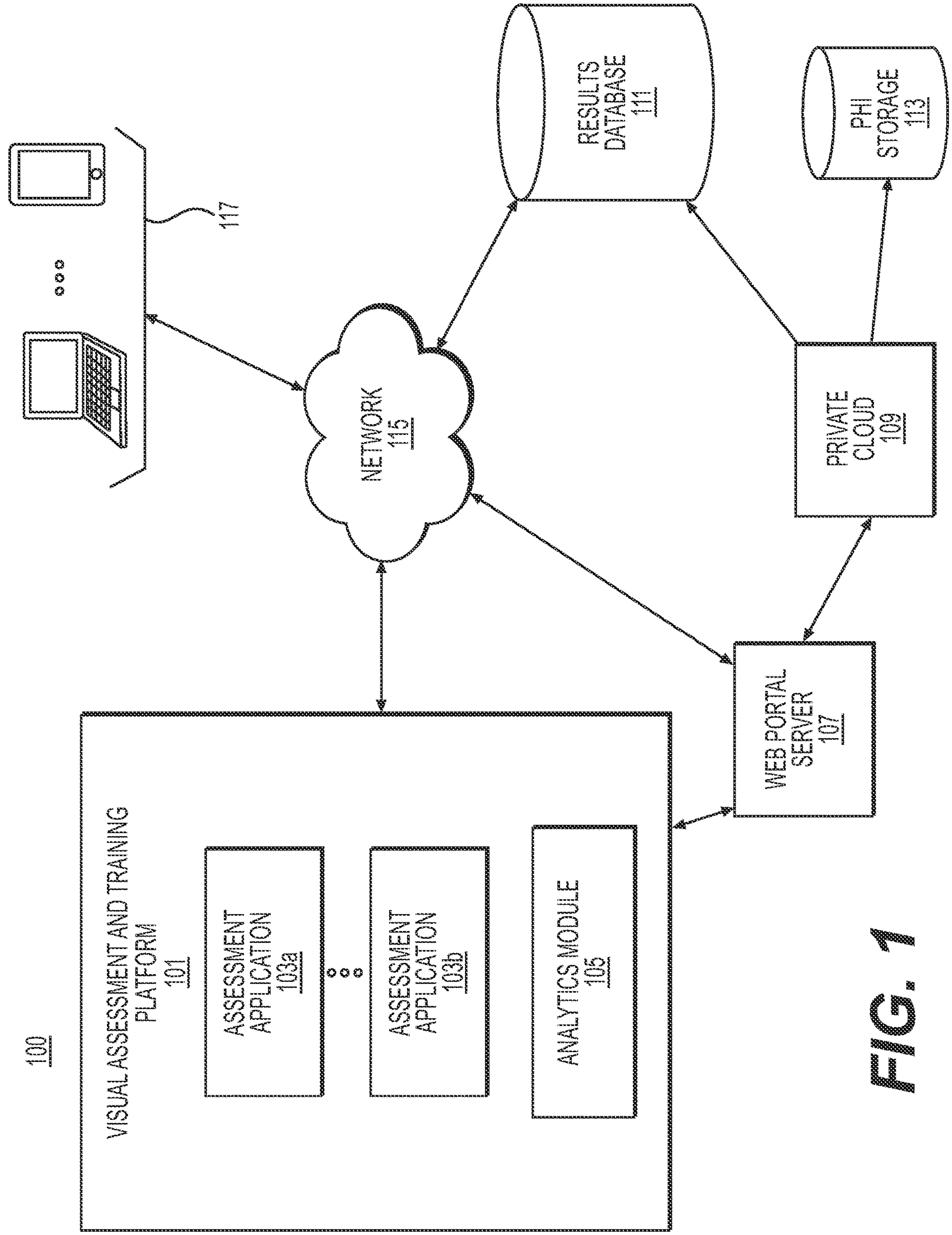
FIG. 1 is a block diagram of an exemplary eye evaluation system and web platform for hosting multiple human visual performance assessments, interpreting and evaluating user performance on the assessments, and providing recommendations to improve, maintain, or rehabilitate user visual performance, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

In view of the challenges and goals outlined above, systems and methods are disclosed for enabling communication between various visual assessment applications, the communication including user access to multiple visual assessment applications, compatibility in receipt of visual assessment data, data exchange between applications, and/or leveraging data analysis capabilities in sharing data. In particular, the systems and methods may include a visual assessment and training/therapy platform that manages or hosts multiple visual assessment applications. Visual assessments may include any evaluations of eye movement data, including assessments of a user's visual performance and/or assessments of a user's neurological state. Visual performance may encompass all measures of a user's vision, e.g., a user's visual ability (e.g., a static ability that may be predetermined by the user's genetic composition), a user's visual capacity (e.g., abilities of a user that may be flexible or abilities that may vary with practice, training, therapy, etc.), a user's visual status (e.g., a user's eye movement and neurological responses at a given point in time), a user's eye movement response as a result of a user's neurological function, etc. In other words, visual performance may refer to a user's eye movement being normal (e.g., associated with a usual, healthy individual), above normal (e.g., an expert, professional-level, or experienced athlete, vehicle driver, hunter, etc.), or impaired (e.g., due to injury or a neurological disorder). Exemplary neurological disorders may include, for instance, Parkinson's Disease, Autism, Attention Deficit Disorder, stroke, Cerebral Palsy, Multiple Sclerosis, Dementia, etc. A user's neurological state may encompass a user's neurological function at a given point in time, including a user's progression in gain or loss of neurological function related to eye movements and vision.

In one embodiment, the visual assessment and training/therapy platform may comprise an electronic application exchange. In one embodiment, the platform may receive any eye movement data, e.g., data collected from any eye tracking device. The platform may further convert received eye movement data for usage by any visual assessment application hosted by the platform. For one embodiment, the platform may analyze a set of foundational vision metrics, e.g., fixations, saccades, smooth movement, etc., to generate assessments of a user's health and visual performance. In other words, the platform may collect and analyze foundational vision metrics to generate conclusions on a user's visual performance, e.g., by way of outputs conveying a user's visual acuity or visual strength and/or outputs including a diagnosis or status of a neurological disorder.

In one embodiment, each visual assessment may exist as an algorithm. The platform may host the visual assessment, meaning the platform may integrate the algorithm into the foundational metrics of the platform. In other words, the platform may provide continuity between several visual assessments and their respective eye tracking collection mechanisms and calculations. The platform may further evaluate user performance across multiple visual assessment applications and provide recommendations for the user to improve, maintain, or rehabilitate his or her visual performance. Additionally, the platform may leverage data and analyses from multiple visual assessment applications to improve user performance evaluations and recommendations.

Users of the present embodiments may include any people desiring to assess and/or improve, maintain, or rehabilitate their health and wellness (e.g., in the form of detecting or diagnosing possible neurological impairment/disorder and/or evaluating or improving motor skills, cognition, and/or kinesiology. For example, users may include any individuals who perform physical activities that require observation and/or decision making ahead of physical and/or mental action. These users can include athletes, pilots, drivers, heavy machine operators, lab equipment technicians, physicians, law enforcement professionals, and/or any other individuals seeking performance enhancement or individuals involved in actions that require a cognitive process in order to respond more effectively and efficiently. Alternately or in addition, users may include individuals wanting to ensure that their vision is healthy. Alternatively or in addition, users may include learning or cognitively impaired individuals seeking to improve, maintain, or rehabilitate their mental and physical abilities.

Exemplary recommendations output by the presently-disclosed web platform may include suggesting that a user see a healthcare provider, providing a notification to a healthcare provider of a user's visual performance abilities/status (e.g., for a provider to monitor a user's disease status or progress from treatment), etc. the recommendations may include real-time reports that deliver assessment results and therapies/training based on the results. For instance, the reports may include graphical visualizations of granular and important data for a user and/or healthcare provider.

The presently-disclosed web platform may be used as a widely adopted diagnostics tool used by nearly all members of the general population, in a school screening context, as a home-administered consumer screening platform, as a government or local screening platform at a community facility (e.g., a pharmacy, clinic, prison, military post, etc.), as a healthcare-affiliated screening platform, etc.

Turning now to the figures, FIG. 1 is a block diagram of an exemplary eye evaluation system and environment 100 for hosting multiple human visual performance assessments, evaluating user performance on the assessments, and providing recommendations to improve, maintain, or rehabilitate user visual performance, according to an exemplary embodiment of the present disclosure. Eye evaluation system and environment 100 may comprise multiple computing systems and/or devices 117 configured to send and receive information from visual assessment and training platform 101, web portal server 107, and results database 111 over an electronic network 115. In one embodiment, various components of the eye evaluation system and environment 100 may be in direct local contact with one or more other components of the eye evaluation system and environment 100. In one embodiment, environment 100 may be run over an network-based, with various components of environment 100 running remotely or independently from one another. Alternately or in addition, environment 100 may run locally on a device or system, e.g., without Internet access.

It should be appreciated that eye evaluation system and environment 100 and/or visual assessment and training platform 101 may include any type or combination of computing systems, e.g., handheld devices, personal computers, servers, clustered computing machines, and/or cloud computing systems. Eye evaluation system 100 and/or visual assessment and training platform 101 may further include one or more peripheral devices, for example, button presses, joysticks, headsets, virtual reality consoles, etc. In one embodiment, eye evaluation system 100 and/or visual assessment and training platform 101 may be an assembly of hardware, including a memory, a central processing unit ("CPU"), and/or one or more user interfaces. The memory may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. The CPU may include one or more processors for processing data according to instructions stored in the memory. The functions of the processor may be provided by a single dedicated processor or by a plurality of processors. Moreover, the processor may include, without limitation, digital signal processor (DSP) hardware, or any other hardware capable of executing software. The one or more user interfaces may include any type or combination of input/output devices, such as a display monitor, touchpad, touchscreen, microphone, camera, keyboard, and/or mouse, or other interface.

As shown in FIG. 1, visual assessment and training/therapy platform 101 may include a plurality of visual assessment applications (e.g., assessment applications 103*a*-103*n*). The visual assessment and training/therapy platform 101 may further include an analytics module 105. In some instances, the visual assessment and training/therapy platform 101 may include multiple analytics modules. For example, one or more assessment applications (e.g., assessment application 103*a* or assessment application 103*n*) may include its own analytics module or be associated with a particular analytics module. In one embodiment, the assessment applications 103*a*-103*n* and the analytics module 105 may have distinct hardware configurations. For example, the applications 103*a*-103*n* may have various configurations and be associated with one or more application programming interfaces (APIs). In one embodiment, the visual assessment and training/therapy platform 101 may include an operating system-based host machine, and the host machine may house the assessment applications 103*a*-103*n* and analytics module 105. In another embodiment, the visual assessment and training/therapy platform 101 may include an Internet platform, housing and/or communicating with assessment applications 103*a*-103*n* and an analytics module 105. One or more assessment applications 103*a*-103*n* and/or the analytics module 105 may run remotely, or at least in part inside the visual assessment and training/therapy platform 101. In one embodiment, the visual assessment and training/therapy platform 101 may further receive or process data from one or more eye tracking devices.

In one embodiment, the visual assessment and training/therapy platform 101 may be operated or accessed by consumers (not shown). For example, consumers may access assessment applications 103*a*-103*n* via a web portal server 107. The web portal server 107 may provide user interfaces for consumers to select one or more assessment applications 103*a*-103*n* in order to assess their vision. The assessment applications 103*a*-103*n* may each administer one or more visual assessments, e.g., as described in U.S. Pat. No. 8,864,310 filed Mar. 14, 2013, the entire disclosure of which is hereby incorporated by reference in its entirety.

The web portal server 107 may further permit users to access reports detailing results of their visual assessments. In one embodiment, the web portal server 107 may generate all or part of such reports. In another embodiment, the analytics module 105 may generate the report content, while the web portal server 107 may store and display reports to the user. In some embodiments, the web portal server 107 may further provide user access to the visual assessment and training/therapy platform 101. In one embodiment, the analytics module 105 and/or the web portal server 107 may communicate with private cloud 109. The private cloud 109 may receive raw or processed user data, identify data containing information deemed as Protected Health Information (PHI), and transfer the PHI data to PHI storage 113. In one embodiment, private cloud 109 may host infrastructure for a testing platform, APIs, and storage for intake of raw or processed data, analytical APIs, and storage of computed data. The private cloud 109 may also host the web portal server 107 and present raw data and/or computed metrics, scores, analytics, visualizations, etc.

In one embodiment, the results database 111 may store results that do not contain PHI data, meaning the results database 111 may store and aid in collective analysis of a plurality of users. The visual assessment and training/therapy platform 101 may use data from the results database 111 to improve the data collection and/or analytics of the visual assessment and training/therapy platform 101 (e.g., using machine learning from data stored in the results database 111).

Network 115 may include the Internet, a content distribution network, or any other wired, wireless, and/or telephonic or local network. Visual assessment and training/therapy platform 101, web portal server 107, the results database 111, and various user and/or administrator devices 117 may communicate with each other via network 115.

In one embodiment, users may access the web portal server 107 via network 115 and one or more devices 117. Devices 117 may include any type of electronic device configured to send and receive data, such as websites and multimedia content, over electronic network 115. For example, devices 117 may include one or more mobile devices, smartphones, personal digital assistants ("PDA"), tablet computers or any other kind of touchscreen-enabled device, a personal computer, a laptop, and/or server disposed in communication with electronic network 115. Each of the devices of devices 117 may have a web browser and/or mobile browser installed for receiving and displaying electronic content received from one or more of web servers (e.g., web portal server 107) affiliated with the eye evaluation system 100. Each of the one or more devices 117 may include client devices that may have an operating system configured to execute a web or mobile browser, and any type of application, e.g., a mobile application.

In one embodiment, devices 117 may include any type of device configured to collect and send useful information to the visual assessment and training/therapy platform 101 for evaluating user performance on the assessments, and providing recommendations to improve, maintain, or rehabilitate user visual performance. For example, devices 117 may include eye tracking devices, which may include computers/mobile phones having eye-tracking capabilities and/or devices designated specifically for eye-tracking. Exemplary devices 117 may include one or more of: wearable cameras and/or remote cameras, one or more sensors, such as a heat sensing device, a GPS device, an RFID device, or any other sensors that aid in the detection of human eyes, the location and/or orientation of the human eyes, detection of body position of the user, and/or the location and/or orientation of the wearable cameras and/or remote cameras. In one embodiment, devices 117 may include, but are not limited to webcams, video cameras, remote eye trackers, mobile phones, tablet computers, spectacles, visors, helmets, implanted devices, and/or contact lenses. In one embodiment, one or more of devices 117 may be configured with network adapters to communicate information to the visual assessment and training/therapy platform 101 and/or web portal server 107 over network 115. Alternatively, or additionally, one or more devices 117 may be configured to transmit and receive information from visual assessment and training/therapy platform 101 and/or web portal server 107 directly over a local connection.

Devices 117 may be owned and operated by an operator of one or more of: visual assessment and training/therapy platform 101, a user taking an assessment, and/or an outsourced third party, e.g., an eye tracking specialist. For example, people or organizations desiring to have their eyes (or members' or employees' eyes) evaluated may use devices 117 to send and receive information from the web portal server 107. In one embodiment, the visual assessment and training/therapy platform 101 may receive various user information from the web portal server 107 and/or devices 117. Exemplary user information may include one or more of: registration information, demographic information (e.g., age, sex, location, etc.), clinical history information, prescription or past medication information, biometric information, eye information, activity information, etc.

In one exemplary use case, devices 117 may include a user's mobile phone. The user may log into the web portal server 107 via the mobile phone (of devices 117) and access one or more assessment applications 103*a*-103*n*. The visual assessment and training/therapy platform 101 may receive some user information from the mobile device 117 (e.g., user location, age, billing information, etc.) and receive other user information from the web portal server 107 (e.g. prescription or past medical information, past activity/eye assessment information, subscription level dictating user access to visual assessments, etc.). Following the completion of a user's assessment(s) and analysis, the visual assessment and training/therapy platform 101 may store or provide access to assessment results to the user via the web portal server 107. For example, the web portal server 107 may include reports of the results of the assessment(s), as well as providing training or therapy to improve, maintain, or rehabilitate the user's vision. The web portal server 107 may further provide tracking of the user's assessment(s) and/or progress, past and present. For instance, a user may communicate with the web portal server 107 via a device 117 to view his or her assessment results and/or vision improvement training/therapy regimen. Alternately or in addition, a user may perform an assessment via the web portal server 107. For example, exemplary assessment application 103*a* may include a set of stimuli presentation and eye scoring methods. The web portal server 107 may display a stimuli presentation to the user, receive eye-tracking information from one or more devices 117, and convey the eye-tracking information to the visual assessment and training/therapy platform 101. The visual assessment and training/therapy platform 101 may analyze the received information, determine one or more recommended training tasks, reports, etc., and provide the determined one or more recommended training/therapy tasks, reports, etc. to the user via the web portal server 107.

Figure 2A:
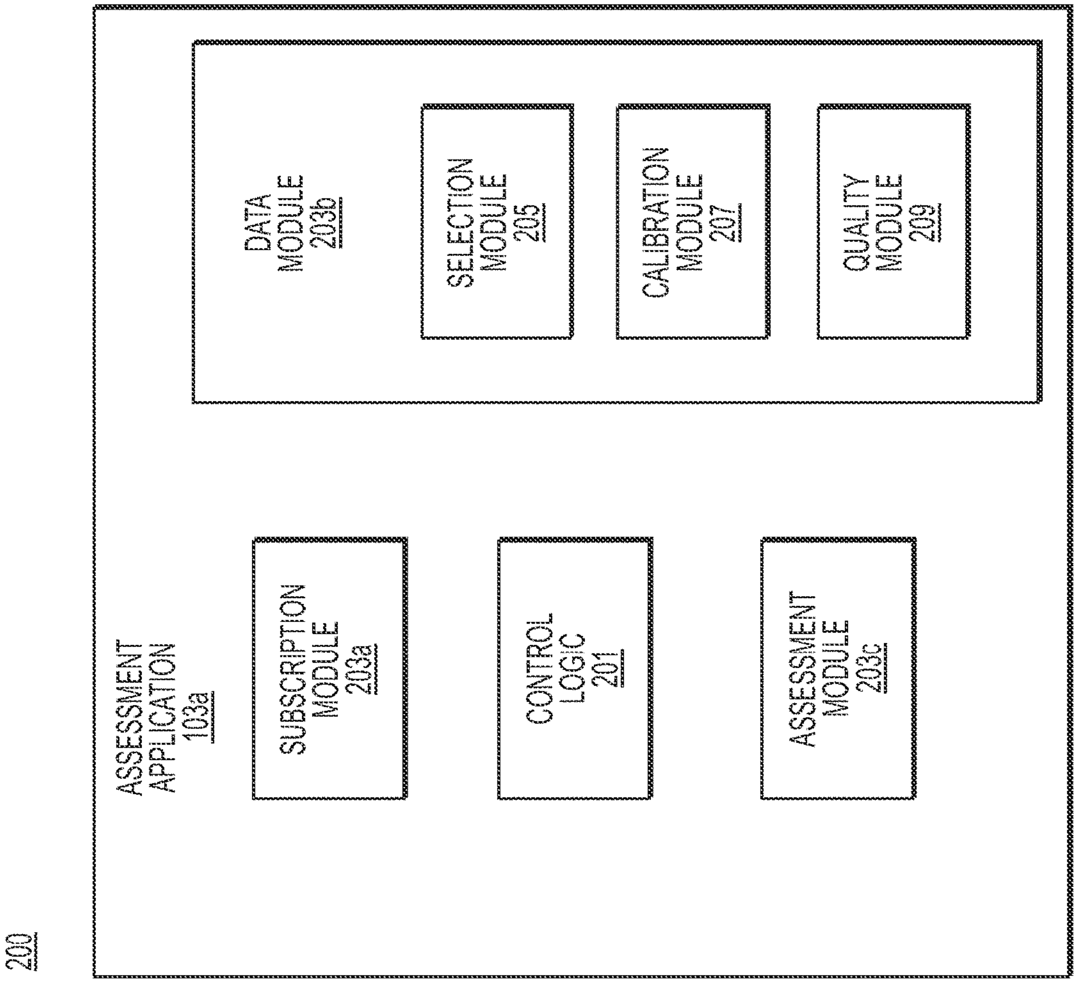
FIG. 2A is a block diagram of an exemplary assessment application for administering a visual assessment and collecting data on a user's performance on the visual assessment, according to an exemplary embodiment of the present disclosure.

FIG. 2A is a block diagram of an exemplary model 200 of an assessment application 103*a* for administering a visual assessment and collecting data on a user's performance on the visual assessment, according to an exemplary embodiment of the present disclosure. As shown in FIG. 2A, exemplary assessment application 103*a* may include a control logic 201, a subscription module 203*a*, a data module 203*b*, and an assessment module 203*c*. In one embodiment, the data module 203*b* may include various functions for processing received data. Exemplary functions are represented by the illustrated modules, including a selection module 205, calibration module 207, and quality module 209. Control logic 201 may direct the functions and interactions among the various modules.

The subscription module 203*a* and control logic 201 may communicate with web portal server 107 to determine a user's subscription to one or more assessment applications 103*a*-103*n*. For example, various subscriptions may dictate the user's access to vision assessments, reports, and/or training/therapy regimens. For instance, a user with a full subscription may access any of the various assessment applications 103*a*-103*n* hosted by the visual assessment and training/therapy platform 101. Other subscription levels may be associated with subsets of the assessment applications 103*a*-103*n* or analyses/reports respective of various assessments. Subscriptions may be user-based. For instance, a user may participate in an employer or health care program that may dictate a set of vision assessments for desk jobs. In another instance, a user may be an athlete, and his or her subscription level may include vision assessments particularly tailored to the sport practiced by the athlete. The subscription module 203*a* may determine whether a particular assessment application 103*a* is prompted to be available and/or run, given a user's subscription.

In one embodiment, the data module 203*b* and control logic 201 may communicate with one or more devices 117 and/or web portal server 107 to receive data regarding a user's visual assessments. For example, data module 203*b* may prompt data collection for a visual assessment that may be administered via assessment module 203*c*. Data module 203*b* may further select, calibrate, and/or perform a quality assessment of collected data of a visual assessment, using selection module 205, calibration module 207, and quality module 209, respectively.

In one embodiment, selection module 205 may select an eye tracking capability to use for a particular assessment (e.g., of assessment module 203*c*). For instance, various eye trackers may have different tracking ranges and various visual assessments may necessitate different tracking ranges. A tracking range may include a visual field of recording, meaning a measure of how far to the side a user may look for the eye tracker to still obtain data. In one embodiment, a head box may include a volume relative to an eye-tracker in which a user may move without compromising the quality of recording data. Eye trackers with larger tracking ranges may be desired for some assessments, while some assessments may be completed within any range of tracking ranges. Selection module 205 may detect and select, of devices 117, an eye tracker to engage for the assessment of assessment module 203*c*. The assessments that may be administered by control logic 201 and assessment module 203*c* may be one or more of the assessments as described in U.S. Pat. No. 8,864,310 filed Mar. 14, 2013, the entire disclosure of which is hereby incorporated by reference in its entirety.

In one embodiment, calibration module 207 may map an output from the selected eye tracker (e.g., of devices 117) to a gaze point of the user. For example, calibration module 207 may prompt a calibration test involving a series of cues (e.g., a circular dot) displayed on a user interface. The calibration module 207 may receive data including a user's response to the cues and compare such received data to the positions of the cues. In other words, calibration module 207 may validate the received user data by determining whether the estimated/received eye position(s) of the user are close to the known position(s) of the cues. For example, the assessment application 103*a* may receive data collected at a 120 Hz sampling rate, where raw eye data points are collected every 8.3 milliseconds. (In various scenarios, exemplary sampling rates may vary from 30 Hz to thousands of Hz.) The calibration module 207 and control logic 201 may receive each data point identified as a timestamp and run "x, y" coordinates against a calibration formula to determine if discrepancies between the received data and the known positions of the cues fall within an acceptance level. The acceptance level may be specific to the visual assessment of assessment module 203*c*, the device 117, the user, the user's subscription, etc. If the discrepancies fall within the acceptance level, the calibration module 207 and control logic 201 may prompt assessment module 203*c* to start a visual assessment. During the assessment, the calibration module 207 may interpolate between calibrated landmarks (e.g., from the cues) to determine where a user's eye is fixating on a user interface. The functions of calibration module 207 are described in more detail in FIG. 6B.

In one embodiment, calibration module 207 may further determine which received eye movement data to use in building a calibration model for adjusting displays/prompts of the assessment of the assessment module 203*c*. For instance, calibration module 207 may consider saccadic latency in building the calibration module. Saccadic latency may include the time from a stimuli presentation (e.g., on a user interface) to the start of a saccade. When a calibration point on a screen changes position, there may be a delay before the human brain reacts and initiates eye movement. Calibration module 207 may account for saccadic latency in building the calibration test by determining the quantify, frequency, and location of calibration point cues that may achieve accurate and precise results. Calibration module 207 may further take into account the length of the calibration test, as well as the age/medical history of the user, whether the user has previously taken the assessment (e.g., using the same eye tracker), calibration information from other users or assessments, etc.

In one embodiment, quality module 209 and control logic 201 may govern the quality of received data. For example, quality module 209 and control logic 201 may govern the sampling frequency, latency, accuracy, and precision of data collected for an assessment. For example, a sampling frequency may depend on what an assessment desires to detect or measure and the desired precision of results. The faster and more specific the assessed eye movements, the higher the desired sampling rate may be. In one instance, latency may include a delay between the display of a cue and a user's eye motion in response to the cue. Latencies may arise from a variety of sources, e.g., different stimuli, eye trackers, eye movements, computer refresh rates, etc. In one embodiment, quality module 209 and control logic 201 may filter data, thus decreasing variations that may derive from sources other than eye movements themselves. There are many types of filters, each with varying effects on subsequent analysis, especially event detection, e.g., fixations, saccades, etc. In one case, filtering may occur while data is being recorded (after calibration) (e.g., by an eye tracking device). For instance, each eye movement sample may be filtered for noise and artifact removal. Filtering in real time may case a latency. Alternately or in addition, filtering may occur in a software development kit (SDK) (e.g., by control logic 201 and quality module 209 which may or may not be part of an eye tracking device). Software filtering may be used to calculate both velocity and acceleration data. For example, velocity may be calculated by numerical differentiation, where a user's eye velocity may be calculated by an angular distance between two adjacent pairs of samples and multiplying the angular distance by the sampling frequency of the eye tracker. For instance, velocity may be reported as degrees of visual angle per second. Acceleration data may be calculated by calculating a velocity between two adjacent pairs of samples and multiplying the velocity by the sampling frequency of the eye tracker. Filters may be selected and/or changed based on the assessment (e.g., of assessment module 203*c*) and the metrics desired (including the metric and the quality/accuracy/precision of the metric). For example, filter selection or change may include accounting for a filter type (e.g., Butterworth filter) and/or a filter order (e.g., a filter of Order 1, 2, 3, 4, etc.).

The control logic 201 and quality module 209 may further determine or select filer order(s) based on the assessment and metrics desired from the assessment. In one embodiment, control logic 201 and quality module 209 may customize filter design for each assessment. For example, customized filter design may include two "filtering" algorithms: one to smooth a data set to remove noise and artifacts, and another to extract velocity information from eye tracking samples. The smoothing and velocity filters may be tuned for each assessment, for example, filter order may be selected for each assessment. The order of the filter may determine the amount or type of raw data to filter out. The higher the order of the filter, the more data that may be lost, increasing the difficulty of classifying smaller eye movements. In some cases, control logic 201 and quality module 209 may employ a low order in order to allow for more variability in the data. For example, in an assessment that desires the ability the classify saccades, fixation, and smooth pursuits, a respective quality module 209 and control logic 201 may select a low order filter. An assessment that only evaluates fixations, for instance, may employ a higher order filter since the assessment does not desire as much granularity with its analysis. In such cases, filters that remove smaller eye movements may improve the assessment's analysis, e.g., analysis involving classifications algorithms for eye movements.

In one embodiment, control logic 201 and quality module 209 may also employ a data integrity check before filtering. For example, control logic 201 and quality module 209 may perform an initial check to ensure that not too many samples are lost and that samples may be used for future analysis. The data integrity check may include a continuous data loss check for large gaps in time between valid samples. Another check may include evaluating overall data loss. The control logic 201 and quality module 209 may also employ a cleaning filter, smoothing filter, velocity filter, etc. For instance, a cleaning filter may process lost data out of a set of received raw data. Data loss may include samples reported as invalid by an eye tracker. Data loss may occur when glasses, contact lenses, eyelashes, or blinks prevent an eye image to be reliably captured, detected, or tracked. Removing lost data may help prevent the lost data from being interpreted as large jumps or high velocity eye movements in later analysis. Alternately or in addition, the control logic 201 and quality module 209 may monitor data loss while receiving raw data and provide a notification to a user when received samples drop below a predetermined threshold. The threshold may be different for each assessment, eye tracker, etc. An exemplary notification may prompt a user to check various impediments to data collection and to re-test.

A smoothing filter may reduce noise and other artifacts (e.g., small eye movements) in raw data. A velocity filter may extract the velocities of each gaze position over the duration of an assessment. For example, a filter circuit may refer to how many times (e.g., orders) data may be attenuated. Different types of filter circuits may involve different responses to changing frequency. A filter may be characterized by its cutoff frequency and/or rate of frequency roll-off. At the cutoff frequency, a filter may attenuate an input power by half or 3 dB. The order of a filter may determine the amount of additional attenuation for frequencies higher than the cutoff frequency.

In one embodiment, assessment module 203*c* and control logic 201 may generate the prompts for one or more visual assessments of the assessment application 103*a*. In one embodiment, the assessment of assessment module 203*c* may dictate the processes of data module 203*b*. For example, eye tracker selection, data calibration, and data quality processing may be tailored to the assessment of assessment module 203*c*.

Figure 2B:
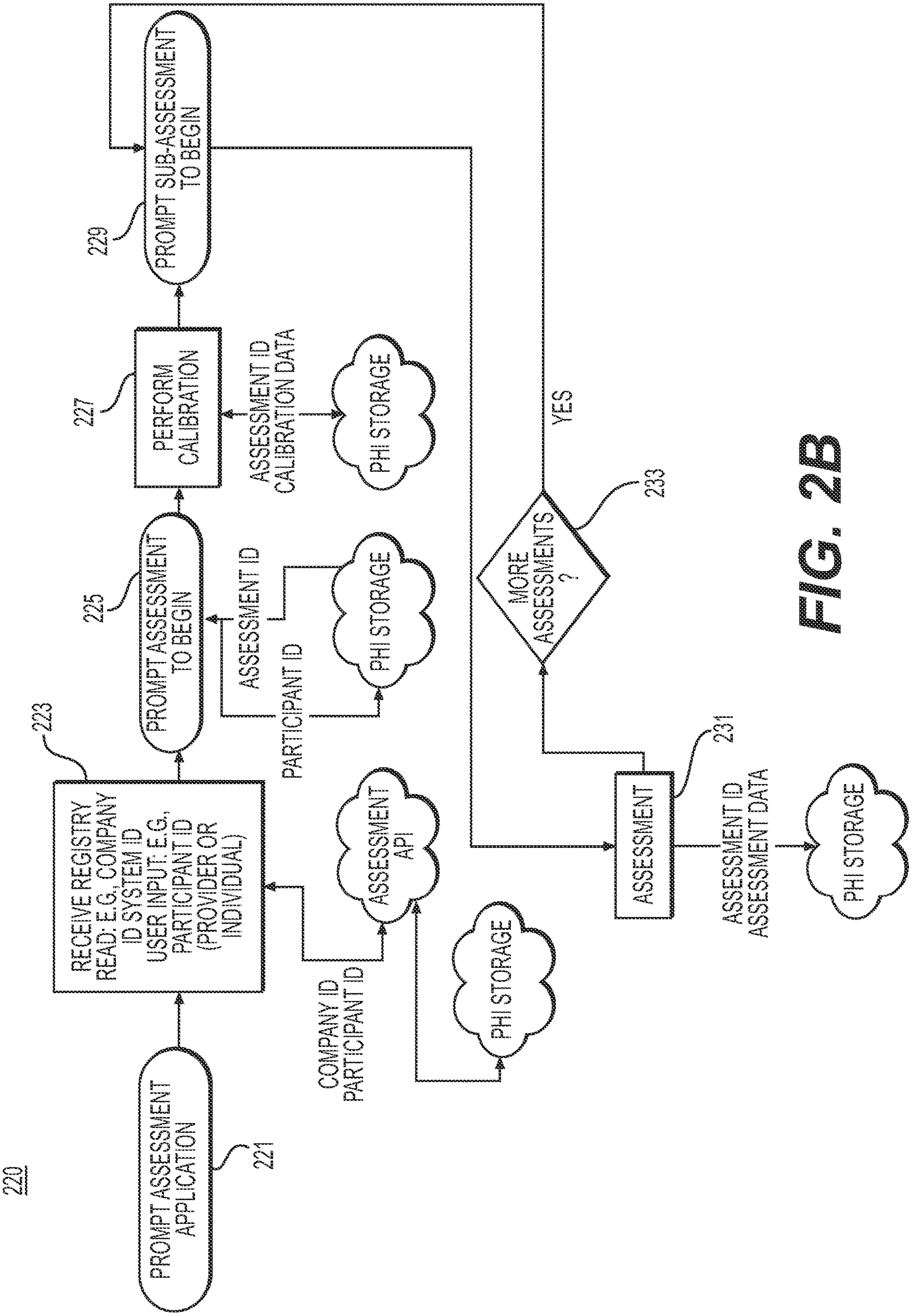
FIG. 2B is a flow diagram of an exemplary method for performing a visual assessment using one or more assessment applications, according to an exemplary embodiment of the present disclosure.

FIG. 2B is a flow diagram of an exemplary method 220 for performing a visual assessment using one or more of the assessment applications 103*a*-103*n*, according to an exemplary embodiment of the present disclosure. As shown in FIG. 2B, method 220 may involve control logic 201 prompting an exemplary assessment application 103*a* (step 221). Step 223 may include receiving user information. In one embodiment, user information may include registration information, e.g., from a web porter server 107 registry. Registration information may include a company identifier (ID) (e.g., when subscriptions are part of employment or health plans), or a system ID (e.g., from one or more devices 117). For example, registration information may include information previously generated and stored on a local device 117. User information may also include user input, e.g., the assessment application 103*a* may prompt a user or an assessment administrator to enter a participant ID (from login information). The participant ID may include a provider ID or an ID for the individual user. The user information may further include context information, information on the user's health, etc. Context information may include information on the user's location, device data, device or system compatibility (e.g., with the assessment application 103*a*), billing information, etc. Information on the user's health may include data associated with past assessments, the user's prescription, the user's medical history, the user's biometric data, etc.

In one embodiment, a portion of data/metadata may be stored at an assessment API and designated data repository (e.g., PHI storage 113). For example, an assessment application programming interface (API) may receive user registration information. At least a portion of the registration information may then be stored in PHI storage 113. In one embodiment, the assessment API may search the PHI storage 113 to see if the received registration information exists. If the registration information exists, the PHI storage 113 may provide a participant ID. If the registration information does not exist, the PHI storage 113 may create a new entry or participant profile.

In one embodiment, step 225 may include initiating the start of the assessment of exemplary assessment application 103*a*. In one embodiment, the assessment may be identified by an assessment ID, and said assessment ID may be stored with a participant ID in PHI storage 113. In one embodiment, step 227 may include calibrating data received from the assessment (e.g., of step 225). In one instance, the calibration data may be associated with the assessment ID and stored in PHI storage 113. In one embodiment, step 229 may include identifying whether more assessments exist (e.g., sub-assessment(s)). For example, a single exemplary assessment application 103*a* may include multiple visual assessments for a user to complete. In another example, several assessment applications 103*a*-103*n* may be associated, either since they were created to be related applications, since the user selected multiple assessment applications 103*a*-103*n*, because a subscription dictates a certain combination of assessment applications 103*a*-103*n*, etc. Step 229 may include selecting or determining an assessment application related to assessment application 103*a*. Steps 231 and 233 may include prompting the user to complete one or more of the related assessments until all of the user's assessments are completed. Assessment data may be stored with the assessment ID in PHI storage 113. In one embodiment, the exemplary assessment application 103*a* may pass a session token to the web portal server 107, for the web portal server 107 to generate and/or display assessment report(s) to the user. The assessment data my include raw data from the assessments and/or analytics based on the data.

Figure 3:
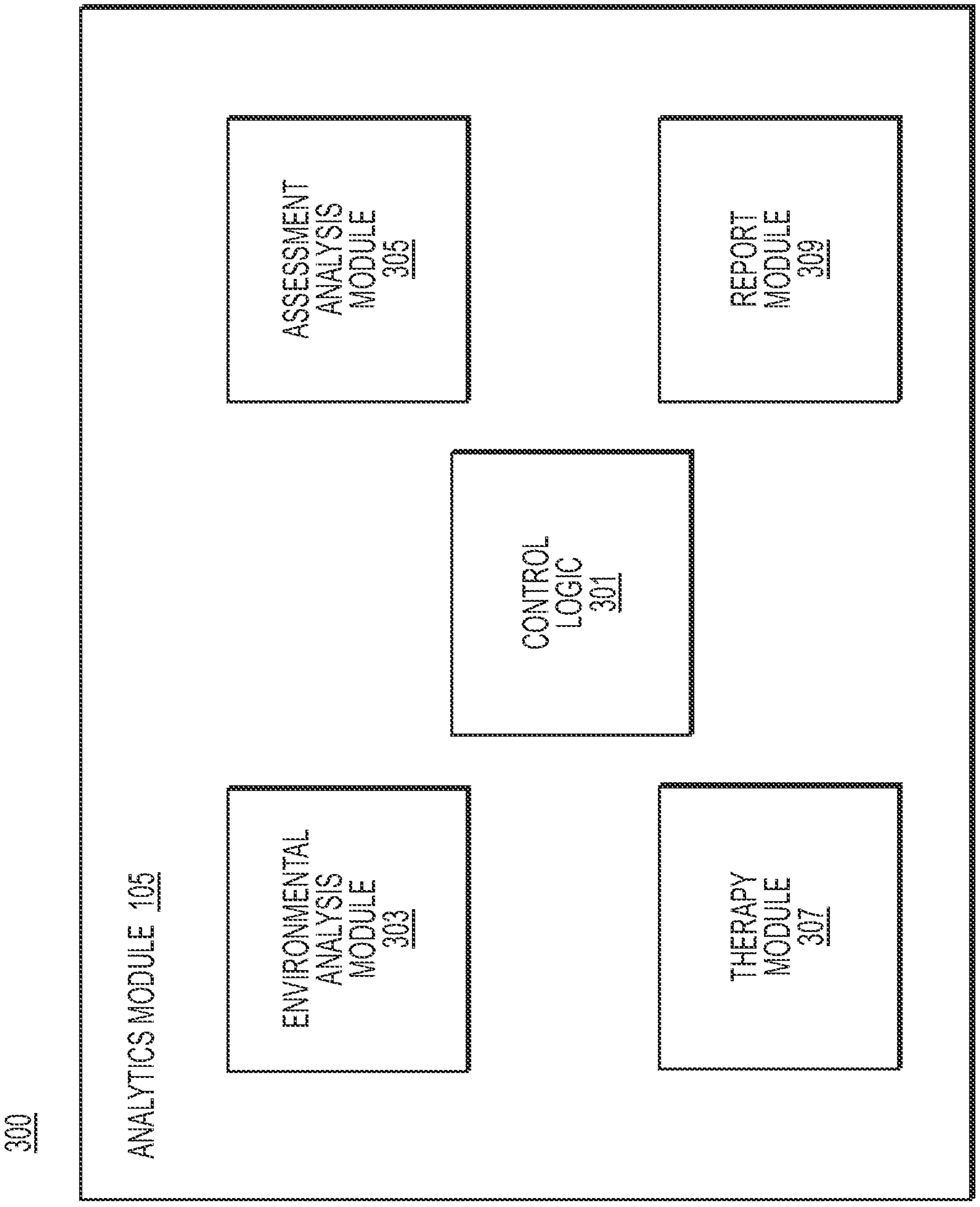
FIG. 3 is a block diagram of an exemplary analytics module for assessing a user's vision, according to an exemplary embodiment of the present disclosure.

FIG. 3 is a block diagram of an exemplary model 300 of analytics module 105 for assessing a user's vision, according to an exemplary embodiment of the present disclosure. In one embodiment, model 300 may reflect a system that may be implemented by the visual assessment and training/therapy platform 101, for communicating over network 115 (e.g., using any suitable modem, wireless adapter, etc.). As shown in FIG. 3, analytics module 105 may include a control logic 301, an environmental analysis module 303, an assessment analysis module 305, a therapy module 307, and a report module 309. Control logic 301 may direct the functions and interactions among the various modules.

In one embodiment, the control logic 301 and environmental analysis module 303 may receive information regarding one or more contextual/environmental factors that may influence an assessment or an assessment analysis. Exemplary environmental factors may include one or more of eye tracker parameters or specifications, user health information, user age, etc. In one embodiment, the environmental factors may be received from the web portal server 107 and/or one or more devices 117.

The control logic 301 and assessment analysis module 305 may dictate the metrics that are to be evaluated from user assessment performance data (e.g., as collected from an eye tracker and/or as processed by an assessment application 103*a*). Metrics may be divided into multiple levels based on an amount of analysis that goes into calculating the metrics. For example, the control logic 301 and assessment analysis module 305 may recognize four levels of metrics: level 1 metrics (including detection of oculomotor events), level 2 metrics (including formulas and user-specific metrics), level 3 metrics (including user-to-group comparisons), and level 4 metrics (including group norms).

Level 1 metrics may be the most basic level of metrics, providing foundational understating of received raw data based on science, stimuli, and demographics. For instance, level 1 metrics may identify oculomotor events (e.g., fixations, saccades, smooth pursuits, etc.) in raw data. A fixation may refer to a "stopping point," detected using a dispersion/duration criterion, a velocity/acceleration criterion, or manual detection. Dispersion/duration may refer to temporally adjacent data samples that may be located within a spatially limited region for a minimum duration. A velocity/acceleration criterion may include identifying fixations as contiguous portions of gaze data, where gaze velocity does not exceed a predefined threshold. Detecting saccades may include identifying periods, in received user assessment data, where the user's eyes "move fast." Such movement may be defined by predetermined velocity and acceleration thresholds that may be specific to an assessment. Eye movement that exceeds the predetermined velocity and acceleration thresholds may be identified as saccades.

Smooth pursuit eye movements may include eye movements in which a user's eyes follow an object, e.g., by keeping the object in the fovea of the eye. The control logic 301 and assessment analysis module 305 may detect a smooth pursuit using velocity of the stimuli (e.g., a dot displayed during an assessment) and a rate of change in velocity of a user's eye movement. The control logic 301 and assessment analysis module 305 may also detect smooth pursuits by determining that sequential samples form a direction/pattern that mirrors that of assessment stimuli. The control logic 301 and assessment analysis module 305 may further detect smooth pursuits by accounting for distance from stimuli created by bandwidth areas of interest. Bandwidth areas of interest may include data observed in relation to a particular variable (e.g., an area of a screen, a stimuli, etc.).

Calculating other level 1 metrics may include detecting microsaccades, glissades, drifts, tremors, and/or square-wave jerks. Microsaccades may include small fast eye movements that quickly bring the eye back to an original position. Glissades may include a post-saccadic movement where an eye "wobbles" before maintaining a position. Drifts may include slow eye movements that may take an eye away from a center of fixation. Tremors may include a small movement of frequency around 90 Hz that may be imprecise muscle control. Square-wave jerks may include involuntary, conjugate, saccadic intrusions that may take an eye off a visual target and then back to the target again.

Obtaining level 1 metrics may include filtering raw data to obtain valid calculations or identification of oculomotor events. Determining level 1 metrics may further involve classification of eye movements using ternary eye movement classification. Determining level 1 metrics may also include separating artifacts from user eye movements. Artifacts may occur when data samples report high velocity movement that physically may not be derived from real movement of a user's eye. Artifacts may include consecutive data samples that do not conform to any known eye movement event. If a received assessment data set has a high percentage of artifacts, the data may be a poor quality data set that should not be used for further analysis. Artifacts may also reveal faulty or inappropriate implementations of algorithms.

Level 2 metrics may determine specific outcomes from received data set(s), e.g., percentage of time in smooth pursuit eye movement. In one embodiment, level 2 metrics may take base calculations oculomotor data (e.g., from level 1 metrics) and further create groups of data that signify an event or outcome. In one embodiment, level 3 metrics may make calculations across groups of data (e.g., groups of data built from level 2 metrics). An exemplary calculation may include a smooth pursuit percentage for a particular user compared to that of one or more other users. The groups of data may be comprised of performance data from users that have taken the same assessment, or a different assessment.

In one embodiment, level 4 metrics may be used to develop norms, further outputs, and specifications of data. Level 4 metrics may include conclusions or inferences based on tests and user populations, e.g., a conclusion that there is a significant difference in visual performance between users aged 20-45 and users aged 46-70 for a specific assessment.

In one embodiment, control logic 301 and therapy module 307 may determine or select a training or therapy regimen for a user, based on the metrics determined by assessment analysis module 305. In one embodiment, control logic 301 and report module 309 may generate reports for a user, showing the user one or more performance metrics and/or displaying one or more recommendations for improving, maintaining, or rehabilitating his/her visual performance. Exemplary reports or displays of reports may be found at FIGS. 8-13. Training or therapy may include any exercises that may improve, maintain, or rehabilitate a user's visual performance (e.g., stimuli for a user to follow objects in a smooth fashion, identifying differentiators on objects (e.g., numbers on a ball), etc.). The training or therapy may be delivered in a physical environment, on a computer, etc.

Figure 4:
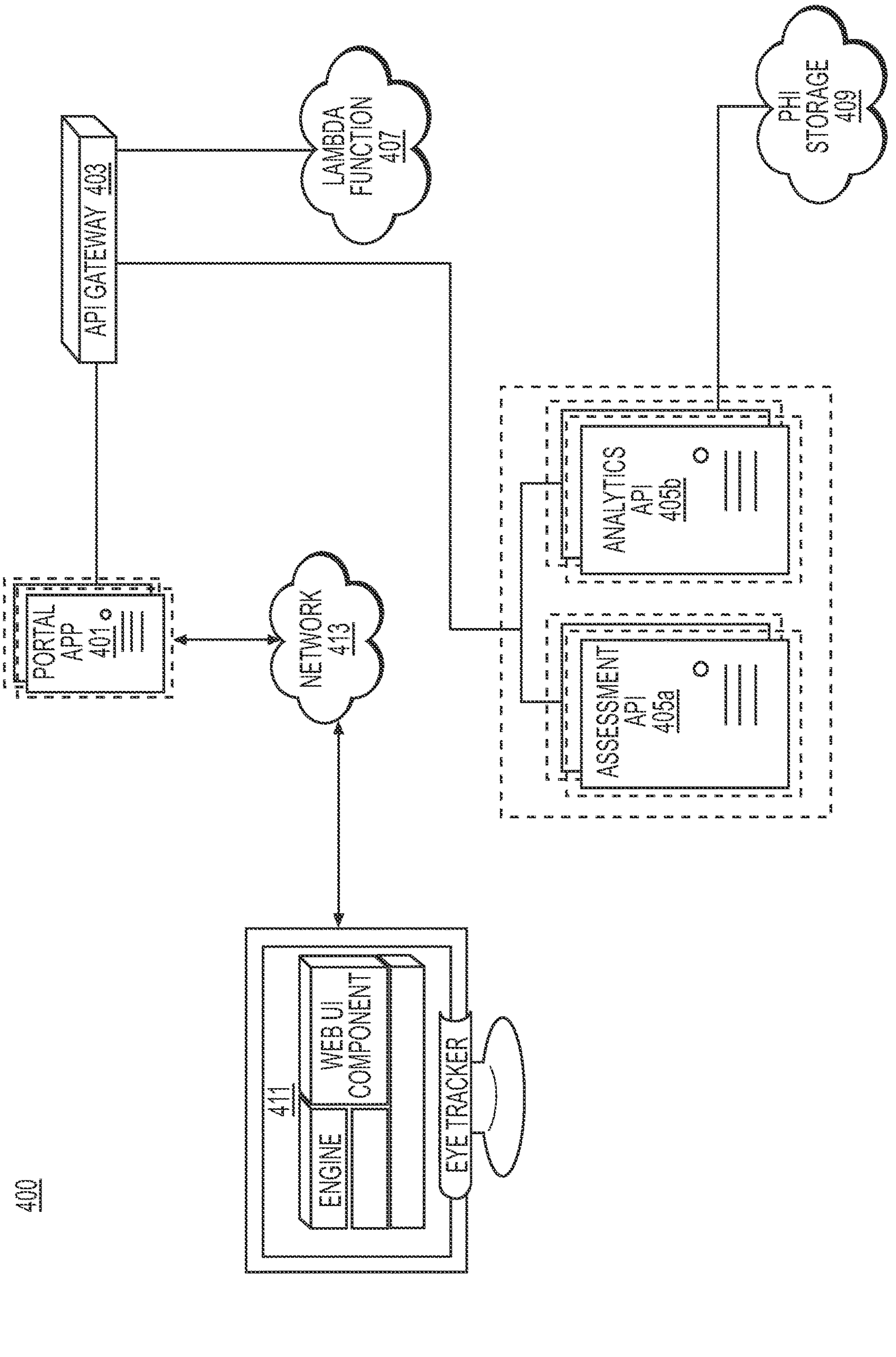
FIG. 4 is a block diagram of an exemplary eye evaluation system and web platform for hosting multiple human visual performance assessments, according to an exemplary embodiment of the present disclosure.

FIG. 4 is a block diagram of an exemplary eye evaluation system 400 for hosting multiple visual assessments, evaluating user performance on the assessments, and providing recommendations to improve, maintain, or rehabilitate user visual performance. FIG. 4 is an exemplary version of the system 100 of FIG. 1. As shown in FIG. 4, system 400 may include a portal application 401 connected to an API gateway 403. The portal application 401 may handle the main flow of assessments, e.g., by displaying a series of user interfaces permitting a user to either: select one or more assessments, take the one or more assessments, and/or retrieve reports associated with at least one of the one or more assessments. By displaying one or more assessment user interfaces (e.g., comprising a stimuli presentation), the portal application 401 may also collect a user's assessment performance data. For example, the user may interact with displays from the portal application 401 to complete an assessment. This way, the portal may receive data including the user's performance on an assessment.

In one embodiment, the API gateway 403 may house the one or more assessments. For example, the API gateway 403 may include at least one assessment API 405*a* and at least one analytics API 405*b*. In one embodiment, assessment API may be associated with one or more respective applications (e.g., assessment applications 103*a*-103*n*). In one embodiment, analytics API 405*b* may be associated with at least one application (e.g., analytics module 105), which may analyze user performance results of one or more visual assessments of assessment API 405*a*. In one embodiment, the assessment API 405*a* may request and process data on the user's performance on an assessment. For example, the assessment API 405*a* may determine a selection of data specific to the assessment of the respective assessment API, calibrate the data, and process the data for data quality. The analytics API 405*b* may analyze data received from the portal application 401 and/or data processed by the assessment API 405*a*. For example, the analytics API 405*b* may analyze received performance data to assess the user's vision. The analytics API 405*b* may further generate (or provide information to generate) one or more reports which the user may access through the portal application 401.

In one embodiment, the API gateway 403 may include a lambda function 407. In one embodiment, the lambda function 407 may assess and compare data across multiple users and improve analytics for the at least one analytics API 405*b*. For example, the analytics API 405*b* may review the data for a single user. Lambda function 407 may collectively analyze the data received from multiple users and update metrics or analytics of the at least one analytics API 405*b* with the collective analysis. In one embodiment, PHI storage 409 may store user PHI information such that the data collectively analyzed by the lambda function 407 is anonymous, e.g., free of user identification information.

In one embodiment, system 400 may include at least one eye tracker computing system 411. Eye tracker computing system 411 may include any device with eye-tracking capabilities or a designated eye-tracking device. In one embodiment, eye tracker computing system 411 may include an engine and/or a web user interface (UI) component. In one embodiment, as described before, the portal application 401 may directly receive user assessment performance data. In another embodiment, a user may complete at least a portion of an assessment presented using a web UI component of the eye tracker computing system 411. The engine may receive and process the user's performance data, and the portal application 401 may receive the user's performance data from the eye tracker computing system 411.

In one embodiment, each assessment available through the API gateway 403, may have its own respective eye tracker computing system 411. For example, the assessment API 405*a* and/or analytics API 405*b* may be configured to receive and process data specific to a specific eye tracker computing system 411. The portal application 401 may present reports on any or all of the assessments available through the API gateway 403, regardless, of their respective data collection sources and/or data processing means.

In one embodiment, network 413 may include the Internet, a content distribution network, or any other wired, wireless, and/or telephonic network. In one embodiment, the portal application 401, API gateway 403, assessment API 405*a*, analytics API 405*b*, lambda function 407, PHI storage 409, and/or eye tracker computing system 411 may communicate with each other via network 413.

Figure 5:
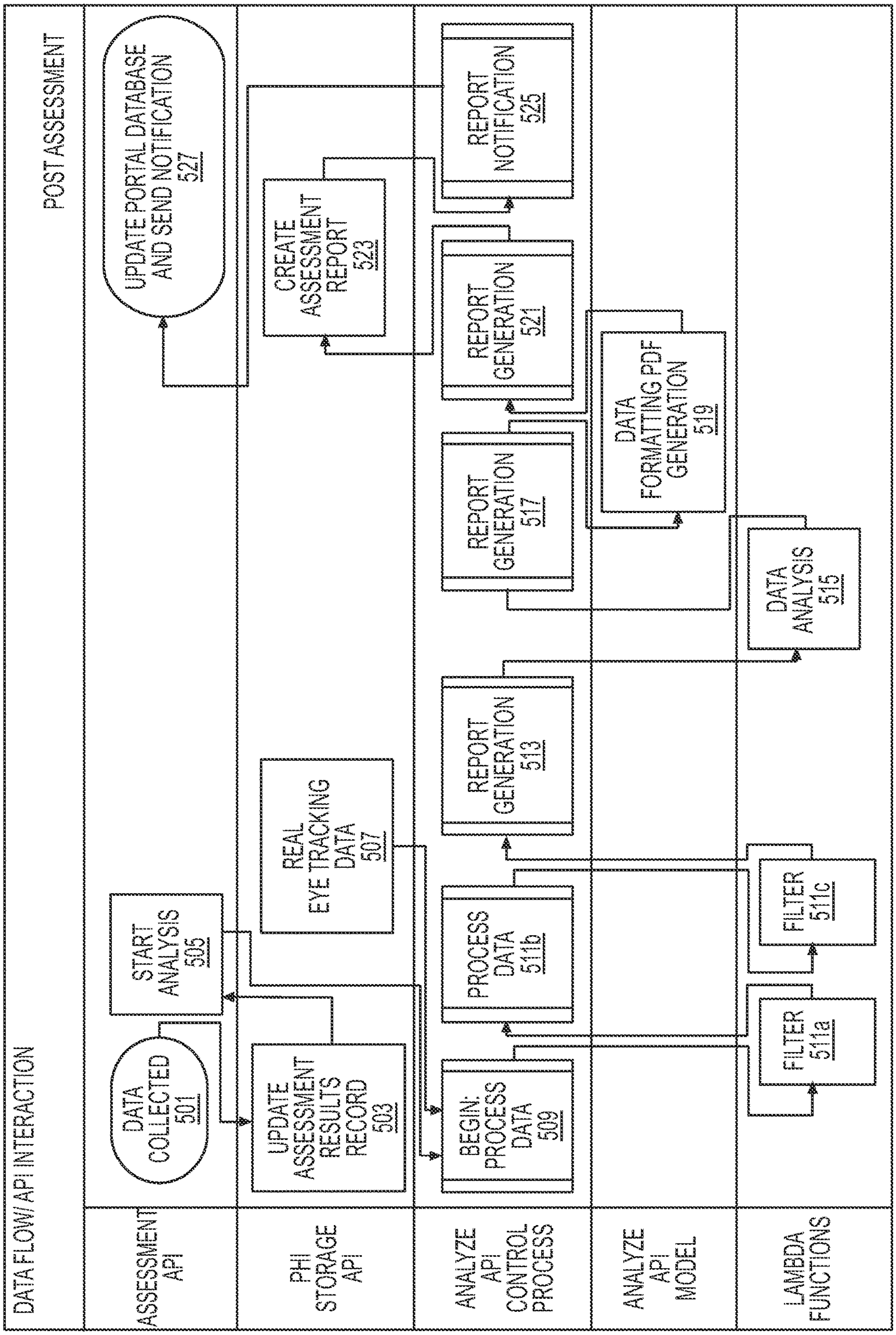
FIG. 5 is a flow diagram of an exemplary method associated with an exemplary eye evaluation system for hosting multiple human visual performance assessments, according to an exemplary embodiment of the present disclosure.

FIG. 5 is a flow diagram of an exemplary method 500 associated with exemplary eye evaluation system 400 for hosting multiple visual assessments, evaluating user performance on the assessments, and providing recommendations to improve, maintain, or rehabilitate user visual performance. In one embodiment of method 500, an assessment API (e.g., assessment API 405*a*) may receive data collected (step 501). In one embodiment, step 503 may include updating an assessment results record (e.g., by PHI storage 409, which may exist as an API). In one embodiment, step 505 may include the assessment API stating an analysis or an assessment. Upon initiating the start of an assessment, the PHI storage API may receive eye tracking data (step 507). An analytics API (e.g., analytics API 405*b*) may process data (step 509). In one embodiment, processing data may include filtering the data (e.g., step 511*a*), further processing filtered data (step 511*b*), then filtering data again (step 511*c*). In one embodiment, data processing may be performed by the analytics API, while a lambda function (e.g., lambda function 407) may perform the data filtering. The analytics API may further generate one or more reports (step 513).

In one embodiment, the one or more reports may be refined (e.g., by the lambda function). For example, lambda function 407 may perform further data analysis (step 515), and an analytics API may produce an updated report (step 507). In one embodiment, the analytics API may format a report (e.g., to produce the report as a pdf) or to otherwise facilitate user access and use of one or more reports (steps 519 and 521). In one embodiment, the visual assessment may also be evaluated and/or updated following analysis of a user's performance on the visual assessment. For example, the PHI storage API may create an assessment report (step 523). In one embodiment, a user may be informed of a completed report, for instance, via a notification at a web portal. For instance, the analytics API may generate a notification of a report being available (step 525) and/or the assessment API may update a portal database and/or send a notification to a user or user account (step 527).

Figure 6A:
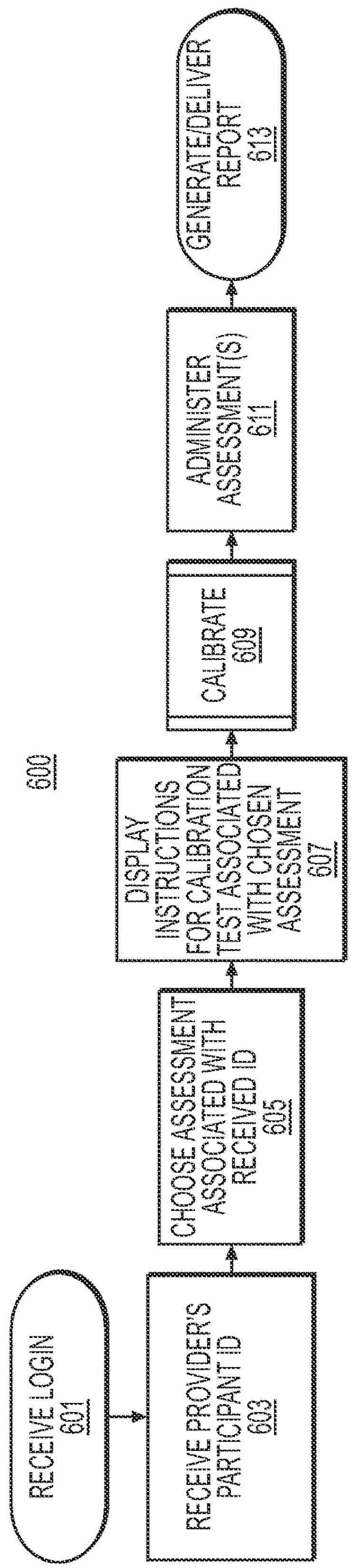
FIG. 6A is a flow diagram of an exemplary method for managing a human visual performance assessment using a web portal, according to an exemplary embodiment of the present disclosure.
Figure 6B:
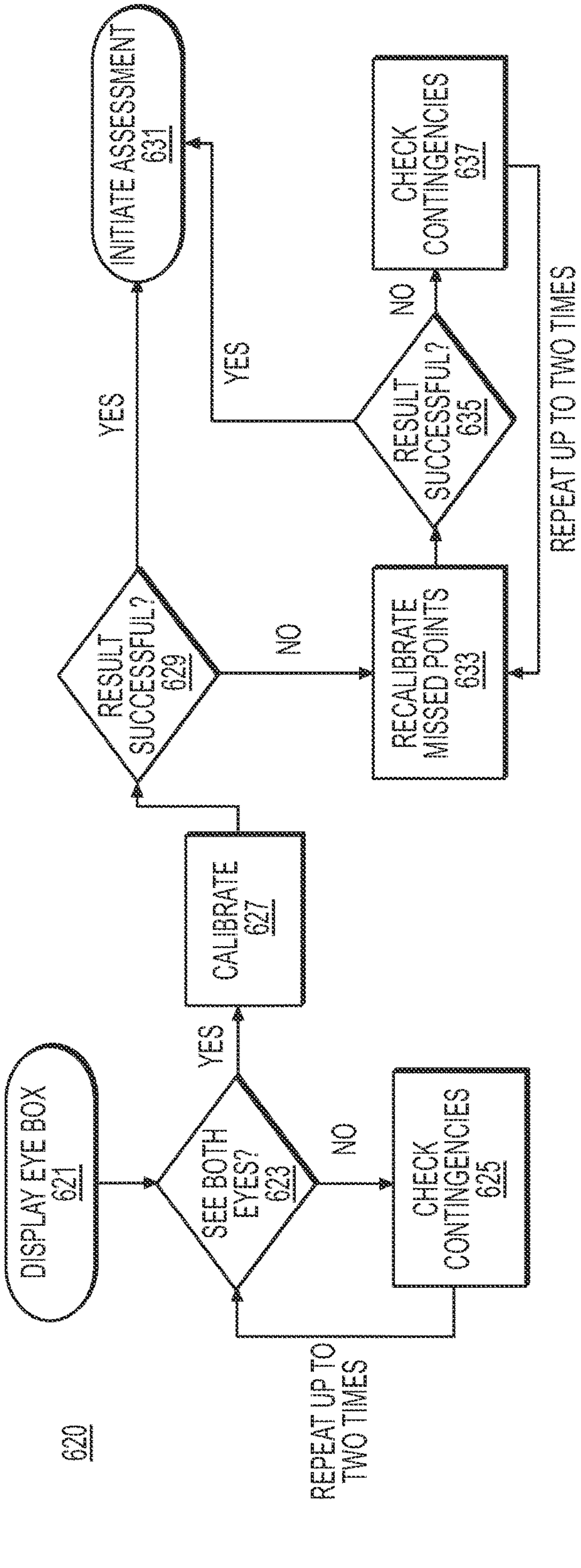
FIG. 6B is a flow diagram of an exemplary method for calibrating a human visual performance assessment, according to an exemplary embodiment of the present disclosure.

FIGS. 6A and 6B are flow diagrams of visual assessment workflows and calibration of the visual assessments, according to an exemplary embodiment of the present disclosure. FIG. 6A is a flow diagram of an exemplary method 600 for a managing an assessment using a web portal, according to an exemplary embodiment of the present disclosure. Step 601 may include initiating an assessment from a visual assessment repository. For example, step 601 may include a web portal receiving a notification of a user logging into the web portal. Step 603 may include receiving information associated with the user, including user/provider information or registration information. In one embodiment, step 605 may include receiving, selecting, or determining one or more assessments for the user to complete. Visual assessments may include one or more tests, games, and/or activities. Step 605 may include determining one or more assessments associated with a particular user (e.g., by user selection or subscription). The one or more assessments may be assessments hosted by a web platform (e.g., visual assessment and training/therapy platform 101) and accessed via a portal (e.g., web portal server 107).

In one embodiment, step 607 may include displaying, to a user, instructions for at least one of the one or more calibration tests associated with the determined assessment. Step 609 may include administering the calibration test and/or performing calibration for the determined assessment(s). For example, step 609 may include receiving information about an eye tracking device which may be receiving the user's response to each of the assessments. For instance, step 609 may include receiving information on a mobile device's orientation, location, and camera capabilities, where the mobile device will be used as an eye tracking device for the user, while the user may be completing the assessment. Step 609 may further include administering a series of prompts for a user to respond to, in order to calibrate for an eye tracking device and a user's response. (Calibration is discussed in greater detail in FIG. 6B.)

In one embodiment, step 611 may include administering the determined assessment(s) and/or receiving user performance data in response to each of the one or more determined assessment(s) (e.g., from the eye tracking device). In some scenarios, the eye tracking device may be the same device from which the user accesses the web portal. In one embodiment, step 613 may include generating and/or displaying reports of the user's performance on the assessments. The reports may include one or more performance metrics and/or recommendations for the user to improve, maintain, or rehabilitate his or her vision. The reports may further include past data, estimations of the user's performance relative to other users, and/or projected performance should the user follow the recommendations. (The reports are discussed in greater detail at FIG. 7B and FIGS. 8-13.)

FIG. 6B is a flow diagram of an exemplary method 620 for calibrating for a visual assessment, according to an exemplary embodiment of the present disclosure. may receive a login as shown in FIG. 6B, method 620 may involve control logic 201 prompting a calibration module 207. Eye tracking calibration may involve a computer/algorithm "learning" what a user's eye may look like when the user is looking at a known location on a user interface (e.g., a screen). For example, control logic 201 and calibration module 207 may prompt a mapping from a stimulito a gaze point, where the gaze point may include a location, on a display, where a user may be looking.

In one embodiment, step 621 may include displaying an eye box (e.g., via a portal user interface and/or an eye tracking device). In one embodiment, an eye box may be housed in a head box box. For instance, a head box may include a 3-dimensional space in which a user's head may move within (e.g., left/right, forward/backward, up/down, etc.) in order to capture eye movement data. An eye box may include a display shown on a screen that shows an image of where a user's eye(s) may be within the head box. The eye box display may permit and/or enhance data collection and calibration.

In one embodiment, step 623 may include receiving confirmation that both of the user's eyes are visible to the eye tracking device. For example, step 623 may include displaying, to a user, a point on a user interface and registering an eye tracker output when the user gazes at the point.

In one embodiment, step 625 may include checking contingencies, where contingencies may include issues related to data loss that may cause an assessment to be invalid. Contingencies may include movements that a user may do to compensate for vision deficiencies. Such movements may be due to injuries, mental health, biological conditions, etc. Exemplary movements may include one or more of: moving the head rather than the eyes (e.g., due to a concussion), malingering, attempts to artificially modify results, etc. Contingencies may be more prevalent or less prevalent, depending on the type of visual assessment. For example, a visual assessment employing stimuli presentations may be more influenced by contingencies than a visual assessment based purely on eye tracking. Exemplary stimuli presentations may include displaying a dot moving in a circle and instructing a user to follow the dot using his or her eyes, displaying an object as going from small to large across a three-dimensional (3D) display and asking a user to visually follow the displayed object, displaying objects in the periphery of a user's vision and asking a user to keep his/her vision still while making decisions about the object (e.g., about the size, color, or shape of the object), displaying various objects to a user and asking the user to physically respond to the displayed object (e.g., by pressing a button), displaying objects at various locations of an interface and instructing a user to move his/her eyes quickly to the displayed objects, etc. As can be understood from these examples, an assessment based on a stimuli presentation could be vulnerable to a user's compensations. For example, a user could move his or her body or head, rather than just the eyes. In another example, a user may continually press a button while taking an assessment involving the pressing of a button in response to a displayed object. The user may continually press the button in an effort to better his/her assessment results, rather than press the button in response to seeing a displayed object. In one embodiment, steps 623 and 625 could be repeated multiple times. In exemplary scenarios, various parameters may be adjusted between multiple iterations of steps 623 and 625, e.g., accounting for cleanliness of the eye tracker, reflection(s) or glare from a user's glasses, interference from sunlight, etc.

In one embodiment, step 627 may include performing a calibration test. For example, step 627 may include displaying, to a user, one or more environmental cues for calibrating the user's eye motions relative to an eye tracking device. Step 627 may also include comparing the gaze point of the user against an environmental cue (e.g., a circular dot displayed on a user interface). In one embodiment, step 627 may include displaying several points at various eye angles and tracking the user's gaze points across the user interface, in response to each of the points that are displayed at different eye angles. The number and spread of calibration points that may be used for an assessment may depend on the stimuli being presented in the assessment, as well as the accuracy and precision desired for the assessment results. For example, calibration may involve few calibration points if the calibration is a high school-issued eye assessment to reveal common eye problems (e.g., myopia). An eye assessment for fighter pilots deploying for service or an eye assessment for high-performance athletes may involve numerous calibration points. The number and locations of calibration points may influence the accuracy of the assessment results. For instance, a calibration model may be superior, not by employing more calibration points, but by providing the arrangement (e.g., location and/or timing of calibration points on a user interface) in a better layout. In one embodiment, the number of layout of calibration points in a calibration test may be altered based on responses to the tests from previous users. For example, the calibration test may be updated as the platform (e.g., platform 101) gathers more information about various users (e.g., grouped by user information) or about various tracking device(s).

In one embodiment, step 629 may include determining whether the calibration was completed. For example, step 629 may include determining whether the user completed the calibration test (e.g., of step 627). In one embodiment, step 631 may include providing the user access to a visual assessment. In one embodiment, step 629 may instead lead to step 633, of recalibrating missed points. For example, there may be a set of cues for which a user's response is not noted, either because the user did not respond to the cues, the user's response was not received, etc. Step 633 may include determining that completion of step 627 was lacking or unsuccessful and recalibrating missed calibration points. In one embodiment, step 633 may include not permitting a user to proceed unless a certain number of calibration points are received. For instance, step 633 may include a maximum number of missed calibration points and permitting a user to proceed only if the maximum number of missed calibration points is not exceeded.

In one embodiment, step 635 may include determining the completion of the calibration test (e.g., as recalibrated in step 633). In one embodiment, step 637 may include checking contingencies, similar to the process of step 625. Steps 633 and 637 may be repeated multiple times, for example, due to an obscured eye tracker or interfering lighting/image capture effects. In one embodiment, the user may be directed to his/her visual assessment (e.g., step 631) once it is determined that the user has successfully completed a recalibrated calibration test (e.g., of step 633 and/or step 637).

Figure 7A:
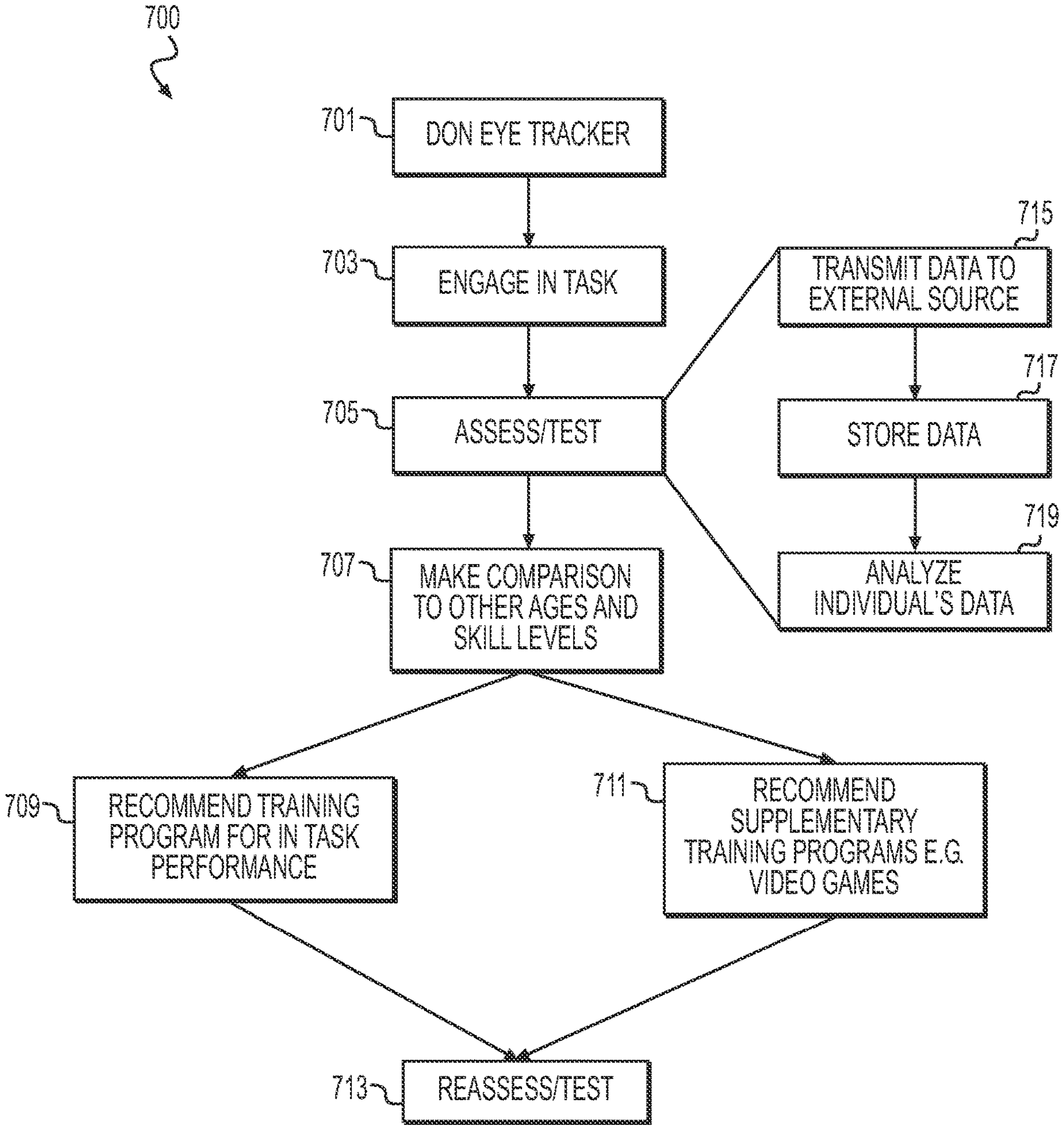
FIG. 7A flow diagram of an exemplary method for evaluating individuals' eye movements, and recommending training and therapy tasks for individuals to improve, maintain, or rehabilitate their vision and health, according to an exemplary embodiment of the present disclosure.

FIG. 7A is a flow diagram of an exemplary method for evaluating individuals' eye movements, and recommending training/therapy tasks for individuals to improve, maintain, or rehabilitate their vision and health issues, according to an exemplary embodiment of the present disclosure. Specifically, FIG. 7A depicts a method 700, which may be performed by both an operator of eye evaluation system 100 and a user, e.g., an individual or entity desiring to improve visual performance.

In one embodiment, step 701 may include detecting a user associated with an eye tracking device. For example, a user may don one or more eye tracking devices 117 (e.g., a wearable camera), whether implemented in a pair of glasses, a visor, a helmet, a pair of contacts, a secured mobile phone, and so on. Alternatively or additionally, the user may simply position himself or herself in the view of one or more remote cameras. In one embodiment, step 703 may include determining that a user is selecting one or more visual assessments (e.g., via a user interface displayed at a web portal). In one embodiment, step 705 may include administering an assessment and receiving eye tracking data regarding the user's performance on the assessment. Assessment(s) may include prompting a user to engage in any task that involves decision making before performing a physical action, for instance, a sports activity (e.g., swinging a baseball bat, a golf club, a foot at a ball, etc.), landing a plane, turning a corner, loading a pallet, performing a surgical procedure, etc.

In one embodiment, step 705 may also include assessing the user's eye movement. In one embodiment, assessing the participant's eye movement may include transmitting data collected from one or more eye trackers to an external source (e.g., a visual assessment platform hosting multiple assessments) (step 715), storing the data (step 717), and analyzing the user's data (step 719). For example, data may be obtained from one or more of wearable cameras and/or remote cameras, and transmitted to visual assessment and training/therapy platform 101. In one embodiment, a user's eye tracking data may be analyzed according to the metrics described at the end of the application, as well as methods described in U.S. Pat. No. 8,864,310 filed Mar. 14, 2013, the entire disclosure of which is hereby incorporated by reference in its entirety. A user's eye movement data may be analyzed so as to generate one or more scores, including one or more of a "target score," a "cognitive load score," and a "stress indicator score"

In one embodiment, step 707 may include making comparisons between the analysis of the participant's eye movement and the eye movement of other participants in the same or different age and skill levels. In certain embodiments, a target score, cognitive load score, and stress potential indicator score (both ideal scores and actual scores) may be determined based on skill level. In addition, those scores may be compared to ideal eye movement levels for a particular skill level for each specific task determined by expert level subjects' eye movement patterns. In some embodiments, measuring skill level and/or diagnosing levels of proficiency may occur at various times in the present and future. Measuring skill levels may also include implementing predictive reasoning equations and/or scores.

In one embodiment, step 709 may include either or both of: recommending training/therapy programs for in-task performance and recommending supplementary training/therapy programs (step 711). In one embodiment, step 709 may include developing and selecting drills or games based on the comparisons (e.g., of step 707) in order to facilitate learning and improve performance of a user or team of users.

In one embodiment, recommended training/therapy programs for in-task performance (step 709) may include recommending training/therapy drills in a physical space, whereas recommending supplementary training/therapy programs (step 711) may include virtual tasks, e.g., games or drills on a video game system or virtual simulator.

In one embodiment, recommending in-task performance training/therapy programs in step 709 may include recommending training/therapy drills developed based on scientific guidance that provides information on the best way to learn, the process of learning, and/or how people learn to specifically improve perceptual skill training/therapy. Training drills/therapy may also be developed via in-task experiences, for example, from coaches, medical specialists or therapists, and users. This information may then be used to develop training/therapy drills that direct the eyes and/or thoughts to engage in certain behaviors and not others.

In one embodiment, steps 709 and/or 711 may include recommending training/therapy drills that are progressive in nature based on a user's (or group of users') eye movement score obtained in step 705. In one embodiment, an assessment's scores may range from 0-3, 4-7, and 8-10. If a user scores from 0-3, the training/therapy drill may be broader in nature with an emphasis on correcting the general characteristics of the eyes and thoughts. A score of 4-7 may generate a training/therapy drill that is more specific, for example, including informing the user to look at a specific location and specific movements in time. Finally, a score of 8-10 may generate a drill that is highly specific and sensitive, for example, including looking within a certain degree of visual angle with specific on-set and off-set times while having to interpret what is being seen.

In one embodiment, the process for generating scores and training/therapy drills may include, a user taking an assessment (step 703), transmitting assessment performance data to the eye score servers/processors (step 715), scoring the assessment using an eye score scoring tool (step 719) to generate a specific score, e.g., based on a specific moment in time and/or a specific location and/or eye behavior; and linking scores for each moment in time to a specific database code that pulls, e.g., a training/therapy recommendation video into a report for the user to access (steps 709, 711).

Method 700 may then include reassessing (step 713), e.g., by repeating steps 715-719. In one embodiment, eye evaluation system 100 may identify and define an overall eye movement strategy recommended for the participant and the activity being performed and intended to be improved or maintained, e.g. reducing distractions and information intake or improved decision making. In one embodiment, eye evaluation system 100 may provide generic components of effective eye movement for the participant and defined activity, e.g. level gaze, like an airplane landing, stable gaze, like a tripod, in some cases also considering cognitive load of participant and related activity.

Figure 7B:
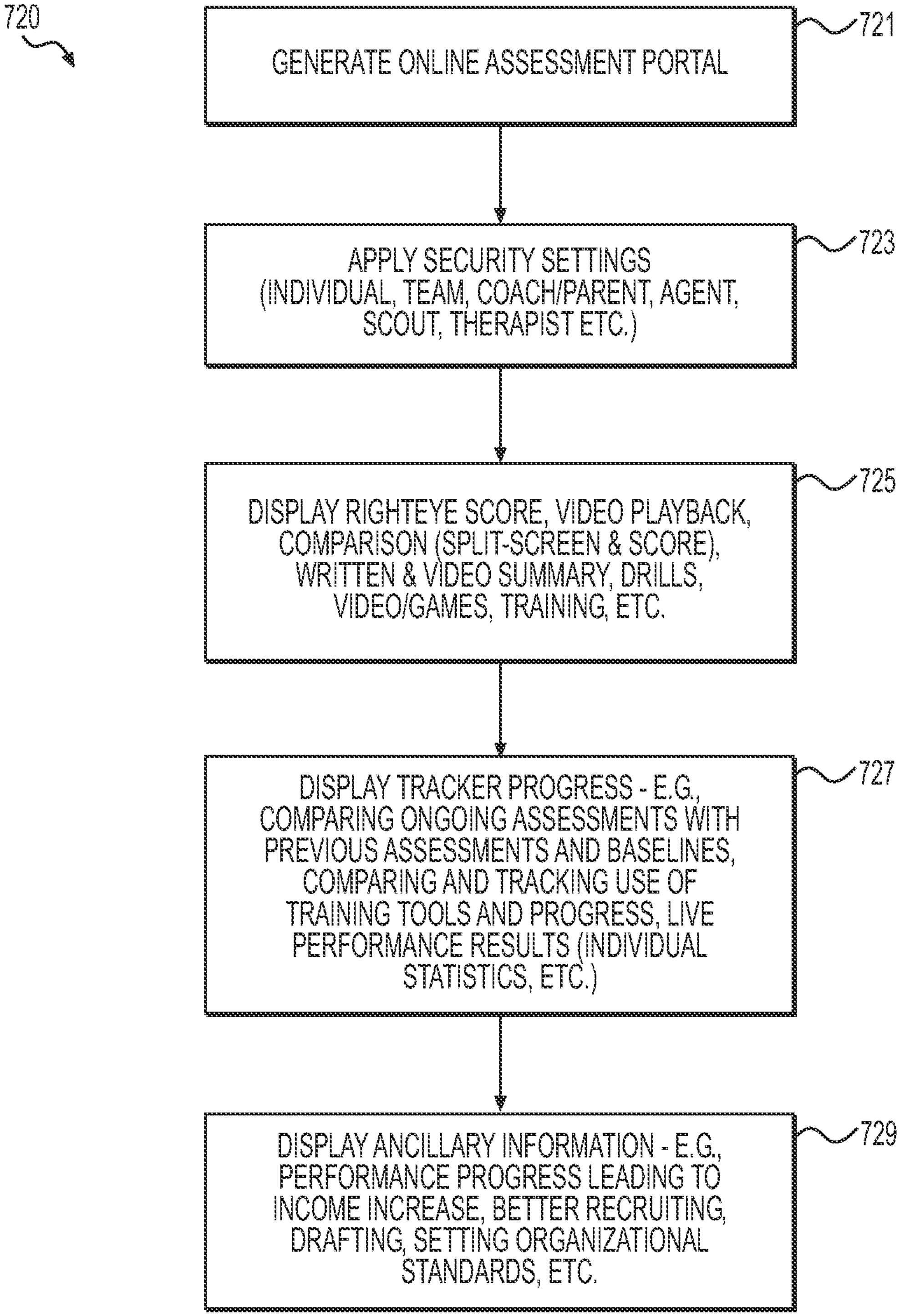
FIG. 7B is a flow diagram of another exemplary method for displaying evaluations of individuals' eye movements and recommending training and therapy tasks for individuals to improve, maintain, or rehabilitate their vision and health, according to an exemplary embodiment of the present disclosure.

FIG. 7B is a flow diagram of another exemplary method for displaying evaluations of individuals' eye movements and recommended training/therapy tasks for individuals to improve, maintain, or rehabilitate their vision and health issues, according to an exemplary embodiment of the present disclosure. Specifically, FIG. 7B depicts a method 720 for displaying one or more calculated scores to users and/or users' employers, e.g., via a web portal sever 107. As shown in FIG. 7B, method 720 may include generating an online "locker room" (step 721). A "locker room" may be any type of online user account, and may include any alternative naming convention based on the type of participant that the operator of eye evaluation system 100 is catering to. Generating the online account may include establishing web servers in communication with eye evaluation system 100, granting access to databases of scores and information (e.g., from results database 111), and establishing user interfaces for receiving, viewing, and interacting with stored scores and data. Method 720 may also include applying security settings (step 723). For example, access to the online account (or "locker room") may be controlled at the individual (participant user) level, team level, by coaches and/or parents, agents, scouts, therapists, employers, etc. Such settings may be dictated by a subscription level associated with a user.

In one embodiment, method 720 may include displaying at a web portal (e.g., web portal server 107) one or more calculated scores from assessments a user has completed, e.g., a generated target score, cognitive load score, and/or stress indicator score (one or more of which may be referred to as a proprietary "RightEye Score") (step 725), as described in U.S. Pat. No. 8,864,310 filed Mar. 14, 2013, the entire disclosure of which is hereby incorporated by reference in its entirety. For example, eye evaluation system 100 may display one or more scores along with a video playback of the evaluated action or task, comparisons to other individuals, written and/or video summaries of analysis, recommended training/therapy drills, video or game training/therapy drills, etc., of any of the other generated information discussed above. Method 720 may also include displaying tracking progress (step 727), which may include comparing ongoing assessments with previous assessments and baselines, comparing and tracking use of training/therapy tools and progress, and displaying live performance results (e.g., individual statistic). For example, method 720 may include displaying the results of performing comparisons (as in step 707, FIG. 7A), recommending training/therapy (as in steps 709, 711, FIG. 7A), and reassessing/testing (as in step 713, FIG. 7A).

Method 720 may also include displaying ancillary information (step 729), e.g., performance progress leading to income increase, better recruiting, better drafting, meeting organizational standards, etc. Thus, method 720 may display any of the results from performing one or more assessments hosted by the visual assessment and training/therapy platform 101, and related information about how those methods improve, maintain, or rehabilitate the visual performance of its users.

FIG. 7C is schematic diagram of an exemplary display of a user interface 740 of assessments that may be presented to a user via a web portal, according to an exemplary embodiment of the present disclosure. In one embodiment, the user interface 740 may include multiple assessments for user selection, e.g., neuro vision assessment 741, essential vision assessment 743, and performance vision assessment 745. In one embodiment, each of the assessments may include one or more tests, simulations, or measurements that may evaluate various metrics for the user's eyes. For example, neuro vision assessment 741 may include evaluations 747, which may include various smooth tracking and saccade tests. In one instance, essential vision assessment 743 may include evaluations 749, which may include tests or measurements of interpupillary distance, fixation stability, static visual acuity, dry eye, vergeance, accommodation (e.g., an accommodative convergence/accommodation ("ac/a") ratio), color vision deficiency, contrast sensitivity, field of view (range and/or recognition), fine depth perception, etc. In one instance, performance vision assessment 745 may include evaluations 751, which may include tests or measurements of that refer to how long and accurate a user may take to see, process, and respond to various targets. The evaluations 751 may further include visual acuity tests, tests for a user's focus or inhibition, and as well as tests showing a user's eye dominance or eye preference.

FIGS. 7D-7M are schematic diagrams of exemplary reports for one or more assessments that may be available to a user via a web portal, according to an exemplary embodiment of the present disclosure. Displayed elements of each of the diagrams may be included for one or more of the exemplary reports. In one embodiment, one or more of the displayed elements may be interactive, where a user may select one or more of the displayed elements and prompt a re-assessment or further assessment, a more in-depth explanation of the assessment/metric, a comparison of the metric against performance metrics of one or more other users (either by selection or by portal/assessment defaults), a comparison of the metric against the user's performance at one or more previous times, a storage or printing of one or more displayed elements, etc. The combinations of displayed elements are shown in FIGS. 7D-7M (and FIGS. 8-13) are exemplary. Any combinations of displayed elements may be used for any generated reports. In one embodiment, FIGS. 7D-7F may pertain to a neuro vision assessment, FIGS. 7G-7J may pertain to an essential vision assessment, and FIGS. 7K-7M may pertain to a performance vision assessment. Assessment reports (e.g., reports displayed to a user) may include exemplary graphics in any combination, within each of these groups. For example, a report may include one or more graphics within FIGS. 7D-7F. Another report may include one or more graphics shown in FIGS. 7G-7J. Alternately or in addition, reports may include one or more graphics and elements in any of the diagrams in FIGS. 7D-7M.

FIGS. 7D-7F are schematic diagrams of exemplary reports 760*a*, 760*b*, and 760*c*, respectively, for a neuro vision assessment, according to an exemplary embodiment of the present disclosure. Report 760*a* may include one or more images 761 showing a user response to an assessment. Report 760*a* may further include an image explanation 763 and/or a report explanation 765. Report 760*a* may further include various tables (e.g., table 767), which may show a metric, a computed response of one or more of the user's eyes, and/or a remedy respective of the metric. Report 760*a* may further include a table explanation (e.g., explanation 769), which may provide context to a user regarding the function and purpose of the tests, as well as what the metrics may mean. Report 760*b* of FIG. 7E and report 760*c* of FIG. 7F include further exemplary tables and graphics. As previously discussed, reports may include any combination of the exemplary graphics. For example, a single neuro vision assessment report may include any of all of the exemplary graphics of FIGS. 7D-7F.

FIGS. 7G-7J are schematic diagrams of an exemplary reports 770*a*, 770*b*, 770*c*, and 770*d*, respectively, for an essential vision assessment, according to an exemplary embodiment of the present disclosure. Report 770*a* may include a population comparison image 771, comparing a user's measurements against a population-averaged measurement. Report 770*a* may further include an eye comparison image 773, showing a comparison of each of a user's eyes for a particular metric. Other pictorial elements of reports may include exemplary bar graph 775 (e.g., of FIG. 7J, report 770*d*) and population comparison graph 777 (e.g., of FIG. 7J, report 770*d*). Report 770*b* of FIG. 7H and report 770*c* of FIG. 7I include further exemplary tables and graphics. As previously discussed, reports may include any combination of the exemplary graphics. For example, a single essential vision assessment report may include any of all of the exemplary graphics of FIGS. 7G-7J.

FIGS. 7K-7M are schematic diagrams of an exemplary reports 780*a*, 780*b*, and 780*c*, respectively, for performance vision assessment, according to an exemplary embodiment of the present disclosure. Report 780*c* may include table elements 781*a* and 781*b*, which may measure the same user performance (e.g., dynamic visual acuity) via different methods. Redundancy in an assessment may reveal nuances of a user's visual performance, so an assessment may test an aspect of a user's visual performance using different tests/simulations. As discussed above, any combination of user interface elements may be used in any reports.

FIGS. 8-13 are exemplary schematic diagrams of exemplary displays of reports that may be generated by the visual assessment and training/therapy platform 101 and/or the portal web server 107. Users may access their reports via the portal web server 107 and/or dictate which reports to view. In one embodiment, the same exemplary reports or metrics may be generated, in approximately the same format, regardless of which assessment a user takes. In other words, the visual assessment and training/therapy platform 101 and/or the portal web server 107 may generate reports of a uniform format, for all of the assessments/assessment applications 103*a*-103*n* hosted on the visual assessment and training/therapy platform 101. Alternately or in addition, reports or report displays may be specific to particular applications, user(s), and/or subscription levels.

Figure 8:
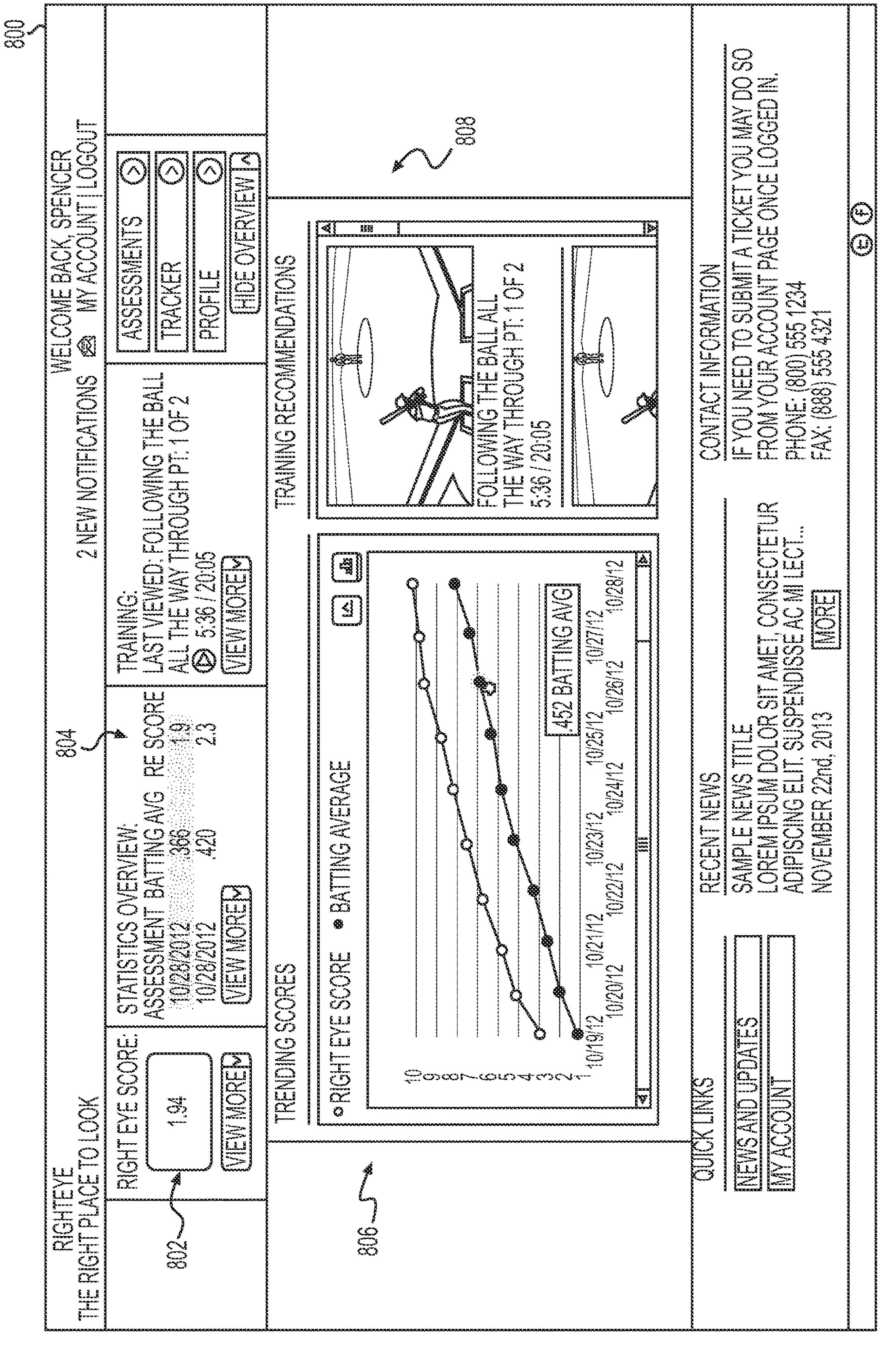
FIG. 8 is a schematic diagram of an exemplary display of evaluations of individuals' eye movements and recommended training and therapy tasks for individuals to improve, maintain, or rehabilitate their vision and health, according to an exemplary embodiment of the present disclosure.

FIG. 8 is a schematic diagram of an exemplary display of evaluations of individuals' eye movements and recommended training/therapy tasks for individuals to improve, maintain, or rehabilitate their vision and health issues, according to an exemplary embodiment of the present disclosure. In one embodiment, FIG. 8 is a screenshot of a web-based interface 800 for interacting with the visual assessment and training/therapy platform 101. Web-based interface 800 may be managed or operated by the visual assessment and training/therapy platform 101, hosted on one or more web servers over the Internet, and displayed on one or more devices 117.

In one embodiment, web-based interface 800 displays various eye evaluation information, such as various scores and calculated information. For example, web-based interface 800 may display a proprietary RightEye Score 802, which may be or include one or more of the target score, cognitive load score, and/or stress indicator score generated according to the methods described above. Web-based interface 800 may also display statistics associated with an evaluated task 804 of a visual assessment, e.g., how a user's performance may vary over time, and how a proprietary eye evaluation score may correlate with other scores or statistics typical of the evaluated task. In this case, web-based interface 800 depicts a calculated eye evaluation score in relation to a batting average calculated on different days. Although web-based interface 800 depicts the display of eye evaluation information in relation to baseball statistics, it should be appreciated that the web-based interface 800 may display eye evaluation information in relation to any other information or statistics typical of any other sport, activity, or profession, depending on the task and/or the participant. As shown in FIG. 8, the web-based interface 800 may also depict an eye evaluation score in a graph 806, along with one or more task-specific metrics or statistics, in this case batting average, over time. The web-based interface 800 may also display one or more training or therapy recommendations 808, including any of the training/therapy recommendations generated in steps 709, 711 (FIG. 7A). For example, web-based interface 800 may display training/therapy videos, embed training/therapy games, or display descriptions of how to improve, maintain, or rehabilitate a user's vision and health and/or techniques for improving/maintaining/rehabilitating any of the eye evaluation scores described above.

Figure 9:
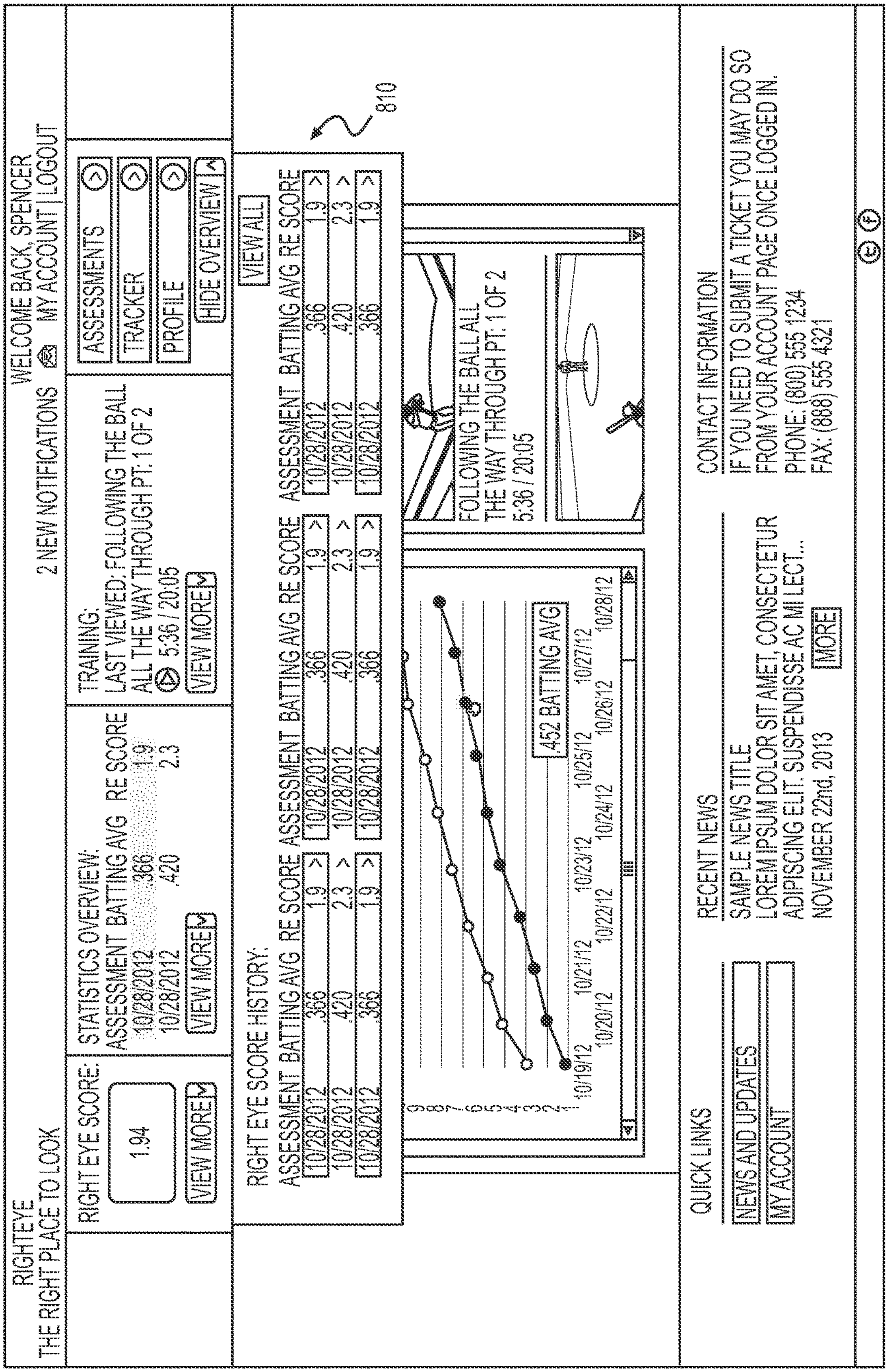
FIG. 9 is a schematic diagram of an exemplary display of evaluations of individuals' eye movements and recommended training tasks for individuals to improve, maintain, or rehabilitate their vision and health, according to an exemplary embodiment of the present disclosure.

FIG. 9 is a schematic diagram of the exemplary display of evaluations of individuals' eye movements and recommended training or therapy tasks of FIG. 8, but also including a display of history 810 of a participant's eye evaluation scores and task-specific scores or metrics.

Figure 10:
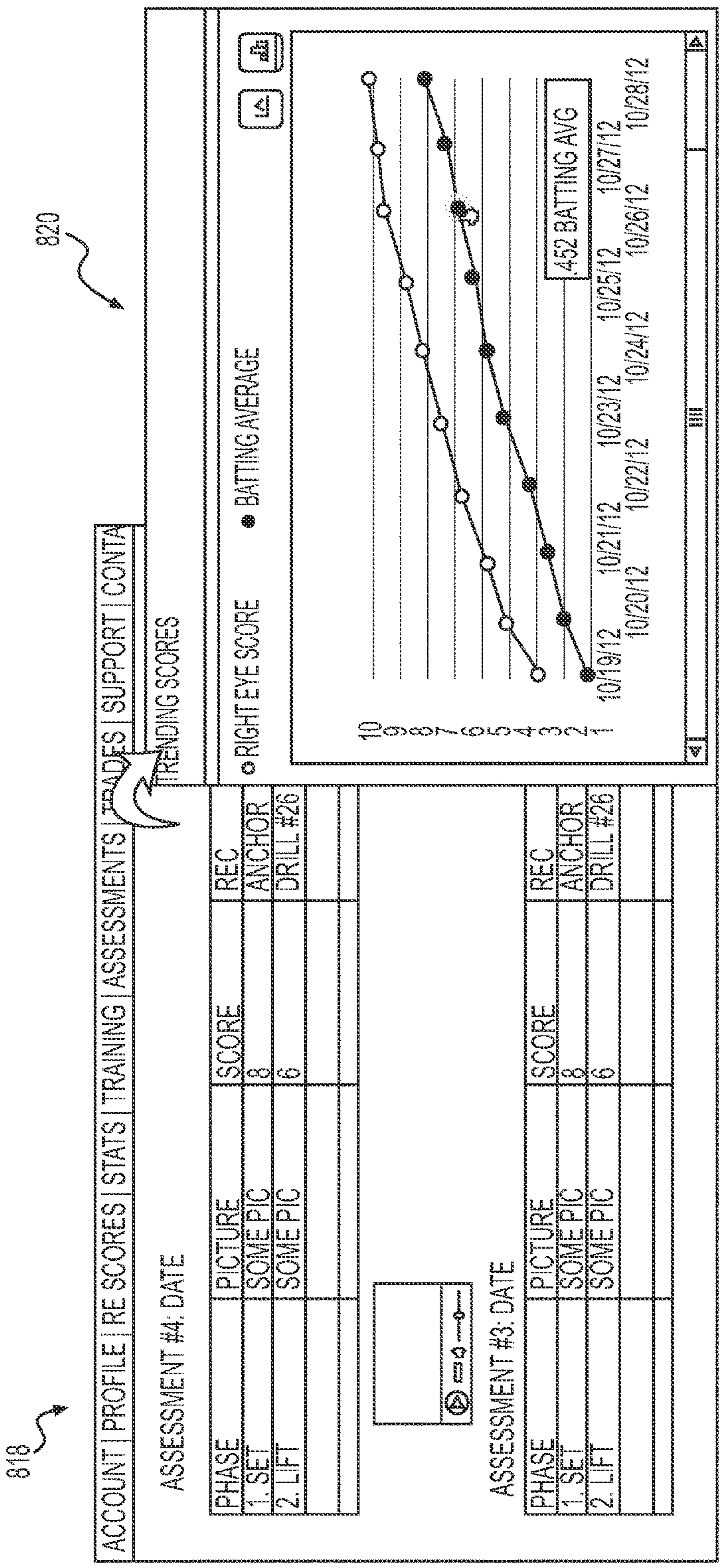
FIG. 10 is a schematic diagram of an exemplary display of evaluations of individuals' eye movements and recommended training and therapy tasks for individuals to improve, maintain, or rehabilitate their vision and health, according to an exemplary embodiment of the present disclosure.

FIG. 10 is a schematic diagram of an exemplary display of evaluations of individuals' eye movements and recommended training or therapy tasks for individuals to improve, maintain, or rehabilitate their vision and health, according to an exemplary embodiment of the present disclosure. As shown in FIG. 10, the web-based interface 800 of FIG. 8 may include an assessment page 818, including a breakdown of temporal or biometric phases, related pictures, related eye evaluation scores, and recommend drills. The assessment page 818 may also include links for participants to view and modify account information, profile information, eye evaluation scores, training/therapy, assessments, trades, and support. In addition, the assessment page 818 may include a trending scores window 820. Trending scores window 820 may graph one or more eye evaluation scores in relation to a task-specific score or metric over time, in this case graphing batting average against an eye evaluation score over time.

Figure 11:
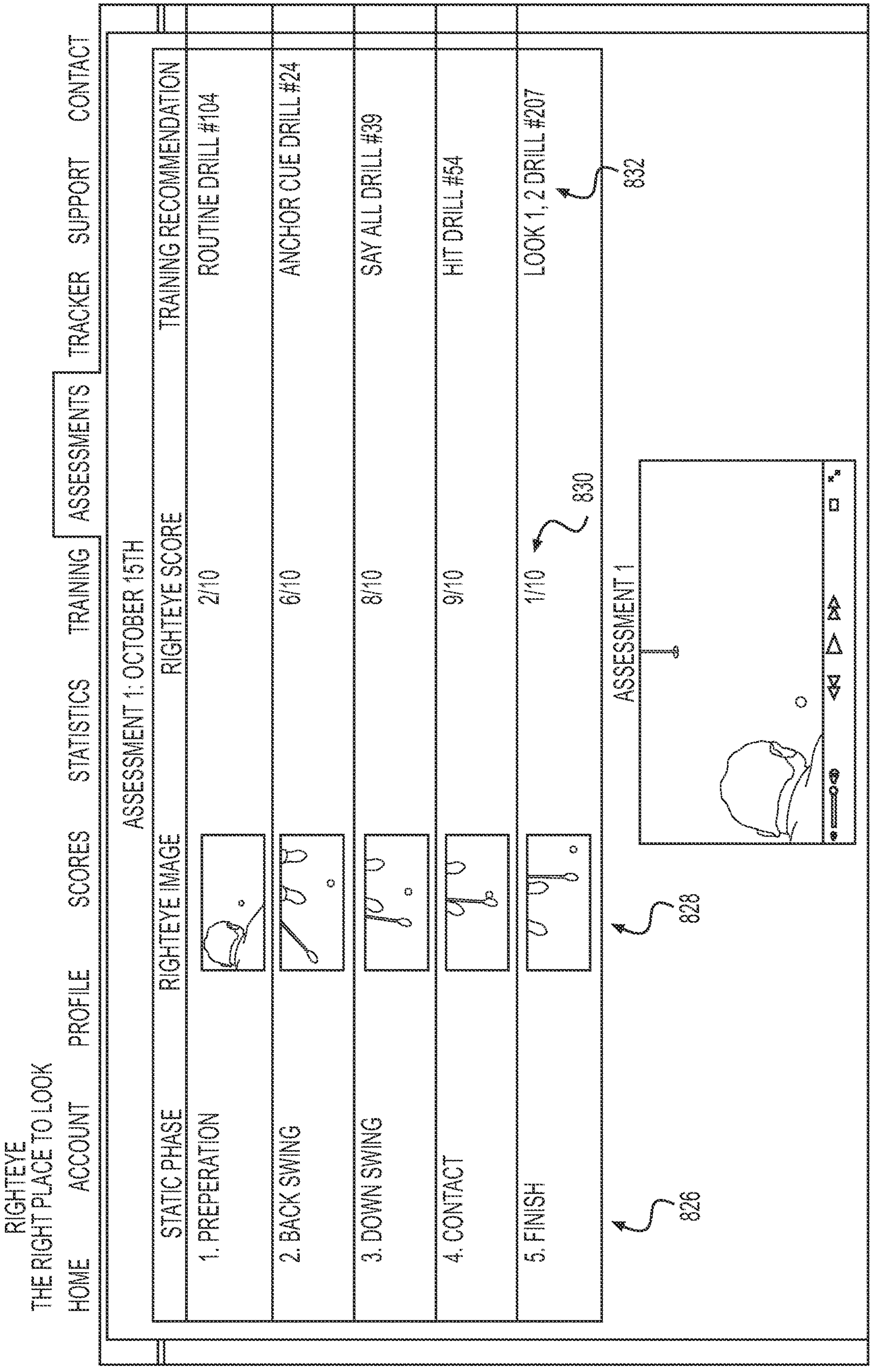
FIG. 11 is a schematic diagram of an exemplary display of evaluations of individuals' eye movements and recommended training and therapy tasks for individuals to improve, maintain, or rehabilitate their vision and health, according to an exemplary embodiment of the present disclosure.

FIG. 11 is a schematic diagram of another exemplary embodiment of the assessment page 818 of FIG. 10. As shown in FIG. 11, the assessment page may depict a plurality of static phases 826, including preparation, back swing, down swing, contact, and finish. The assessment page may also depict one or more related images 828, which may be images of the participant involved in the respective static phase, or of a professional or expert in an ideal stage of movement. The assessment page may also depict an eye evaluation score 830 associated with each static phase. Finally, the assessment page may depict a training/therapy recommendation 832 in relation to each static phase. In one embodiment, a training or therapy recommendation may be automatically selected based on a library of possible training or therapy recommendations corresponding to different scores. For example, a training or a therapy recommendation may be made based on whether it statistically improved the eye movement of others with similar eye evaluations or score.

Figure 12:
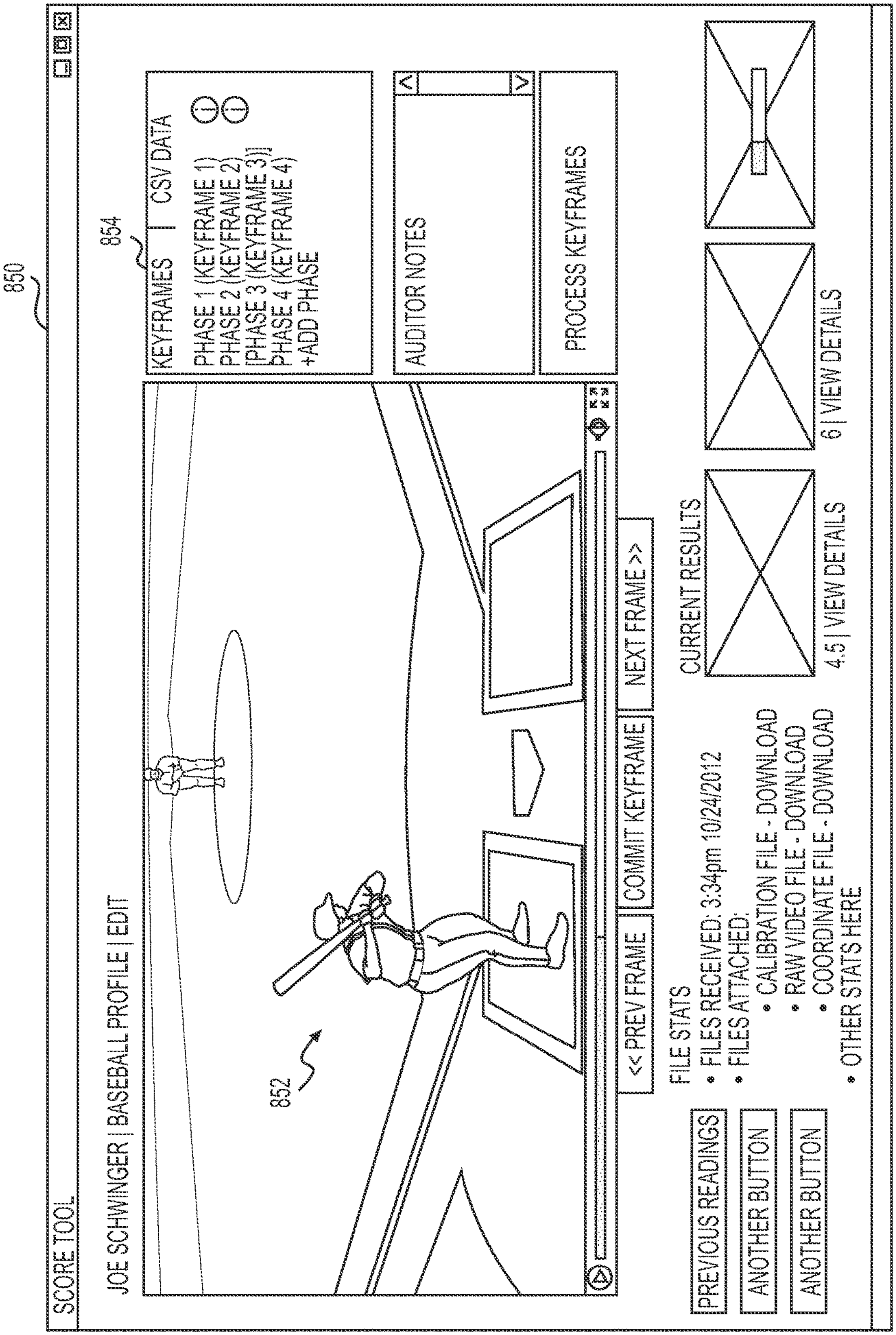
FIG. 12 is a schematic diagram of an exemplary display of evaluations of individuals' eye movements and recommended training and therapy tasks for individuals to improve, maintain, or rehabilitate their vision and health, according to an exemplary embodiment of the present disclosure.

FIG. 12 is a schematic diagram of an exemplary display of evaluations of individuals' eye movements and recommended training or therapy tasks for individuals to improve or maintain their vision and health, according to an exemplary embodiment of the present disclosure. Specifically, FIG. 12 shows that web-based interface 800 may include a scoring tool 850, which may include a video 852 embedded therein of a participant engaged in an evaluated task. In one embodiment, the scoring tool 850 may include keyframe data 854 enabling a user to evaluate the video 852 and define certain temporal phases (e.g., phase 1, phase 2, etc. as shown), for purposes of defining video segments and enclosed eye movement for scoring.

Figure 13:
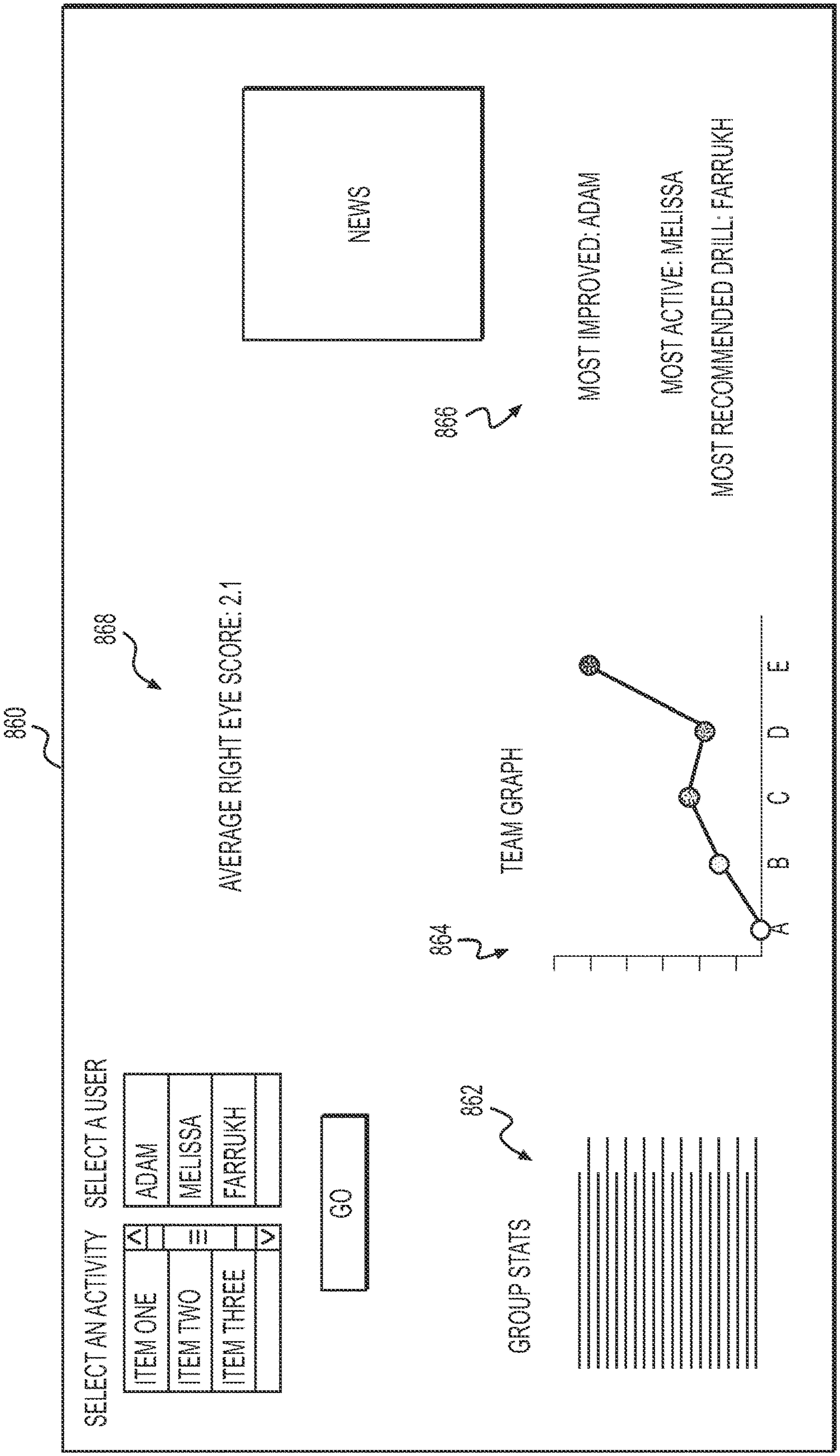
FIG. 13 is a schematic diagram of an exemplary display of evaluations of individuals' eye movements and recommended training and therapy tasks for individuals to improve, maintain, or rehabilitate their vision and health, according to an exemplary embodiment of the present disclosure.

FIG. 13 is a schematic diagram of another exemplary display of evaluations of a user's eye movements and recommended training or therapy tasks for users to improve their visual performance. Specifically, FIG. 13 depicts a team window 860 of web-based interface 800. As shown in FIG. 8, team window 860 may display one or more group stats 862 associated with a team of users, e.g., statistics relating to one or more eye evaluation scores averaged across the team. Team window 860 may also display a team graph 864, which may graph one or more assessment scores as averaged across a team over time or across team members. Team window 860 may also depict information 866 on specific team members relative to the whole team, such as "most improved," "most active," or "most recommended drill." Team window 860 may also display an average eye evaluation score 868 for an entire team. Of course, the average eye evaluation score may be of the target score, cognitive load score, and/or stress indicator score, or any other ancillary score described above, as averaged across one or more members of a team.

The previously described systems and methods to assess a user's visual performance may include various forms of assessments. In one embodiment, the assessments (e.g., hosted by the visual assessment and training/therapy platform 101) may include evaluations scoring visual acuity, visual strength, and visual search. The eye evaluation system 100 may further recommend training or therapy tasks to users to improve or maintain their vision and health, for instance, consistent with the exemplary methods described below. In some embodiments, the visual assessment and training/therapy platform 101 may leverage assessment information of multiple users to improve analytics for scoring a user's assessments and/or improving a user's vision. The following description includes a description of an exemplary assessment that may be provided by the visual assessment and training/therapy platform 101, the exemplary assessment being a Visual Performance Exam that may test visual acuity and/or visual strength and/or visual search.

Visual Performance Exam: An exemplary visual assessment hosted on a platform or gateway may include a fast, easy, accurate, reliable test to assess: (1) Visual Acuity, which may include a measure of clarity of vision including but not limited to monocular sensory processes (e.g., contrast sensitivity and/or static visual acuity), (2) Visual Strength, which may include a measure of eye teaming (e.g., binocular sensory processes) and fatigue of vision (e.g., accommodation and/or vergence and/or depth perception, and/or (3) Visual Search, which may include a measure of where and when a person looks, visual decision making, visual integration, and/or information processing. In one embodiment, the visual performance exam may include a Smooth Pursuit Eye Movements (SPEM) test, e.g., for indicating the presence of traumatic brain injury. In another embodiment, a SPEM test may be offered as an independent assessment hosted by the visual assessment and training/therapy platform 101.

The Visual Performance Exam may include formulas that incorporate individual-specific demographic parameters, such as age (e.g., date of birth), years of experience (e.g., years spent at this particular task), skill level (e.g., current level of aptitude at this task, with scale varying for each sport/activity), and/or gender. The Visual Performance Exam may include any one or more of the following eye tracking variables:

| Eye Tracking Variable | Example parameters |
|---|---|
| Search Rate Score | May include the number of fixations divided by time for each repetition and averaged across assessments. A lower score may indicate higher potential for expertise. May indicate a lay person's ability to focus. (# fixations/time (msec)) |
| Average Fixation Duration Score | May include the length of time the person looked within at a specific point before moving their eyes. (e.g., within 3 degrees of visual angle for a minimum of 100 milliseconds.) |
| Standard Deviation of the Average Fixation Duration Score | The Average FD may be scaled based on a bell curve, and the Average FD may provide a quantitative result and qualitative descriptor. |
| Average Target Score | An average score, may be captured by looking at the right spot (area of interest) at the right time (biomechanical phase). A score may be captured for each repetition and phases within the repetition, then averaged across all phases and repetitions to create the Average Target Score |
| Standard Deviation Target Score | A variance score, may be captured by looking at the right spot (area of interest) at the right time (biomechanical phase). A score may be captured for each repetition and phases within the repetition then averaged across all phases and repetitions to create the Average Target Score |
| Quiet Eye Score | A fixation or tracking gaze that may be presented on a specific location or object in the visual motor workspace within 3 degrees of visual angle for a minimum of 100 milliseconds. |
| Visual Inhibition Score | May evaluate the ability of a participant to not respond to a target, for instance, to not be distracted by the wind blowing flags beside the tennis court or a car moving behind a sports field. The inhibition score may be measured via number of hits/looks. In some cases, the best score may be a zero and the higher the score the less desirable. |
| Target Locator Time Score | May include the time between the initiation of the task and the ability to fixate within 3 degrees of visual angle for a minimum of 100 milliseconds on the first area of interest. In some cases, the shorter the period of time the better the score. |
| Visual Calibration Score | May evaluate a scan path that occurs between two objects (3 degrees of visual angle for a minimum of 100 milliseconds) at a minimum of one time prior to a task beginning. One example of visual calibration in baseball may include looking at the plate and then to the pitcher, which could occur once or several times in succession without the scan path deviating to another object. The visual calibration score may therefore reflect a participant's compliance with a pre-performance visual routine. This may be represented as 0 for no visual calibration present, to 1 indicating at least one visual sequence, 2 or 3 visual sequences. The visual calibrations may include averages across repetitions. |
| Pursuit Tracking Score | May evaluate a participant's ability to follow an object, such as a ball, over time and distance. The pursuit tracking score may be a percentage of time tracking an object from one defined location to another within a certain range of visual accuracy around the object. The pursuit tracking score may be given over distance and/or time traveled and represented as a percentage score and/or frame-by-frame score. |
| Visual Routine Score | May evaluate the consistency of visual cue location (measured, for example, at 3 degrees of visual angle for a minimum of 100 milliseconds) associated with task locations over time. Similar to a visual calibration score, the visual routine score may be a measure via a scan path over time between two or more objects. The visual routine score may measure the consistency of visual cue locations across the presentation of the same and/or similar skills. For instance, during the presentation of skill 1, the scan path may be cue A to cue B to cue C. In the presentation of skill 2, which is skill 1 repeated, if the scan path remains the same, i.e., cue A to cue B to cue C, then the visual routine score would be high (a desired result assuming the cues are accurate for the task). However, if the visual scan path changes in presentation of skill 2 (e.g. cue A to cue D to cue A) then a lower score may be assigned due to the deviation in scan path from the presentation of skill 1 to skill 2. The visual routine score may or may not be represented as a percentage and/or as a measure on a scale from high to low. Frequency of the routine may or may not be considered as a metric to determine results and/or score. |

-continued

| Eye Tracking Variable | Example parameters |
|---|---|
| Pupil Dilation Frequency Score | May include measuring the frequency of pupil dilation, which may correlate with cognitive workload. That is, the score may increase (e.g., frequency of dilation may increase) as the degree task difficulty increases. |
| Visual Reaction Time Score | May be calculated for a specific point in time to the determination of a response. Time points may be before, during, or after the completion of a skill. Responses may be but are not limited to motoric and/or verbal responses. Visual reaction compared to motor or verbal reactions can be examined to gather more finite information about cognitive processing. For instance, visual reaction time may be an indicator of mTBI. |
| Advanced Cue Utilization Score | May be similar to the Recognition Grade/Score and may include a grade/score that may indicate decision accuracy that may include but may not be limited to verbal and/or motoric response, without reasoning, regarding where a subject should be looking and may or may not include temporal aspects of the task. Task may be static or dynamic. Time may or may not be included in the metric. |
| Recognition Score | Exemplary embodiment: Do you see the important cue (to be defined)? Yes/No. Do you look at it long enough? >250 ms |
| Situational Probabilities Score | May refer to the placement of a gaze at specific critical moments in time and may include at least one outcome measure. e.g., an anticipation or decision-making score. May be task-specific and inferred from placement of gaze and outcome results providing quick and accurate measure of the person's ability to foresee outcomes based on gaze location and outcome measures. |
| Visual Relax Score | May include a visual search pattern (including fixations, saccades, and pursuit tracking) that is seemingly random and occurs after the completion of one task and before the Visual Anchor of the next task. The Visual Relax may be a low concentration time designed to help the subject relax and restore brain processes between tasks. The Visual Relax Grade/Score may be marked as present or absent. A time factor may or may not be associated with the score. |
| Anchor Cue Score | May include a fixation or tracking gaze that is located on a specific location or object within 3 degrees of visual angle for a minimum of 100 milliseconds occurring after the Visual Relax and before the Visual Calibration. The Anchor Cue may be close in visual range to the participant (within 6 feet, depending on the task). The Anchor Cue may be designed to bring the mental and visual focus back to the task at hand after a time of relaxation (e.g., the Visual Relax). The Anchor Cue Grade/Score may be measured by identification of the cue (a fixation or tracking gaze that is located on a specific location or object within 3 degrees of visual angle for a minimum of 100 milliseconds) within a close range of the subject performing the task. Examples may be a bat or diamond for a baseball hitter, a racquet for a tennis player, the ground in front of a subject for a soccer goal keeper. |
| Visual Angle Score | May include a degree of horizontal variation from center (x and y coordinates) to left and/or right (x and y coordinates) measured via visual object/s and scene camera angles. Score and/or grade may be represented as a left to right and/or positive to negative range of degrees between 0-360. The Visual Angle Score/Grade may include a metric that influences the Vantage Point Score/Grade. |
| Vantage Point Score | May include the Visual Angle Grade/Score as well as the distance and velocity an object is from the subject. Vision may be accurate in observing motion at right angles to the line of sight. The Vantage Point Score/Grade may provide a metric indicating the difficulty in the Vantage Point in order to provide feedback that includes but is not limited to head position and/or body position and/or eye position. |
| Viewing Time Potential Score | May include a grade/score that compares the subjects Vantage Point Grade/Score against an ideal Vantage Point Grade/Score in order to determine the missing potential in terms of, but not limited to, angles, velocity, distance. These metrics may be calculated to determine the potential increase in viewing time of the task. Feedback may be provided to the subject from the Viewing Time Potential Grade/Score to indicate if vantage point and appropriate body movement can be used to increase viewing time in order to improve performance. |

-continued

| Eye Tracking Variable | Example parameters |
|---|---|
| Visual Lock Score | May include a fixation or tracking gaze that is located on a specific location or object within 3 degrees of visual angle for a minimum of 100 milliseconds. The onset of the Visual Lock may occur either after a Visual Calibration or after a Visual Relax. The Visual Lock Score or Grade may be rated by location applicability for the task. One example can be prior to a fast motion, e.g., a soccer penalty kick, the subject should have a visual lock on the opponents center mass in order to begin with the most effective location for seeing the upcoming event or task. Therefore, in this case, center mass may be the bull's-eye and if the subject is looking at the center mass after a Visual Calibration or after a Visual Relax they receive the highest grade and/or score. In some cases, the further from center mass, the lower the Visual Lock Grade and/or Score. This may be different than the Quiet Eye Grade and/or Score in that the Quiet Eye may measure a fixation in any location, whereas the Visual Lock may take into account the appropriateness of the location and grade this location based on the upcoming task. |
| Pursuit Tracking Skill Comparison Score | May include a percentage of time tracking an object from one defined location to another within a range of visual angle. The Pursuit Tracking Grade/Score may be given over distance and/or time traveled and represented as a percentage score. The percentage score may be compared to benchmark scores from other skill levels where a further grade and/or score may be given to the subject that represents their comparative skill level. |
| Focal Tracking Ability Score | May measure when the focal vision is no longer physiologically able to track the object due to speed over time and may also include visual space (e.g., closer versus further away) compared with the individual subject's loss of visual tracking to determine if an increase in visual tracking time is physically possible. |
| Black Hole Score | May also be known as a saccadic suppression. Saccades may include the movement of the eye at a rate of less than 100 milliseconds at 3 degrees or greater visual angle. Saccades may not track an object over a distance, instead they can reposition eyes quickly from one target of focal vision to the next but the eyes are essentially turning off as they saccade to the next fixation (Cambell & Wurtz, 1978). This may be called saccadic suppression and/or black hole in vision and is needed to prevent a blur of vision as the eyes move across the visual field. A Black Hole Grade and/or Score may be assigned as a percentage of time, over a task in which the eye moves at a rate of less than 100 milliseconds at 3 degrees or greater visual angle and is not pursuit tracking. |
| Response Time Score | May include a response time score that may evaluate an interval of time involving both reaction time and movement time, e.g., the time from the onset of a stimulus (e.g., gunshot) to the completion of the movement e.g. crossing the start or finish line. Responses may be but are not limited to motoric and/or verbal responses and/or eye movement. |
| Reaction Time Score | May be calculated for a specific point in time to the determination of a response. Time points may be before, during, or after the completion of a skill. Responses may be but are not limited to motoric and/or verbal responses. |
| Simple Reaction Time Score | May include a simple reaction time score that may evaluate when a situation requires only one signal and one action (motor, verbal or eye movement) in response. One example of reaction time may include a sprinter reacting to a gun (the go signal) and responding by running (the action) is an example of simple reaction time. In one embodiment, reaction time may be calculated from a "Go Signal" zero time to initiation of response, including premotor and motor components, to one stimuli/situation. |
| Discriminate Reaction Time Score | May include a discriminate reaction time score, which may evaluate where there is more than one signal, but only one response. For example, three objects may appear on a screen: a triangle, square and circle. The athlete may be prompted to only respond to the circle and ignore the square and triangle. Reaction times may be longer in discriminate reaction time situations than simple reaction time, due to an increase in information processing and decision making needed to respond accurately to the situation. The formula for discriminate reaction time may or may not include an error |

-continued

| Eye Tracking Variable | Example parameters |
|---|---|
| | score. In one embodiment, reaction time may be calculated from "Go Signal" zero time to initiation of response, including premotor and motor components, to one stimuli/situation while ignoring others. |
| Choice Reaction Time Score | A choice reaction time score may evaluate where there is more than one signal to which the person may respond and each signal may have a specified response. This is may be referred to as the "If this . . . then that" reaction time. For instance, a training/therapy drill related to the choice reaction time score may include displaying a circle on a screen, that a participant must look at, until it disappears. If a square appears on the screen, then the participant may avoid looking at it for the assessment. If a triangle appears on the screen then the assessment may ask that the participant follow it with their eyes as it moves left and right, and so on. In one embodiment, a formula for choice reaction time may or may not include an error score. In one embodiment, choice reaction time may be calculated from a "Go Signal" zero time to initiation of a response, including premotor and motor components, to one stimuli/situation with the correct "choice"/response. |
| Pre-Motor Component Score | A pre-motor component score may evaluate time from the initiation of the "Go Signal" to the beginning of a motor component response. This may be measured through either biofeedback and/or psycho-physiological feedback. In one embodiment, a pre-motor component reaction time may be calculated as a reaction time - motor component. |
| Motor Time Component Score | A motor time component score may evaluate time from the initiation of a motor component, measured via either biofeedback and/or psycho-physiological feedback, until the initiation of a response. In one embodiment, a motor component reaction time may be calculated as reaction time minus a pre-motor component time. |
| Movement Time Score | A movement time score may evaluate the interval of time between the initiation of the movement and the completion of the movement, such as, when a sprinter begins to move in response to the gun until when she crosses the start/finish line. Another example may be when the eyes begin to move until they reach their target. In one embodiment, movement time may be calculated based on the time between initiation of the response until termination of the response. |
| Target Overshoot/Undershoot Score | A target over/undershoot score may evaluate the amount of constant error beyond the target, the signed deviation (+/−) from the target. For example, the score may represent the amount and direction of error and serve as a measure of performance bias. The over/undershoot score may be signed (+/−) and receive a distance metric. For example, 3 centimeters may refer to stopping 3 centimeters short of the desired target. In one embodiment, the target over/undershoot score may be calculated based on a distance from the center of the target to center of the eye movement stopping point, adding a minus for stopping too early and a plus for overshooting |
| Target Miss Score | A target miss score may refer to the unsigned deviation (miss) from the target, representing the amount of error. The target miss score may include the absolute error, a measure of the magnitude of an error without regard to direction of the deviation. The target miss score, for example, may be 3 centimeters and refer to the distance the eye stopped from the target, but not the direction of the error (e.g., stopping short or overshooting). In one embodiment, the target miss score may be calculated based on a distance from the center of the target to the center of the eye movement stopping point. |
| Target Consistency Score | A target consistency score may refer to the variable error representing the variability (or conversely, the consistency) of performance. For example, in one embodiment, standard deviation of the users' target over/undershoot (x) may be calculated based on the score (constant error) for the series of trials. |
| Target Movement Score | A target movement score may evaluate an error involved in continuous skills, such as following a ball (or object), to indicate the amount of error between the performance curve and the criterion performance curve for a specific amount of time during which the performance is sampled. In one embodiment, the target movement score may record whether |

-continued

| Eye Tracking Variable | Example parameters |
| --- | --- |
| | the eye is within or outside of the range of a target as it moves, as opposed to distinguishing the type of eye movement characteristic. An individual's user score may then be graphed and compared to the amount of error between the performance curve and the criterion performance curve for the length of time of the task. |
| Smooth Pursuit Eye Movement Score | A smooth pursuit eye movement score may evaluate an error measure used for continuous skills, such as following a ball (or object) to indicate the amount of error between the performance curve and the criterion performance curve for a specific amount of time during which the performance is sampled. The smooth pursuit eye movement score may distinguish between the type of eye movement characteristic and only include smooth pursuit eye movements (e.g., excluding fixations or saccades). |
| Recognition Score | A recognition score may be a score that indicates decision accuracy that includes but is not limited to verbal and/or motoric response, with reasoning, regarding where a subject should be looking and may or may not include temporal aspects of the task. In certain embodiments, the task may be static or dynamic, and the time may or may not be included in the metric. For example, the user may be prompted to verbally respond to the particular play (e.g., running play) in American football and then the user may be prompted to explain why he recognizes the play as a running play. The recognition score may measure whether the athlete's response to the recognition of the play is accurate or inaccurate and the recognition score may or may not include a time to respond. |
| Cue Identification Score | A cue recognition/identification score may indicate a decision accuracy that includes but is not limited to verbal and/or motoric response, without reasoning, regarding where a subject should be looking and may or may not include temporal aspects of the task. In one embodiment, a task may be static or dynamic, and time may or may not be included in the metric. For example, the user may be prompted to verbally respond to the particular play (e.g. running play) in American football. Unlike the recognition score, the user may not be prompted to explain their reasoning for the decision to call what they saw as a "running play." The cue identification score may measure whether the user's response to the cue/display is accurate or inaccurate, and may or may not include a time to respond. |
| Reasoning Score | May include a measure of a subject's quality to explain why s/he responded in a certain way to a task and/or a part of a task. It may include, but is not limited to, looking at a location, responding with a verbal and/or motor response. The Reasoning Grade/Score may provide information on what is being extrapolated and/or interpreted from the environment. One example may be a subject having to pick a "best response" from a list of response and/or reason an explanation. |
| Verbalization Score | May include a qualitative or quantitative measure of the subject's verbal "self-task" while engaging in a task. |
| Breathing Score | May include a measure of breath rate over time, breath holds, intake and outtake time and/or temporal phasing of breath. |
| Visual Stability Score | May include the length of time a fixation or gaze location remains stable (within 3 degrees of visual angle for a minimum of 100 milliseconds) in accordance with head tilt measured by the Visual Angle Grade/Score. |
| Brain Plasticity Score | Brain plasticity may include the capacity to change the structure, and ultimately the function, of a brain. Initial research indicates that eye movements gathered during training/therapy exercises can be a useful indicator of brain plasticity. The Brain Plasticity Score/Grade may be measured from one testing session to the next and may or may not be measured at increments between testing sessions. The Brain Plasticity Score/Grade may be used to indicate rate of change and adaptation based on in-task and related-to-task training/therapy tools recommended to the individual to be applied, including training/therapy games, video games, training/therapy drills and/or other training/therapy programs. The Brain Plasticity Score/Grade may be measured via the change over time in the Reasoning Grade/Score and/or the Recognition Grade/Score and/or the Target Grade/Score. |

-continued

| Eye Tracking Variable | Example parameters |
|---|---|
| Blink Score | A blink score may refer to the timing and/or length of a blink before and/or during and/or after a task. The blink score may provide information about "lost" vision including when that vision was lost within the task which may help to indicate a loss of ball tracking at a critical point in time. In one embodiment, a formula for the blink score may include a time length of blinks divided by a length of a task. |
| Blind Vision Score | A blind vision score may be generated when the eye is tracking an object which may or may not change distances and/or speeds. For example, blind vision may occur when the eye can no longer physiologically track the object due to either the distance and/or speed of the object. The score may be presented as a percentage, a raw score, a time score, and/or an "off"/"on" score. A possible formula for the blind vision score may include a time that an eye is "on," e.g., tracking, divided by a total task time. |
| Peripheral Visual Range Score | Peripheral vision may permit the ability to see movement in blurs (not in any detail). Peripheral vision may account for 6-220 degrees of a person's visual field. This may correspond to 2.73 to 100 percent of a person's overall visual field. |
| Depth Perception Score | May include the visual ability to perceive the world in three dimensions (3D) and the distance of an object. Depth perception may arise from a variety of depth cues. These depth cues may be classified into binocular cues that may be based on the receipt of sensory information in three dimensions from both eyes and monocular cues that can be represented in two dimensions and observed with one eye. Binocular cues may include stereopsis, eye convergence, disparity, and yielding depth from binocular vision through exploitation of parallax. Monocular cues may include size: distant objects subtend smaller visual angles than near objects, grain, size, and motion parallax. |
| Clustering Score | May represent the pattern of groupings of eye fixations across time. The score may indicate how similar a pattern of groupings of fixations given a specific task and a specific skill level. Using the database, specific patterns may emerge from skilled players. The patterns may be comparable and indicate a skill level of an individual athlete. The attention allocation strategy may be represented by a strategy of eye movements. This strategy may result in a pattern and indicate a degree of task performance. |
| Speed of Processing | May include a combination of visual reaction time, search rate, and at least one outcome metric. Speed of processing may be designed to get at the raw ability to respond across time. |
| Center-Looking Score | May include determining, when more than one target or cue is important at the same point in time or a point of regard, whether a user's strategy is to look at a central point in-between targets. Huttermann et al (2014). |
| Target-Looking Score | May include when more than one target or cue is important at the same point in time a strategy, where the user engages in saccades from one target to the next. Huttermann et al (2014). |

The Visual Performance Exam may further include calculation of any one or more of the following eye acuity variables:

| Eye Acuity Variable | Example parameters |
|---|---|
| Visual Acuity Score | May include acuteness or clearness of vision, which may be dependent on optical and neural factors, e.g., (i) the sharpness of the retinal focus within the eye, (ii) the intactness and functioning of the retina, and (iii) the sensitivity of the interpretative faculty of the brain. Commonly measured by using the Snellen Chart or a Landolt C. |
| Static Visual Acuity Score | May include the ability to observe stationary detail in varying contrast conditions. The Static Visual Acuity Grade/Score may be determined by a combination of accuracy in recognition and may or may not include time, may or may not include angular velocities, may or may not include various contrast conditions. |

-continued

| Eye Acuity Variable | Example parameters |
| --- | --- |
| Dynamic Visual Acuity Score | May include the ability to observe detail while movement is occurring in varying contrast conditions. The Dynamic Visual Acuity Grade/Score may be determined by a combination of accuracy in recognition and may or may not include time, may or may not include angular velocities, may or may not include various contrast conditions. |
| Visual Contrast Sensitivity Score | The human contrast sensitivity function may show a typical band-pass filter shape peaking at around 4 cycles per degree with sensitivity dropping off either side of the peak.[1] This may indicate that the human visual system is most sensitive in detecting contrast differences occurring at 4 cycles per degree, e.g. at this spatial frequency humans can detect lower contrast differences than at any other spatial frequency. The high-frequency cut-off may represent the optical limitations of the visual system's ability to resolve detail and may be about 60 cycles per degree. The high-frequency cut-off may be related to the packing density of the retinal photoreceptor cells: a finer matrix can resolve finer gratings. The low frequency drop-off may be due to lateral inhibition within the retinal ganglion cells. A retinal ganglion cell may present a center region with either excitation or inhibition and a surround region with the opposite sign. By using coarse gratings, the bright bands may fall on the inhibitory as well as the excitatory region of the ganglion cell resulting in lateral inhibition and account for the low-frequency drop-off of the human contrast sensitivity function. A recommendation using Weber contrast may be defined as I and $I_b$ representing the luminance of the features and the background, respectively. The measure may also be referred to as a Weber fraction since it is the term which is constant in Weber's Law. Weber contrast may be used in cases where small features are present on a large uniform background, e.g., where the average luminance is approximately equal to the background luminance. The formula may be $(I - I_b)/I_b$ |

The Visual Performance Exam may further include calculation of any one or more of the following outcome variables:

| Outcome Variable | Example parameters |
| --- | --- |
| Performance Statistics | These may vary per sport and report. Some examples may be on-base percentage, batting average, return of serve percentage, etc. |
| Task Parameter Information Score | May include various aspects of the task at hand including but not limited to distance, speed, velocity, angles, heights etc. Task Parameter Information may be relevant scientific information (to include but not limited to physics, biomechanics, perceptual-motor, mathematical, neuro-scientific, physical) on what is required in order to affect a performance, e.g., open and closed skills. The task Parameters may then be scored in order to provide input on the degree of difficulty in one or more categories. |
| Life-Span Development Stage | May include a range of time over the human developmental lifespan, related to development of perceptual-cognitive, visual, and motor skills. |
| Attention Score | Attention may include the cognitive process of selectively concentrating on one aspect of the environment while ignoring other things. Attention may have also been referred to as the allocation of processing resources. Attention can be extrapolated via eye tracking. Attention score can be calculated based on how many relevant targets/cues are viewed as a percentage of overall viewing. |
| Anticipation Score | May include a measure of reaction time score and decision making accuracy. |
| Decision Making Score | May include a combination of the Reaction Time Grade/Score and a response associated with the outcome of the task. One example may be, right or left, high or low decision making with a reaction time of one second. |

-continued

| Outcome Variable | Example parameters |
|---|---|
| Game Intelligence Score | May include an outcome score referring to an individual's ability to make sense (cognitively, visually, and motorically) of a given task or set or parameters. Game intelligence may include fast and accurate decision-making, anticipation, cue identification, etc. |
| Short-term Memory Score | May include recognizing an important cue that is previously unknown or unique. May refer to the consistency of placement of gaze at specific critical moments in time from one repetition to the next and includes at least one outcome measure, e.g., anticipation or decision making score. It may be task-specific. Short-term memory score may be inferred from chunking important cues repeatedly and providing quick and accurate outcome measures consistently. |
| Direction Score | Direction score may evaluate the ability of the participant to follow directions of the task. During a pre-task explanation and test, the score may evaluate whether the user followed the directions required to begin the task, such as whether a user looked at an object when asked to do so. The metrics for the direction score may or may not be binary "Yes" or "No", "Green light" or "Red Light," and they may or may not be a percentage of "readiness." |
| Situational Awareness Score (level 1) | Level 1 may include the perception of essential cues or vital information to create an accurate picture of the situation. |
| Situational Awareness Score (level 2) | Level 2 may deal with comprehension, which may encompass how individuals combine, interpret, store and retain information. |
| Situational Awareness Score (level 3) | Level 3 may include the ability to project from past knowledge to current and future situations. This may impact the temporal-spatial aspects of the performance, including the timing of situation-specific actions and the decisions that are made under duress. |

It should be appreciated that certain one or more of the above parameters are sometimes used in association with measures of one or more of "visual search," "visual strength," and "visual acuity." However, any subset and/or combination of the above parameters may be used by the disclosed Visual Performance Exam to develop a visual performance score, and/or evaluation, and/or related training/therapy activities and/or re-scoring. Nevertheless, below is an exemplary embodiment of certain combinations of the above metrics as applied to certain measures of visual acuity and/or visual strength, and/or visual search, and should therefore be construed as only exemplary in nature.

Visual Acuity

As described above, a measure of Visual Acuity may include a measure of the ability to see clearly and in detail. Specifically, in one exemplary embodiment of the disclosed Visual Performance Exam, the system may test the following metrics as being components of a measure of visual acuity:

- Static visual acuity
- Dynamic visual acuity
- Color blindness
- Visual field test
- Contrast sensitivity
- Eye Dominance
- Refractive status (e.g., for indicating astigmatism or refractive error)
- Ocular Alignment
- Dry eye/Blinks
- Astigmatism
- Accommodation
- Vergence
- Accommodative facility and vergence ability
- Convergence
- Divergence Static Visual Acuity may include the ability to see clearly and in detail using focal vision when both the target and individual are stationary. Static visual acuity may entail identification via detailed visual scrutiny. When visually targeting an object(s) at various distances, vision may stabilize on a fixed location. The presently disclosed Visual Performance Exam system may measure various distances throughout the test and prompt test subjects to respond to a cue.

Dynamic Visual Acuity may include the ability to see clearly and in detail using focal vision when either the target is moving, the individual is moving, or both are moving. Dynamic Visual Acuity may entail identification via detailed visual scrutiny during movement. Dynamic Visual Acuity may be used when visually targeting an object(s) at various distances while the test subject is moving, the target is moving, or both are moving. The presently disclosed Visual Performance Exam system may measure various distances. For example, throughout the test, the test subject may be prompted to respond to objects that are moving while the test subject is (a) stationary, and (b) moving, or where the object is still but the test subject is moving. For instance, a test subject may be prompted to identify characteristics of the object e.g., numbers on a ball.

Eye Dominance may define the eye that the person prefers to use (also referred to as "directing eye"). The dominant eye may be the stronger eye. Dominance may contribute to aiming and preparing a set up position to aim. Eye dominance may play a role in aiming, at any distance, e.g., when the test subject shoots a weapon or engages in close combat using weapons. The presently disclosed Visual Performance Exam system may identify dominance during a short test. Metrics gathered during this test may provide further information on the scale of dominance.

Accommodation may include the speed at which the accommodative system can change in response to stimuli in order to see clearly across distances. Accomodation may be a metric of ocular alignment, and it may be used for indicating one or more of: Myopic (near vision), Hyperopic (far vision), Accomodative Insufficency, III-Sustained Accomodation, Accomodative Infacility, Paralysis of Accomodation, and/or Spasm of Accomodation. Ocular alignment may also be determined using accommodative convergence/accommodation ratio, and/or negative relative accommodation.

Vergence may include the flexibility of fusion. In normal functioning adults, training on accommodative vergence facility may show a 65% increase. Vergence may be a metric of ocular alignment, and it may be used for indicating one or more of: Convergence Insufficiency, Convergence excess, Divergence insufficiency, Divergence excess, Browns Syndrome, Fusional Vergence Dysfunction, Microstrabisimus, Vertical heterophoria, Exophoria, Esophoria, Strabismus (cross-eyed), Nystagmus (involuntary side-to-side), Dissociated vertical deviation (DVD), and/or Amblyopia.

Accommodative facility and vergence ability can be tested and trained by near, far, or near object focusing. A practical example of this ability may include looking at something in your hand, e.g., cell phone and then looking out to an object in the distance, e.g., a building. In normal functioning adults, accommodative facility and vergence ability may be improved by 24%.

Convergence may include the ability of the eyes to "converge" on a target in order to maintain a single image. In normal functioning adults, vision training, may improve convergence by 73%.

Divergence may include the ability of the eyes to maintain a single image when objects are diverging (moving apart). In normal functioning adults, vision training may improve divergence by 155%.

Visual Strength

Visual Strength may include the ability to use the muscles around the eyes to move the eyes quickly and sustain eye behavior over time. In one exemplary embodiment, the presently disclosed Visual Performance Exam system may test the following visual strength metrics:

Pursuits (ocular movement)
Saccades (ocular movement)
Vergence Function (eye teaming)
Accommodative function (eye teaming)
Depth Perception
Peripheral range
Peripheral recognition Depth Perception may include the ability to see the world in three dimensions, e.g., where the eyes' convergence in space to form detail is processed by the brain. Without depth perception, a person may misjudge how far an object is from them, e.g., they may think it is closer or further away. Depth perception may be useful in tasks from walking down stairs to shaking hands, to determining how long it may take to reach a given location. The presently disclosed Visual Performance Exam system may measure depth perception by determining targets of the same size at differing distances from the test subject, e.g., the test subject may determine which target is closer. Eye tracking metrics may help to verify the depth perception through vectors of the eye and may quantify the depth perception on a gradient for the individual. Depth perception may be used for determining positive relative accommodation.

Peripheral Range may include the visual distance (left, right, forward, back) of peripheral vision. Peripheral vision may allow a person to see motion before seeing detail. A wider range of peripheral vision may allow the test subject to see more of the field of view. Peripheral range may be important when there is a large visual space to be examined, e.g., a large field or room. The presently disclosed Visual Performance Exam system may measure peripheral range by having the test subject stand with the head still and eyes stable on a target directly in front of them. Targets of differing colors and numbers may be placed in a semi-circle starting at 90 degrees from the central visual location. The test subject may keep eyes straight and say the color on each target. Eye tracking visual stability (e.g., a search metric) may be measured at the same time as peripheral range. When the eyes move, the range may be determined and a score may be calculated.

Peripheral Recognition may include the visual distance (e.g., left, right, front, back) of peripheral vision, including the ability to recognize detail. Peripheral vision may allow a person to see motion before seeing detail, e.g., recognizing what is in the periphery sooner may allow for faster anticipation. Peripheral recognition may be useful where there is a large visual space to be examined and there are multiple targets in the periphery, e.g., a large field or room. The presently disclosed Visual Performance Exam system may measure peripheral recognition with the test subject standing head still and eyes stable on a target directly in front of them. Targets of differing colors and numbers may be placed in a semi-circle starting at 90 degrees from the central visual location. The test subject may keep eyes straight and say the color and number on each target. Eye tracking measured visual stability (e.g., a search metric) may be measured at the same time as peripheral recognition. When the eyes move, the range may be determined and a score may be calculated.

Visual Search

Visual Search may include the skill of knowing where to look, when to look and what to look for higher order brain processing and decision making. In one exemplary embodiment, the presently disclosed Visual Performance Exam system may test the following visual search metrics:

Eye-Hand coordination
Speed of recognition
Motor response time
Visual-motor reaction time
Eye-body coordination
Visual coincidence anticipation
Vision and balance
Field dependence & independence
Visual black holes
Target stabilization
Visual Processing time
Vision and Decision making
Visual Stress
Vision and Split-attention
Visual attention
Visual stabilization
Disinhibition
Pursuit tracking
Time-to-target
Visual routines Visual Stress may include when a person perceives stress and vision changes, e.g., where vision may become narrow and inflexible due to stress. Visual stress may be important in that, similar to stage fright, visual "fright" may hinder the test subject from seeing and processing what is happening in the environment. Visual Stress may be important when there is perceived stress. The presently disclosed Visual Performance Exam system may measure visual stress using competition with consequences to create a stress response. Eye tracking may measure a change as a) visual target cues and/or b) visual routines.

Visual and Split-Attention may encompass both central (focal) and peripheral vision, referring to a person's ability to recognize and attend to both areas of vision. Visual and split-attention may be important in dynamic situations where there is a need to attend to multiple pieces of visual information in order to perform successfully. It may be important in complex, dynamic battlefields, e.g., a threat directly ahead while other possible threats may be located to the left and right, as well as friendlies within the environment. The presently disclosed Visual Performance Exam system may measure visual and split-attention using multiple moving targets, where the test subject may be prompted to identify as many targets as possible and distinguish the targets via color.

Disinhibition may include the ability to not look. Disinhibition may be important in situations where there may be multiple visual stimuli. The ability to not look at unimportant cues may be as important as the ability to focus on important cues. Disinhibition may be important in complex, dynamic battlefields, e.g., knowing where teammates are but not having to look at them and instead being able to focus on an enemy target. The presently disclosed Visual Performance Exam system may test disinhibition using multiple moving targets, and scoring the test subject on how many targets he looked at that he should not have looked at, that is, where he was unable to inhibit a response.

Visual field range may include peripheral vision range and refer to how far a person can see when the eyes are fixed straight ahead. In normal functioning adults, visual field range may be 100 degrees horizontally from the nose, and 60 degrees above and 75 degrees below the horizontal meridian. In a study with patients who had glaucoma, visual field training was associated with a 13.9% increase in the visual field. In normal functioning adults, visual field training could result in a highly significant increase in the visual field by 15.4% (5.43 bits). Visual field range may be used to determine visual field loss, blind spots (Scotoma), and/or peripheral sensitivity.

Saccadic eye movements may be used to direct foveal fixation towards objects of interest e.g. a moving target. Saccades may depend on information from the edges of a person's vision, in the periphery, to tell the brain that there is something of interest in the field that should be looked at. In normal functioning adults, vertical saccades have been improved with effective training by 38% and horizontal saccades were improved by 31%.

Eye dominance: Eye dominance may refer to having one eye that is stronger than the other. Eye dominance may also relate to opposite hand (cross) dominance. For example, eye dominance may mean being right handed but being left-eye dominant. Eye dominance can be a factor in performance, especially in activities such as archery and shooting where cross dominance can cause the aim to be pulled toward the dominant eye. The dominant eye may have priority in visual processing and may even inhibit non-dominant eye representations. The basis of this training may be to create "ambidexterity," or being able to use both eyes and both sides of the body equally. Through practice, the non-dominant eye can be trained to work more efficiently in specific tasks. The brain may be "hard-wired", so the goal of training/therapy may be to enhance the visual accuracy of the non-dominant eye (rather than to change eye dominance). Eye dominance may be categorized as "weak" or "strong." Strong eye dominance may apply to approximately 39% of the population and weak eye dominance may apply to about 61% of the population. Complete symmetry between the left and right eye may be represented as a ratio of 1.0:1.0 (i.e., 50 left eye, 50 right eye). An example of moderate eye dominance (aka: "Weak eye dominance") may include: 45 left eye weak, 53 right eye dominant. Significant eye dominance (aka: "Strong eye dominance") may start with a ratio of 1.0:1.8 (i.e., 20 left eye weak, 80 right eye dominant). With specific vision training/therapy, a person's eye dominance can result in complete symmetry.

Dynamic Visual Acuity (DVA) may refer to the ability to see a moving object, or for example, to be moving while seeing a stationary object, or as another example, where both the subject and the object are moving. This may be a common function of the human visual system. Over distances and speed, dynamic visual acuity may be reduced from 20/20 visual acuity. However, with vision training, DVA may be improved by up to 12%. DVA may be improved to 20/20 vision in the vertical plane, and the left, right, upward and downward planes may also show significant improvements. These results may translate to performance improvements when catching a ball, e.g., from 84% pre-training to 93% post-training (a 9% increase).

Depth perception may refer to the ability to perceive the relative distance of objects in one's visual field. In normal functioning adults across distances up to 4.5 meters, depth perception may significantly improve from pre- to post-training. In fast interceptive sports (e.g., table tennis) a causal relationship between improvement in depth perception, hand-eye coordination, and performance of players may be found. Table tennis players may improve their match statistics by 9% with training.

Split-Attention may occur when the same modality (e.g., visual) is used for various types of information within the same setting. This may occur in everyday life as well as military operations. One study of split attention focused on making decisions while teleoperating robots, others on texting and driving. There is little science on how to train for improvements when split-attention is required. To date, science can assist with understanding the cognitive load effects of split attention, which are significant, from reducing efficiency to missing visual cues, to slowing response time. Results from such studies may help to reduce accidents by ergonomic changes such as placing important visual cues and instructions one-at-a-time within certain locations in the visual field.

Disinhibition may refer to the ability not to look. Sometimes, not looking at something (e.g., a distractor) is just as integral as focusing on what is important. Eye tracking may permit accurate assessments of disinhibition. Disinhibition may be used as one factor for research and diagnosis of people with various clinical disorders (e.g., schizophrenia, Alzheimer's, concussion, depression). However, disinhibition may also be highly relevant to performance related settings with normal functioning adults. Disinhibition may be inferred in normal functioning humans during performance activities (e.g., sport). This can be conducted via search rates (i.e., fixations over time) of skilled versus less skilled individuals. Research on direct measurement of disinhibition in normal functioning humans may be lacking. However, as inferred via search rates and skill levels, differences from training can be up to 80%. With effective training, the less skilled individual can reduce search rate scores by up to 50%.

Vision, information processing and decision making may all be interrelated. The ability to see, think, and do can be tested and trained in terms of speed of response and accuracy of response. In go/no-go training of normal functioning adults, a decrease in mistakes of 78% alongside a 25% increase in speed may result in faster and more accurate results. The Visual Performance Exam system may assess and train information processing and decision making.

Anticipation may refer to the ability to see, interpret, and make decisions about future occurrences. In normal functioning adults, after vision training, this ability may improve by 400 milliseconds. The Visual Performance Exam may assess and train anticipation to improve performance.

Eye-hand coordination may be important for many tasks. One component of eye-hand coordination may include the ability to test and train the reflexes and accuracy of central and peripheral vision. In normal functioning adults, after vision training, the speed of reflexes may be improved by 95% and the number of missed targets may be reduced by 74%. In other training, an increase in correct hits may show a 114% improvement alongside a 72% decrease in number of misses.

Visual recognition may refer to the ability to understand what is being seen. In other words, visual recognition may include the ability to interpret what is seen. In reading tests of normal functioning adults, visual recognition training may result in a 32 word per minute (significant) increase. These results alongside training on expanded visual field range may cause an increase in speed reading by 45%. Additional studies have corroborated such results by showing that training may cause increases in speed reading ranging from 41% to 54%.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for hosting one or more visual assessments on a web platform, the method including:

hosting one or more visual assessments on a hosting web platform, each assessment evaluating a different aspect of visual performance or neurological function based on metrics computed from eye tracking data;

causing a user device to display a user interface of the hosting web platform to a user, the user interface presenting the hosted one or more visual assessments;

receiving, via the hosting web platform, a request from the user device to access a visual assessment hosted on the hosting web platform;

administering the visual assessment to the user;

causing a n eye tracker associated with the user to record eye tracking data associated with the user's eye movements, in response to the visual assessment;

computing, using the hosting web platform, a value of an assessment-specific metric, wherein:

the assessment-specific metric is a high level eye movement metric, and is computed based on respective values from each of a plurality of different low level eye movement metrics computed from the eye tracking data wherein each of the plurality of different low-level metrics is indicative of detection of oculomotor events in the eye tracking data of a respective one of fixations, saccades, smooth pursuits, microsaccades, glissades, drifts, tremors, or square-wave jerks;

the assessment-specific metric relates to the aspect of visual performance evaluated by the visual assessment; and the assessment-specific metric corresponds to one or more of a user's skill level at a specific task or at least one aspect of the user's visual performance or neurological state;

comparing the value of the computed assessment-specific metric to a metric associated with one or more individuals;

determining, based on one or more of the comparison or the assessment-specific metric, a user-specific conclusion on one or more of the user's visual performance or neurological state; and generating an output that includes the user-specific conclusion.

2. The computer-implemented method of claim 1, wherein the user-specific conclusion includes one or more of an indication of the user's visual acuity or visual strength, an indication of a binocular vision disorder or dysfunction, an indication of a sensory motor disorder or dysfunction, or an indication of a status of a neurological disorder of the user.

3. The computer-implemented method of claim 1, further comprising:

generating a user-specific progression for the user by comparing the user-specific conclusion with at least one prior user-specific conclusion;

wherein the output includes an indication of the user-specific progression.

4. The computer-implemented method of claim 1, wherein the one or more visual assessments are configured such that the assessment-specific metrics for each of the one or more visual assessments is in a standardized format.

5. The computer-implemented method of claim 1, wherein the eye tracker includes one or more wearable camera.

6. The computer-implemented method of claim 5, wherein the eye tracker is associated with a device that further includes one or more of:

at least one sensor configured to detect a body position of the user; or at least one sensor configured to detect an orientation or location of the wearable camera.

7. The computer-implemented method of claim 5, wherein the eye tracker is integrated into:

a visor;

a helmet;

an implanted device;

spectacles; or one or more contact lenses.

8. The computer-implemented method of claim 1, wherein the metric associated with one or more individuals is computed from further eye tracking data received from the one or more individual in response to a visual assessment different than the visual assessment administered to the user.

9. The computer-implemented method of claim 1, wherein the one or more visual assessments includes one or more of:

a circular, horizontal, or vertical smooth pursuit tracking test;

a horizontal or vertical saccade test;

an interpupillary distance test;

a fixation stability test;

a static or dynamic visual acuity test;

a dry eye indicator test;

a contrast sensitivity test;

a reaction time test;

a reaction speed test;
a processing speed test;
a reaction accuracy test;
a cardinal gaze position test;
a binocular vision test;
an eye dominance or preference test;
a color-vision test;
a visual field test; or
an astigmatism test.

10. A system for hosting one or more visual assessments on a web platform, the system including:
a data storage device storing instructions for hosting one or more visual assessments;
a processor configured to execute the instructions to perform operations, including:
hosting one or more visual assessments on a hosting web platform, each assessment evaluating a different aspect of visual performance or neurological function based on metrics computed from eye tracking data;
causing a user device to display a user interface of the hosting web platform to a user, the user interface presenting the hosted one or more visual assessments;
receiving, via the hosting web platform, a request from the user device to access a visual assessment hosted on the hosting web platform;
administering the visual assessment to the user;
causing an eye tracker associated with the user to record eye tracking data associated with the user's eye movements, in response to the visual assessment;
computing, using the hosting web platform, respective values for each of a plurality of different low-level eye movement metrics based on the eye tracking data, each of the plurality of different low-level metrics indicative of detection in the eye tracking data of a respective one of fixations, saccades, smooth pursuits, microsaccades, glissades, drifts, tremors, or square-wave jerks;
computing, using the hosting web platform, a high-level eye movement metric based on the plurality of different low-level eye movement metrics, the high-level eye movement metric including an assessment-specific metric relating to the aspect of visual performance evaluated by the visual assessment, wherein the assessment-specific metric corresponds to one or more of a user's skill level at a specific task or at least one aspect of the user's visual performance or neurological state;
comparing the computed assessment-specific metric to a metric associated with one or more individuals;
determining, based on one or more of the comparison or the assessment-specific metric, a user-specific conclusion on one or more of the user's visual performance or neurological state; and
generating an output that includes the user-specific conclusion.

11. The system of claim 10, wherein the user-specific conclusion includes one or more of an indication of the user's visual acuity or visual strength, an indication of a binocular vision disorder or dysfunction, an indication of a sensory motor disorder or dysfunction, or an indication of a status of a neurological disorder of the user.

12. The system of claim 10, the operations further including:
generating a user-specific progression for the user by comparing the user-specific conclusion with at least one prior user-specific conclusion;
wherein the output includes an indication of the user-specific progression.

13. The system of claim 10, wherein the one or more visual assessments are configured such that the assessment-specific metrics for each of the one or more visual assessments is in a standardized format.

14. The system of claim 10, wherein:
the eye tracker includes one or more wearable camera; and
the eye tracker is associated with a device that further includes one or more of:
at least one sensor configured to detect a body position of the user; or
at least one sensor configured to detect an orientation or location of the wearable camera.

15. The system of claim 14, wherein the device associated with the eye tracker includes one or more of:
a visor;
a helmet;
an implanted device;
spectacles; or
one or more contact lenses.

16. The system of claim 10, wherein the metric associated with one or more individuals is computed from further eye tracking data received from the one or more individual in response to a visual assessment different than the visual assessment administered to the user.

17. The system of claim 10, wherein the one or more visual assessments includes one or more of:
a circular, horizontal, or vertical smooth pursuit tracking test;
a horizontal or vertical saccade test;
an interpupillary distance test;
a fixation stability test;
a static or dynamic visual acuity test;
a dry eye indicator test;
a contrast sensitivity test;
a reaction time test;
a reaction speed test;
a processing speed test;
a reaction accuracy test;
a cardinal gaze position test;
a binocular vision test;
an eye dominance or preference test;
a color-vision test;
a visual field test; or
an astigmatism test.

18. A non-transitory computer-readable medium comprising instructions that are executable by a processor to perform operations including:
hosting one or more visual assessments on a hosting web platform, each assessment evaluating a different aspect of visual performance or neurological function based on metrics computed from eye tracking data;
causing a user device to display a user interface of the hosting web platform to a user, the user interface presenting the hosted one or more visual assessments;
receiving, via the hosting web platform, a request from the user device to access a visual assessment hosted on the hosting web platform;
administering the visual assessment to the user;
causing an eye tracker associated with the user to record eye tracking data associated with the user's eye movements, in response to the visual assessment;

computing, using the hosting web platform, respective values of each of a plurality of different low-level eye movement metrics based on the eye tracking data, each of the plurality of different low-level eye movement metrics indicative of detection in the eye tracking data of a respective one of fixations, saccades, smooth pursuits, microsaccades, glissades, drifts, tremors, or square-wave jerks;

computing, using the hosting web platform, a high-level eye movement metric based on the plurality of different low-level eye movement metrics, the high-level eye movement metric including an assessment-specific metric relating to the aspect of visual performance evaluated by the visual assessment, wherein the assessment-specific metric corresponds to one or more of a user's skill level at a specific task or at least one aspect of the user's visual performance or neurological state;

comparing the computed assessment-specific metric to a metric associated with one or more individuals;

determining, based on one or more of the comparison or the assessment-specific metric, a user-specific conclusion on one or more of the user's visual performance or neurological state; and generating an output that includes the user-specific conclusion.

19. The computer-implemented method of claim 1, wherein:

computing each of the plurality of different low level eye movement metrics based on the eye tracking data includes:

filtering the eye tracking data;

identifying and removing any artifacts from the filtered eye tracking data; and classifying any oculomotor events in the eye tracking data corresponding to the low level eye movement metric using ternary eye movement classification; and the plurality of different low level eye movement metrics are based on the classified oculomotor events in the eye tracking data.

* * * * *